(12) United States Patent
Picha et al.

(10) Patent No.: US 11,123,173 B2
(45) Date of Patent: Sep. 21, 2021

(54) IMPLANT COMPRISING FIRST AND SECOND SETS OF PILLARS FOR ATTACHING A TENDON OR A LIGAMENT TO A HARD TISSUE

(71) Applicant: GARY A. ZWICK, TRUSTEE OF THE EVEREST TRUST UTA APRIL 20, 2017, Cleveland, OH (US)

(72) Inventors: George J. Picha, Brecksville, OH (US); James Price, Stow, OH (US); Gregory Causey, Erie, CO (US)

(73) Assignee: GARY A. ZWICK, Cleveland, OH (US), TRUSTEE OF THE EVEREST TRUST UTA APRIL 20, 2017

( * ) Notice: Subject to any disclaimer, the term of this patent is extended or adjusted under 35 U.S.C. 154(b) by 0 days.

(21) Appl. No.: 17/274,462

(22) PCT Filed: Sep. 11, 2020

(86) PCT No.: PCT/US2020/050442
§ 371 (c)(1),
(2) Date: Mar. 9, 2021

(87) PCT Pub. No.: WO2021/050903
PCT Pub. Date: Mar. 18, 2021

(65) Prior Publication Data
US 2021/0259820 A1 Aug. 26, 2021

Related U.S. Application Data

(60) Provisional application No. 62/898,723, filed on Sep. 11, 2019.

(51) Int. Cl.
*A61F 2/00* (2006.01)
*A61F 2/08* (2006.01)

(52) U.S. Cl.
CPC .......... *A61F 2/0077* (2013.01); *A61F 2/0811* (2013.01); *A61F 2002/0081* (2013.01);
(Continued)

(58) Field of Classification Search
CPC ...... A61F 2/0811; A61F 2/4465; A61F 2/447; A61F 2/442; A61F 2/30767;
(Continued)

(56) References Cited

U.S. PATENT DOCUMENTS

| 2,232,336 A | 2/1941 | Meersteiner |
| 2,278,411 A | 4/1942 | Braendel |

(Continued)

FOREIGN PATENT DOCUMENTS

| DE | 837294 C | 4/1952 |
| DE | 33 22 803 A1 | 1/1985 |

(Continued)

OTHER PUBLICATIONS

Translation of DE-10325139-A1 (Year: 2004).*
(Continued)

*Primary Examiner* — Brian A Dukert
*Assistant Examiner* — Rebecca Lynee Zimmerman
(74) *Attorney, Agent, or Firm* — Pearne & Gordon LLP

(57) ABSTRACT

An implant for attaching a tendon or ligament to a hard tissue is provided. The implant includes a shaft, a convex first surface, a flat or concave second surface, first pillars for contacting a hard tissue, first slots to be occupied by the hard tissue, second pillars for contacting a tendon or ligament, and second slots to be occupied by the tendon or ligament. The implant has a first surface ratio of the sum of the volumes of the first slots to the sum of the volumes of the first pillars and the volumes of the first slots of 0.40:1 to 0.90:1, and a second surface ratio of the sum of the volumes of the second slots to the sum of the volumes of the second (Continued)

pillars and the volumes of the second slots of 0.60:1 to 0.98:1. The second surface ratio is greater than the first surface ratio.

45 Claims, 30 Drawing Sheets

(52) U.S. Cl.
CPC ............... *A61F 2002/0817* (2013.01); *A61F 2002/0882* (2013.01); *A61F 2220/0091* (2013.01)

(58) Field of Classification Search
CPC .... A61F 2/0817; A61F 2/0847; A61F 2/0876; A61F 2/30593; A61F 2/30771; A61F 2002/2835; A61F 2/0077; A61F 2002/0081; A61F 2002/0817; A61F 2002/0882; A61F 2220/0091; A61B 17/686
See application file for complete search history.

(56) References Cited

U.S. PATENT DOCUMENTS

| | | | |
|---|---|---|---|
| 2,532,296 A | 12/1950 | Giesen | |
| 3,605,123 A | 9/1971 | Hahn | |
| 3,808,606 A | 5/1974 | Tronzo | |
| 3,855,638 A | 12/1974 | Pilliar | |
| 4,237,559 A | 12/1980 | Borom | |
| 4,365,958 A | 12/1982 | Vlock | |
| 4,537,185 A | 8/1985 | Stednitz | |
| 4,608,052 A | 8/1986 | Van Kampen et al. | |
| 4,834,757 A | 5/1989 | Brantigan | |
| 4,865,603 A | 9/1989 | Noiles | |
| 5,094,618 A | 3/1992 | Sullivan | |
| 5,098,435 A | 3/1992 | Stednitz et al. | |
| 5,195,892 A | 3/1993 | Gersberg | |
| 5,207,709 A | 5/1993 | Picha | |
| 5,209,753 A | 5/1993 | Biedermann et al. | |
| 5,236,453 A | 8/1993 | Picha | |
| 5,263,953 A | 11/1993 | Bagby | |
| 5,312,256 A | 5/1994 | Scortecci | |
| 5,545,226 A | 8/1996 | Wingo et al. | |
| 5,571,185 A | 11/1996 | Schug | |
| 5,593,410 A | 1/1997 | Vrespa | |
| 5,628,630 A | 5/1997 | Misch | |
| 5,702,445 A | 12/1997 | BrÅnemark | |
| 5,720,766 A | 2/1998 | Zang et al. | |
| 5,725,581 A | 3/1998 | Brånemark | |
| 5,733,307 A | 3/1998 | Dinsdale | |
| 5,823,777 A | 10/1998 | Misch | |
| 5,833,415 A | 11/1998 | McSherry | |
| 5,876,457 A | 3/1999 | Picha et al. | |
| 6,001,100 A | 12/1999 | Sherman et al. | |
| 6,071,310 A | 6/2000 | Picha et al. | |
| 6,106,558 A | 8/2000 | Picha | |
| 6,135,772 A | 10/2000 | Jones | |
| 6,315,562 B1 | 11/2001 | Kumar | |
| 6,346,122 B1 | 2/2002 | Picha et al. | |
| 6,458,134 B1 | 10/2002 | Songer et al. | |
| 6,569,201 B2 | 5/2003 | Moumene et al. | |
| 6,789,991 B2 | 9/2004 | Hsu | |
| 6,846,313 B1 | 1/2005 | Rogers et al. | |
| 6,989,032 B2 | 1/2006 | Errico et al. | |
| 7,018,418 B2 | 3/2006 | Amrich et al. | |
| 7,041,140 B2 | 5/2006 | Picha | |
| 7,128,760 B2 | 10/2006 | Michelson | |
| 7,205,051 B2 | 4/2007 | King et al. | |
| 7,250,550 B2 | 7/2007 | Overby et al. | |
| 7,347,873 B2 | 3/2008 | Paul et al. | |
| 7,393,170 B2 | 7/2008 | Chen | |
| 7,556,648 B2 | 7/2009 | Picha et al. | |
| 7,608,107 B2 | 10/2009 | Michelson | |
| 7,691,148 B2 | 4/2010 | Michelson | |
| 7,955,512 B2 | 6/2011 | Park et al. | |
| 8,360,702 B2 | 1/2013 | Yu | |
| 8,470,036 B2 | 6/2013 | Barnes et al. | |
| 8,551,173 B2 | 10/2013 | Lechmann et al. | |
| 8,672,940 B2 | 3/2014 | Prager | |
| 8,685,070 B2 | 4/2014 | Rupp et al. | |
| 8,764,831 B2 | 7/2014 | Lechmann et al. | |
| 8,771,354 B2 | 7/2014 | Picha et al. | |
| 8,900,302 B2 | 12/2014 | Gonzalez-Hernandez | |
| 8,986,007 B2 | 3/2015 | Chen | |
| 9,198,701 B2 | 12/2015 | Prien et al. | |
| 9,333,081 B2 | 5/2016 | Picha et al. | |
| 9,456,856 B2 | 10/2016 | Ballard | |
| 9,579,206 B2 | 2/2017 | Picha et al. | |
| 9,581,183 B2 | 2/2017 | Lajewardi et al. | |
| 9,801,673 B2 | 10/2017 | Aeschlimann et al. | |
| 9,808,346 B2 | 11/2017 | Stark | |
| 9,827,028 B2 | 11/2017 | Biedermann et al. | |
| 9,949,776 B2 | 4/2018 | Mobasser et al. | |
| 10,154,908 B2 | 12/2018 | Picha et al. | |
| 10,507,041 B2 | 12/2019 | Tsai et al. | |
| 2001/0039454 A1* | 11/2001 | Ricci | A61F 2/32 623/23.5 |
| 2002/0040242 A1 | 4/2002 | Picha et al. | |
| 2002/0106393 A1 | 8/2002 | Bianchi et al. | |
| 2002/0123752 A1 | 9/2002 | Schultheiss et al. | |
| 2004/0093028 A1 | 5/2004 | Ruff | |
| 2004/0122518 A1 | 6/2004 | Rhoda | |
| 2004/0181286 A1 | 9/2004 | Michelson | |
| 2004/0223830 A1 | 11/2004 | Panasik et al. | |
| 2004/0260291 A1 | 12/2004 | Jensen | |
| 2004/0267267 A1 | 12/2004 | Daniels et al. | |
| 2005/0033289 A1 | 2/2005 | Warren et al. | |
| 2005/0049706 A1 | 3/2005 | Brodke et al. | |
| 2005/0246021 A1 | 11/2005 | Ringeisen et al. | |
| 2005/0283158 A1 | 12/2005 | West | |
| 2006/0015184 A1 | 1/2006 | Winterbottom et al. | |
| 2006/0030884 A1 | 2/2006 | Yeung | |
| 2006/0106390 A1 | 5/2006 | Jensen et al. | |
| 2006/0189993 A1 | 8/2006 | Stone | |
| 2007/0123988 A1 | 5/2007 | Coughlin | |
| 2007/0166124 A1 | 7/2007 | Hsu | |
| 2007/0168037 A1 | 7/2007 | Posnick | |
| 2008/0109037 A1 | 5/2008 | Steiner | |
| 2008/0287910 A1 | 11/2008 | Picha | |
| 2008/0306554 A1 | 12/2008 | McKinley | |
| 2009/0069904 A1 | 3/2009 | Picha | |
| 2009/0105772 A1 | 4/2009 | Seebeck | |
| 2009/0204214 A1 | 8/2009 | Fuji et al. | |
| 2010/0042167 A1 | 2/2010 | Nebosky et al. | |
| 2010/0211118 A1 | 8/2010 | Christen et al. | |
| 2010/0256758 A1 | 10/2010 | Gordon et al. | |
| 2010/0298950 A1 | 11/2010 | McDonnell et al. | |
| 2011/0093020 A1 | 4/2011 | Wu | |
| 2011/0125264 A1 | 5/2011 | Bagga et al. | |
| 2011/0213467 A1 | 9/2011 | Lozier et al. | |
| 2011/0218585 A1 | 9/2011 | Krinke et al. | |
| 2011/0320000 A1 | 12/2011 | O'Neil et al. | |
| 2012/0265258 A1 | 10/2012 | Garvey | |
| 2012/0271427 A1 | 10/2012 | Serafin | |
| 2013/0090735 A1 | 4/2013 | Mermuys et al. | |
| 2013/0110241 A1 | 5/2013 | Palmatier et al. | |
| 2013/0116793 A1 | 5/2013 | Kloss | |
| 2013/0325129 A1 | 12/2013 | Huang | |
| 2014/0025181 A1 | 1/2014 | Vanasse et al. | |
| 2014/0180432 A1 | 6/2014 | Conway et al. | |
| 2014/0303729 A1 | 10/2014 | Lee | |
| 2015/0305878 A1 | 10/2015 | O'Neil et al. | |
| 2015/0359575 A1 | 12/2015 | Pech et al. | |
| 2016/0067048 A1 | 3/2016 | Hensley et al. | |
| 2017/0119530 A1* | 5/2017 | Picha | A61L 27/06 |
| 2019/0388131 A1 | 12/2019 | Mehl et al. | |
| 2020/0022742 A1 | 1/2020 | Li et al. | |

(56) References Cited

U.S. PATENT DOCUMENTS

| | | |
|---|---|---|
| 2020/0205870 A1 | 7/2020 | Walsh et al. |
| 2020/0289179 A1 | 9/2020 | Zander et al. |

FOREIGN PATENT DOCUMENTS

| | | | | |
|---|---|---|---|---|
| DE | 103 25 139 | A1 | 12/2004 | |
| DE | 10325139 | A1 * | 12/2004 | ........... A61B 17/686 |
| EP | 0 162 604 | A1 | 11/1985 | |
| EP | 0 269 256 | A1 | 6/1988 | |
| FR | 3 019 032 | A1 | 10/2015 | |
| GB | 2 181 354 | A | 4/1987 | |
| WO | 96/40020 | A1 | 12/1996 | |
| WO | 199640015 | A1 | 12/1996 | |
| WO | 2002017823 | A1 | 3/2002 | |
| WO | 2002032345 | A2 | 4/2002 | |
| WO | 2009022911 | A2 | 2/2009 | |
| WO | 2009108789 | A1 | 9/2009 | |
| WO | 2013063069 | A1 | 5/2013 | |
| WO | 2016018160 | A1 | 2/2016 | |
| WO | 2016082880 | A1 | 6/2016 | |
| WO | 2016/130878 | A1 | 8/2016 | |
| WO | 2018/053403 | A1 | 3/2018 | |
| WO | 201865400 | A1 | 9/2018 | |
| WO | 2018165403 | A1 | 9/2018 | |
| WO | 2018165405 | A1 | 9/2018 | |
| WO | 2018169929 | A1 | 9/2018 | |
| WO | 2019199850 | A1 | 10/2019 | |
| WO | 2021050712 | A1 | 3/2021 | |

OTHER PUBLICATIONS

International Search Report and Written Opinion dated Dec. 3, 2020 for International Application No. PCT/US2020/050442.
Hulbert, S.F., et al.; "Materials of Construction for Artificial Bone Segments"; Research in Dental and Medical Materials (Edward Korostoff ed., 1969), pp. 19-67.
Bobyn, J.D., et al.; "The Optimum Pore Size for the Fixation of Porous-Surfaced Metal Implants by the Ingrowth of Bone"; Clinical Orthopaedics and Related Research, Section III Basic Science and Pathology, No. 150; Jul.-Aug. 1980; pp. 263-270.
Itala, A.I., et al.; "Pore Diameter of More Than 100 μm Is Not Requisite for Bone Ingrowth in Rabbits"; 58 Journal of Biomedical Materials Research (Applied Biomaterials); 2001; pp. 679-683.
Briem, D., et al.; "Response of primary fibroblasts and osteoblasts to plasma treated polyetheretherketone (PEEK) surfaces"; 16 Journal of Materials Science Materials in Medicine; 2005; pp. 671-677.
Biomechanics, BME 315; "Elastic anisotropy of bone" (http://silver.neep.wise.edu/~lakes/BME315N3.pdf—accessed Dec. 8, 2010); p. 1.
Dai, K., "Rational Utilization of the Stress Shielding Effect of Implants"; Biomechanics and Biomaterials in Orthopedics (ed. Dominique G. Poitout, Springer-Verlag London Limited, Singapore, 2004); pp. title, copyright, and 208-215.
McPherson, E.J., "Adult Reconstruction"; Review of Orthopaedics: Expert Consult; Fifth Edition (ed. Mark D. Miller, Saunders Elsevier, U.S., 2008); pp. 312-313, Section 4; "Complications in fixation," subsection a, "Stress shielding."
Bobyn, et al.; "Characteristics of bone ingrowth and interface mechanics of a new porous tantalum biomaterial"; The Journal of Bone & Joint Surgery (Br); vol. 81-B, No. 5; Sep. 1999; pp. 907-914.
Colton et al., "Screws-Form and Function," AOTrauma (Nov. 2012), pp. 1-10.
Jain et al., "Advances in Spinal Interbody Cages," Orthop. Surg., vol. 8, p. 278 (abstract only) (Aug. 2016).
Chong et al., "The design evolution of interbody cages in anterior cervical discectomy and fusion: a systematic review," BMC Musculoskeletal Disorders, DOI 10.1186/s12891-015-0546-x, pp. 1-11 (Apr. 25, 2015).
Pawtex, "ConnectSPINE TM) PPM (TM) (Porous Paw Metal) Anterior Cervical Interbody Fusion Case (ACIF)," pp. 1-2, available at http://www.cusmed.com/porous-paw-metal-anterior-cervical-interbody-fusion-cage.html, last accessed Mar. 7, 2018.
Zimmer Biomet, "TM-S Cervial Fusion Device," pp. 1-11, available at http://www.zimmerbiomet.com/medical-professionals/spine/product/tm-s-device.html; last accessed Mar. 7, 2018.
Akoto et al., "Press-fit fixation using autologous bone in the tibial canal causes less enlargement of bone tunnel diameter in ACL reconstruction-a CT scan analysis three months postoperatively", BMC Musculoskeletal Disorders, (2015) 16:200, pp. 1-9, DOI 10.1186/s12891-015-0656-5.
Akoto et al., "ACL reconstruction with quadriceps tendon graft and press-fit fixation versus quadruple hamstring graft and interference screw fixation—a matched pair analysis after on year follow up", BMC Musculoskeletal Disorders, (2019)20:109, pp. 1-7, https://doi.org/10.1186/s12891-019-2499-y.
Apostolakos et al., "The enthesis: a review of the tendon-to-bone insertion", Muscles, Ligaments and Tendons Journal 2014, 4 (3): 333-342.
Benjamin et al., "The 'Enthesis' Organ Concept", American College of Rheumatology, Arthritis & Rheumatism, vol. 50, No. 10, Oct. 2004, pp. 3306-3313; DOI 10.1002/art.20566.
Benjamin et al., "Where tendons and ligaments meet bone: attachment sites ('entheses') in relation to exercise and/or mechanical load", J Anat. (2006) 208, pp. 471-490.
The Editors of Encyclopaedia Britannica, "Tendon", www.britannica.com/science/tendon, Accessed Sep. 8, 2020, pp. 1-12.
Caekebeke et a., "Distal biceps tendon repair: comparison of clinical and radiological outcome between bioabsorbable and nonabsorbable screws", Journal of Shoulder and Elbow Surgery, Mar. 2016, vol. 25, Issue 3, pp. 349-354, Abstract Only, pp. 1-2.
Dovan et al., "Flexor digitorum profundus tendon to bone tunnel repair: a vascularization and histologic study in canines", J. Hand Surg. Am., Mar. 2005, 30(2), pp. 246-257, https://www.ncbi.nlm.nih.gov/pubmed/15781346, Accessed Jun. 17, 2019, Abstract Only, pp. 1-2.
Fritsch et al., "Graft Preparation Technique to Optimize Hamstring Graft Diameter for Anterior Cruciate Ligament Reconstruction", Arthroscopy Techniques, vol. 6, No. 6 Dec. 2017, pp. e2169-e2175.
Hayes et al., "A review of methods to measure tendon dimensions", Journal of Orthopaedic Surgery and Research, 2019 14:18, pp. 1-12, https://doi.org/10.1186/s13018-018-1056-y.
Lui et al., "Biology and augmentation of tendon-bone insertion repair", Journal of Orthopaedic Surgery and Research, 2010, 5:59, pp. 1-14, http://www.josr-online.com/content/5/1/59.
Mahapatra et al., "Anterior cruciate ligament repair—past, present and future", Journal of Experimental Orthopaedics, (2018)5:20, pp. 1-10, https://doi.org/10.1186/s40634-018-0136-6.
Matsen, "Repair of Rotator Cuff Tears: Surgery for shoulders with torn rotator cuff tendons can lessen shoulder pain and improve function without acromioplasty", Feb. 10, 2005, pp. 1-11.
Omar et al., "Anatomical and magnetic resonance imaging study of the medical collateral ligament of the ankle joint", Alexandria Journal of Medicine, (2015), pp. 1-9, http://dx.doi.org/10.1016/j.ajme.2015.04.003.
Optim Orthopedics, "Midfoot Fusion", https://www.optimhealth.com/midfoot-fusion, Accessed Jul. 23, 2019, pp. 1-2.
Patil, et al., "Morphometric Dimensions of the Calcaneonavicular (Spring) Ligament", Aug. 1, 2007, https://journals.sagepub.com/doi/abs/10.3113/FAI.2007.0927?journalCode-faib, Access Sep. 5, 2019, Abstract Only, p. 1.
Pfeiffer et al., "Biomechanical Comparison of Suture Anchor vs. Transosseous Tunnel Repair for Acute Quadriceps Tendon Rupture", ORS Annual Meeting, 2014, poster 1708, https://www.ors.org/Transactions/60/1708.pdf, pp. 1-3.
Silva et al., "The insertion of the canine flexor digitorum profundus tendon heals slowly following injury and suture repair", Journal of Orthopaedic Research, 20 (2002) pp. 447-453.
So et al., "Split Peroneus Longus Free Tendon Autograft Transplantation for the Treatment of Neglected Extensor Hallucis Longus Tendon Laceration: A Case Report", The Journal of Foot & Ankle Surgery, 57 (2018) pp. 210-214.

(56) References Cited

OTHER PUBLICATIONS

Solakoglu et al., "Late-term reconstruction of lateral ankle ligaments using a split peroneus brevis tendon graft (Colville's technique) in patients with chronic lateral instability of the ankle", International Orthopaedics (SICOT) (2003) 27, pp. 223-227, DOI 10.1007/s00264-003-0468-03.

Thomopoulos et al., "The localized expression of extracellular matrix components in healing tendon insertion sites: an in situ hybridization study", Journal of Orthopaedic Research (2002) pp. 454-463.

Weiler et al., "Tendon Healing in a Bone Tunnel. Part I: Biomechanical Results After Biodegradable Interference Fit Fixation in a Model of Anterior Cruciate Ligament Reconstruction in Sheep", Arthroscopy: The Journal of Arthroscopic and Related Surgery, vol. 18, No. 2 Feb. 2002, pp. 113-123.

Yang et al., "Tendon and Ligament Regeneration and Repair: Clinical Relevance and Developmental Program", Birth Defects Res C Embryo Today, Sep. 2013, 99(3), pp. 203-222, doi:10.1002/bdrc.21041, available in PMC Jun. 2, 2014, pp. 1-35.

\* cited by examiner

IMPLANT COMPRISING FIRST AND SECOND SETS OF PILLARS FOR ATTACHING A TENDON OR A LIGAMENT TO A HARD TISSUE

FIELD OF THE INVENTION

The invention relates to implants for attaching a tendon or a ligament to a hard tissue, and more particularly to implants for attaching a tendon or a ligament to a hard tissue that comprise a shaft, a first surface of the shaft, a second surface of the shaft, first pillars for contacting a hard tissue, first slots to be occupied by the hard tissue, second pillars for contacting a tendon or a ligament, and second slots to be occupied by the tendon or the ligament.

BACKGROUND OF THE INVENTION

Tendons are bands of dense fibrous connective tissue that attach muscle to bone. Ligaments are bands of fibrous tissue that bind joints together and connect articular bones and cartilages to facilitate movement.

It is estimated that about 300,000 tendon and ligament repair surgeries are performed in the United States each year (Yang et al. (2013), Birth Defects Res C Embryo Today, 99:203-222). Common repair surgeries include rotator cuff repair, patellar tendon repair, and anterior cruciate ligament reconstruction. Unfortunately, tendon and ligament reattachment surgeries often fail due to failure of regeneration of enthesis, corresponding to a specialized transitional tissue that connects tendon and ligament to bone by a gradual change in structure, composition, and mechanical behavior, thereby effectively transferring stress from tendon and ligament to bone and vice versa despite the tendon and ligament being compliant and the bone being stiff (Liu et al. (2010), Journal of Orthopaedic Surgery and Research, 5:59).

Entheses occur in two types. The first type, direct insertions, also termed fibrocartilaginous entheses, are composed of four zones: tendon or ligament, uncalcified fibrocartilage, calcified fibrocartilage, and bone. Tendon and ligament fibers are passed directly into bone cortex in small surface areas of the bone, including deep fibers attached to bone at right angles or tangentially. Examples include anterior cruciate ligament, Achilles tendon, patellar tendon, rotator cuff, and femoral insertion of medial collateral ligament. The second type, indirect insertions, also termed fibrous entheses, has no fibrocartilaginous interface. For indirect insertions, the tendon or ligament passes along the bone surface obliquely, inserts into the bone periosteum, and connects over larger surface areas of the bone than for direct insertions. Examples include tibial insertion of the medial collateral ligament and insertion of the deltoid tendon into the humerus.

Conventional approaches for surgical reattachment of tendons and ligaments to bones involve performing tendon or ligament grafts. In some approaches, a tendon or ligament, typically obtained from another part of a patient, is attached to an implant or a bone plug and inserted into a bone tunnel, with suturing to secure the graft to the bone. In some approaches, a tendon is passed through holes in a bone, and then an interference screw is inserted, forcing the tendon against bone to fix the tendon in place. In some approaches, a ligament is looped through holes in a bone, without use of an implant, a bone plug, or an interference screw.

Following tendon and ligament reattachment surgeries, tendon/ligament and bone healing occurs through formation of fibrovascular scar tissue, not reestablishment of enthesis (Apostolakos et al (2014), Muscles Ligaments and Tendons Journal, 4:333-342). This apparently contributes to failures of the surgeries.

Conventional hard-tissue implants include implants designed to promote ingrowth of hard tissue based on forming a tissue/implant interface in which the implant forms a continuous phase and the tissue forms a discontinuous phase, e.g. based on the implant having a concave and/or porous surface into which the hard tissue can grow, and designed to have add-on surface modifications, e.g. modifications added based on sintering.

For example, Van Kampen et al., U.S. Pat. No. 4,608,052, discloses an implant for use in a human body having an integral attachment surface adapted to permit ingrowth of living tissue. The implant surface is defined by a multiplicity of adjacent, generally concave surface parts having intersecting, generally aligned rims defining an inner attachment surface portion and by a multiplicity of spaced posts projecting from the inner attachment surface. Van Kampen also discloses that implants have been provided with porous surfaces, as described in U.S. Pat. Nos. 3,605,123, 3,808,606, and 3,855,638.

Also for example, J. D. Bobyn et al, 150 Clinical Orthopaedics & Related Research 263 (1980), discloses that a pore size range of approximately 50 to 400 μm provided an optimal or maximal fixation strength (17 MPa) in the shortest time period (8 weeks) with regard to cobalt-base alloy implants with powder-made porous surfaces. Specifically, implants were fabricated based on coating cylindrical rods of cast cobalt-base alloy with cobalt base alloy powder in four particle size ranges. The particle size ranges were as follows: 25 to 45 μm; 45 to 150 μm; 150 to 300 μm; and 300 to 840 μm. The corresponding pore size ranges of the particles were as follows: 20 to 50 μm; 50 to 200 μm; 200 to 400 μm; and 400 to 800 μm, respectively. The particles were then bonded to the rods based on sintering. All implants were manufactured to have a maximal diameter of 4.5 mm and a length of 9.0 mm. The implants were surgically inserted into holes in dog femurs and bone ingrowth was allowed to proceed. After varying periods of time (4, 8, or 12 weeks), the maximum force required to dislodge the implants was determined. Implants with a pore size lower than 50 μm yielded relatively low fixation strengths at all time points, while implants with a pore size higher than 400 μm exhibited relatively high scatter with regard to fixation strengths, thus indicating that a pore size range of approximately 50 to 400 μm provided an optimal or maximal fixation strength.

Conventional hard-tissue implants also include implants having surface texturing, e.g. raised portions and indented portions, barbs, and/or pillars, to promote an interference fit between the implants and adjacent bone, to make it difficult to withdraw the implants from hard tissue, or to more effectively mechanically anchor at an early date or affix into adjoining hard tissue.

For example, Tuke et al., U.K. Pat. Appl. No. GB2181354A, discloses an orthopedic implant having at least one surface area, integral with the adjacent portion of the implant and adapted in use to contact bone. The surface area has a finely patterned conformation composed of a plurality of raised portions separated from each other by indented portions. The indented portions are of a width and depth to allow bone penetration thereinto in use to promote an interference fit between the implant and adjacent bone in the region of the patterned area.

Also for example, Amrich et al., U.S. Pat. No. 7,018,418, discloses implants having a textured surface with microrecesses such that the outer surface overhangs the microrecesses. In one embodiment, unidirectional barbs are produced in the surface that can be inserted into bone or tissue. The directional orientation of the barbs is intended to make it difficult to withdraw from the bone or tissue.

Also for example, Picha, U.S. Pat. No. 7,556,648, discloses a spinal implant, i.e. an implant for use in fusing and stabilizing adjoining spinal vertebrae, including a hollow, generally tubular shell having an exterior lateral surface, a leading end, and a trailing end. The exterior surface includes a plurality of pillars arranged in a non-helical array. Each pillar has a height of 100 to 4,500 μm and a lateral dimension at the widest point of 100 to 4,500 μm. The exterior surface also has a plurality of holes therethrough to permit bone ingrowth therethrough.

Unfortunately, interfaces of hard tissue and hard-tissue implants in which the hard tissue is in a discontinuous phase may be susceptible to stress shielding, resulting in resorption of affected hard tissue, e.g. bone resorption, over time. Also, addition of surface texturing to implants by sintering can result in the surface texturing occupying an excessive volume of corresponding hard tissue/implant interfaces, leaving insufficient space for hard tissue. In addition, spinal implants are designed to perform under conditions relevant to spine, i.e. compression, rotational shear, and vertical shear, with the compression being essentially constant, the rotational shear being intermittent, and the vertical shear being rare, rather than conditions relevant to other hard tissues such as long bone, maxillary bone, mandibular bone, and membranous bone, i.e. load bearing conditions, including compression and tension, varying across the hard tissue and across time, and intermittent rotational and vertical shear.

Picha et al., U.S. Pat. No. 8,771,354, discloses hard-tissue implants including a bulk implant, a face, pillars, and slots. The hard-tissue implant has a Young's modulus of elasticity of at least 10 GPa, has a ratio of (i) the sum of the volumes of the slots to (ii) the sum of the volumes of the pillars and the volumes of the slots of 0.40:1 to 0.90:1, does not comprise any part that is hollow, and does not comprise any non-pillar part extending to or beyond the distal ends of any of the pillars. The hard-tissue implants can provide immediate load transfer upon implantation and prevent stress shielding over time, thus promoting hard-tissue remodeling and growth at the site of implantation. The interface can have a continuous phase corresponding to the hard tissue and a discontinuous phase corresponding to the hard-tissue implant.

A need exists for implants for attachment of a tendon or a ligament to a hard tissue that account for tendon/ligament and bone healing occurring through formation of fibrovascular scar tissue, to effectively transfer stress from tendon and ligament to bone and vice versa despite the tendon and ligament being compliant and the bone being stiff.

BRIEF SUMMARY OF THE INVENTION

An implant for attaching a tendon or a ligament to a hard tissue is provided. The implant comprises:

(a) a shaft having a top end and a bottom end, the shaft extending between the top end and the bottom end;

(b) a first surface of the shaft extending from the top end to the bottom end and having a cross section transverse to the shaft that is convex;

(c) a second surface of the shaft extending from the top end to the bottom end and having a cross section transverse to the shaft that is flat or concave;

(d) first pillars for contacting a hard tissue, the first pillars being distributed on the first surface across an area of at least 50 mm², and extending distally therefrom, and each first pillar being integral to the shaft, having a distal end, having a transverse area of (100×100) to (2,000×2,000) μm², and having a height of 100 to 2,000 μm;

(e) first slots to be occupied by the hard tissue, the first slots being defined by the first pillars and each first slot having a width of 100 to 2,000 μm as measured along the shortest distance between adjacent first pillars;

(f) second pillars for contacting a tendon or a ligament, the second pillars being distributed on the second surface across an area of at least 50 mm², and extending distally therefrom, and each second pillar being integral to the shaft, having a distal end, having a transverse area of (200×200) to (4,000×4,000) μm², and having a height of 100 to 10,000 μm; and (g) second slots to be occupied by the tendon or the ligament, the second slots being defined by the second pillars and each second slot having a width of 400 to 4,000 μm as measured along the shortest distance between adjacent second pillars.

The implant has (1) a Young's modulus of elasticity of at least 3 GPa, (2) a ratio of (i) the sum of the volumes of the first slots to (ii) the sum of the volumes of the first pillars and the volumes of the first slots ("first surface ratio") of 0.40:1 to 0.90:1, and (3) a ratio of (i) the sum of the volumes of the second slots to (ii) the sum of the volumes of the second pillars and the volumes of the second slots ("second surface ratio") of 0.60:1 to 0.98:1.

The second surface ratio is greater than the first surface ratio.

In some embodiments, the implant is made of one or more materials selected from implantable-grade polyaryletherketone that is essentially unfilled, implantable-grade polyetheretherketone, implantable-grade polyetherketoneketone, titanium, stainless steel, cobalt-chromium alloy, titanium alloy, Ti-6Al-4V titanium alloy, Ti-6Al-7Nb titanium alloy, ceramic material, silicon nitride (Si3N4), implantable-grade composite material, implantable-grade polyaryletherketone with filler, implantable-grade polyetheretherketone with filler, implantable-grade polyetheretherketone with carbon fiber, or implantable-grade polyetheretherketone with hydroxyapatite. Also, in some embodiments, the implant is made of one or more hard tissues selected from human hard tissue, animal hard tissue, autologous hard tissue, allogenic hard tissue, xenogeneic hard tissue, human cartilage, animal cartilage, human bone, animal bone, cadaver bone, or cortical allograft. Also, in some embodiments, the implant is made of one or more materials selected from resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic.

In some embodiments, the shaft is straight.

In some embodiments, the shaft is tapered toward the bottom end.

In some embodiments, the shaft has a top end aperture located at the top end of the shaft.

In some embodiments, the second surface of the shaft has a cross section transverse to the shaft that is flat. Also, in some embodiments, the second surface of the shaft has a cross section transverse to the shaft that is concave.

In some embodiments, the first pillars extend in a uniform direction. Also, in some embodiments, the first pillars are perpendicular to the first surface of the shaft. Also, in some embodiments, the first pillars are angled toward the top end.

In some embodiments, the second pillars extend in a uniform direction. Also, in some embodiments, the second pillars extend distally at an identical angle with respect to a plane bisecting the shaft. Also, in some embodiments, the second pillars are angled toward the bottom end.

In some embodiments, the transverse area of each first pillar is (250×250) µm² to (1,000×1,000)µm².

In some embodiments, the height of each first pillar is 200 to 900 µm.

In some embodiments, one or more of the first pillars have dimensions that differ from those of other first pillars, such that the transverse areas and/or heights, and thus volumes, of the one or more first pillars differ from those of the other first pillars.

In some embodiments, the width of each first slot is 200 to 1,000 µm.

In some embodiments, the transverse area of each second pillar is (400×400) µm² to (2,000×2,000)µm².

In some embodiments, the height of each second pillar is 100 to 8,000 µm.

In some embodiments, one or more of the second pillars have dimensions that differ from those of other second pillars, such that the transverse areas and/or heights, and thus volumes, of the one or more second pillars differ from those of the other second pillars.

In some embodiments, the width of each second slot is 500 to 3,000 µm.

In some embodiments, the shaft has a shaft diameter at a widest portion of the shaft and a shaft length from the top end to the bottom end, and the implant has a ratio of the shaft length to the shaft diameter of 2.0 to 10.

In some embodiments, the shaft has a shaft diameter of 4 to 20 mm at a widest portion of the shaft.

In some embodiments, the shaft has a shaft length of 8 to 40 mm from the top end to the bottom end.

In some embodiments, one or more of the shaft, the first pillars, or the second pillars are non-porous. Also, in some embodiments, one or more of the shaft, the first pillars, or the second pillars are porous.

In some embodiments, the implant further comprises a tool-engaging portion.

In some embodiments, the implant has one or more holes in the shaft. In some of these embodiments, the second pillars are distributed centrally along the shaft, from near the top end to near the bottom end, and a plurality of the holes are distributed peripherally along the shaft, from near the top end to near the bottom end. Also in some of these embodiments, the one or more holes are located at or near the bottom end of the shaft.

In some embodiments, the implant further comprises a central slot extending axially within the shaft and a hinge extending axially along the shaft.

In some embodiments, the implant further comprises a cap attached to the shaft at the bottom end of the shaft. In some of these embodiments, the cap is attached to shaft by a hinge.

Also provided is a method of use of the implant for attaching a tendon or a ligament to a hard tissue in an individual in need thereof. The method comprises steps of:

(1) preparing a bone tunnel in the bone of the individual;
(2) attaching a tendon or a ligament to the implant such that the tendon or ligament is in contact with the second pillars of the implant; and
(3) inserting the implant into the bone tunnel.

The method results in attaching the tendon or the ligament to the bone of the individual.

In some embodiments, the preparing of the bone tunnel comprises drilling a hole in the bone.

In some embodiments, the implant has an implant diameter between distal ends of pillars at a widest portion of the shaft, and the preparing of the bone tunnel comprises preparing a hole in the bone that has a hole diameter that is smaller than the implant diameter.

In some embodiments, the attaching of the tendon or the ligament to the implant comprises piercing the tendon or the ligament with the second pillars, thereby putting the tendon or ligament in contact with the second pillars of the implant.

In some embodiments, the inserting of the implant into the bone tunnel comprises driving the implant into the bone tunnel by rotating the implant. Also, in some embodiments, the inserting of the implant into the bone tunnel comprises pressing the implant into the bone tunnel.

In some embodiments, the implant further comprises a central slot extending axially within the shaft and a hinge extending axially along the shaft, the method further comprising, after steps (1) to (3), a step of (4) pushing a wedge into the central slot, thereby opening the hinge and expanding the implant.

In some embodiments, the method does not comprise use of a suture or an adhesive to secure the tendon or the ligament to the implant.

Also provided is an implant assembly for attaching a tendon or a ligament to a hard tissue. The implant assembly comprises first and second implants, as described above, and a cap, also as described above. The cap is attached to the shaft of the first implant at the bottom end of the shaft. The second implant is attached to the first implant along the shaft of the first implant and faces the second surface of the shaft of the first implant.

Also provided is an implant assembly for attaching a tendon or a ligament to a hard tissue. The implant assembly comprises an implant, as described above, a cap, also as described above, and a mesh part. The cap is attached to the shaft of the implant at the bottom end of the shaft. The mesh part is attached to the implant along the shaft of the implant and faces the second surface of the shaft of the implant.

BRIEF DESCRIPTION OF THE DRAWINGS

These and other features, aspects, and advantages of the present disclosure are better understood when the following detailed description is read with reference to the accompanying drawings, in which.

DETAILED DESCRIPTION

Figure 1:
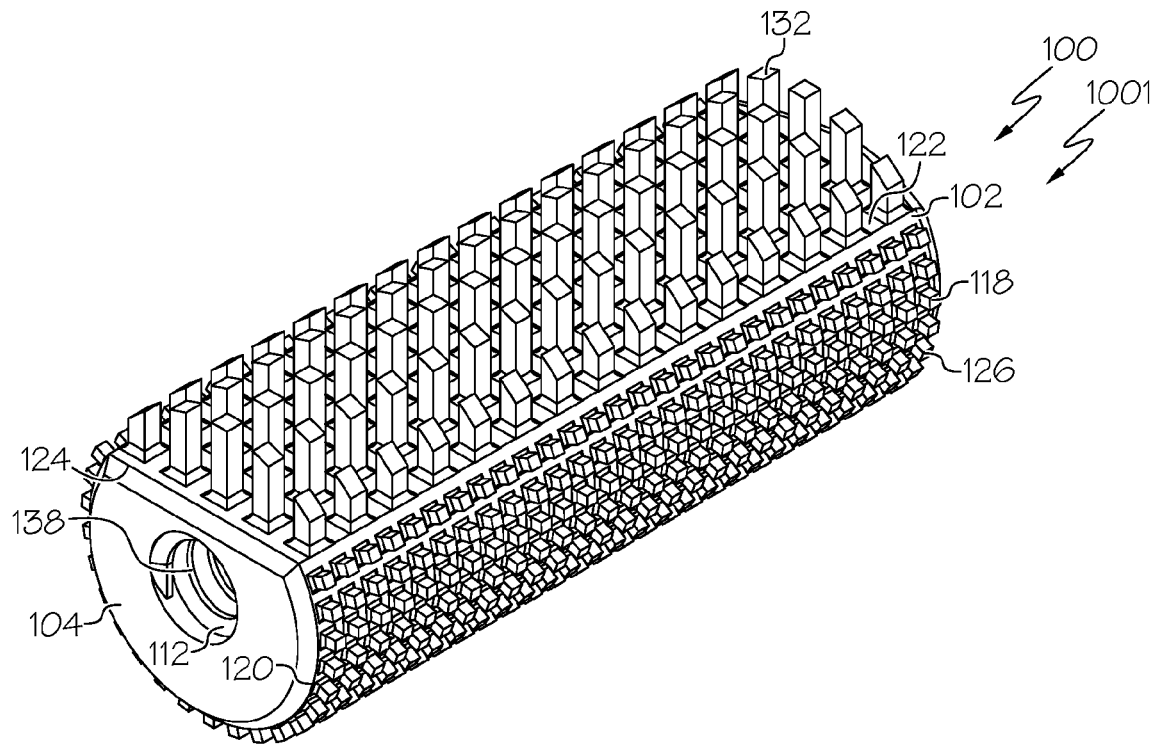
FIG. 1 is a first perspective view of a first embodiment of an implant for attaching a tendon or a ligament to a hard tissue as disclosed herein.
Figure 2:
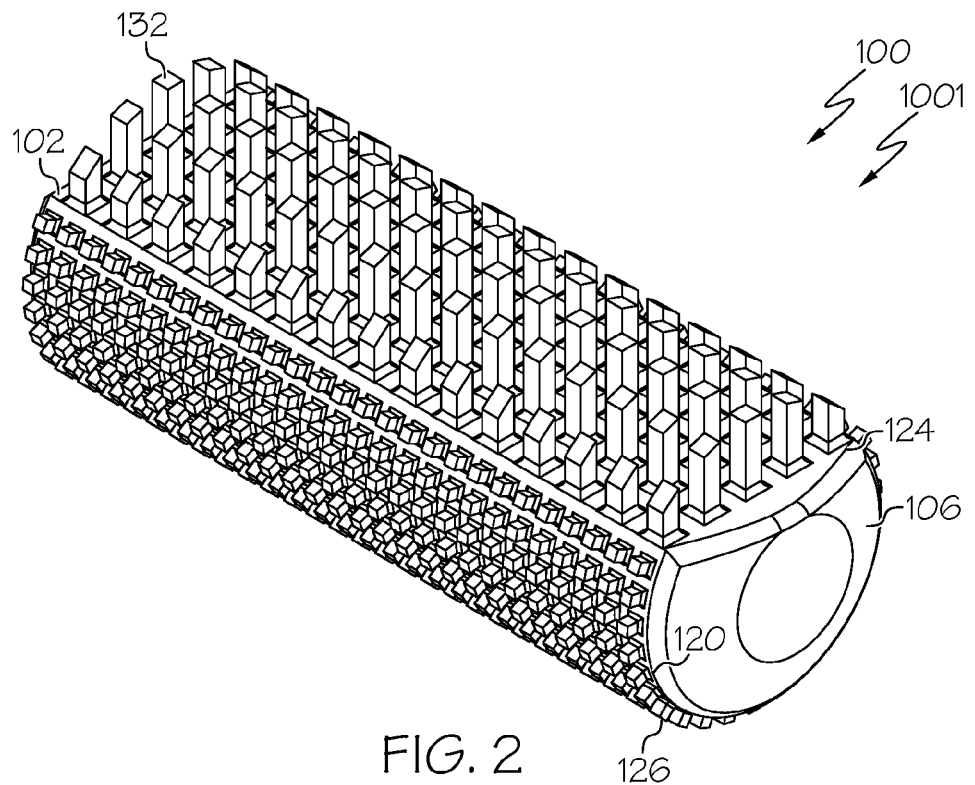
FIG. 2 is a second perspective view of the implant of FIG. 1.
Figure 3:
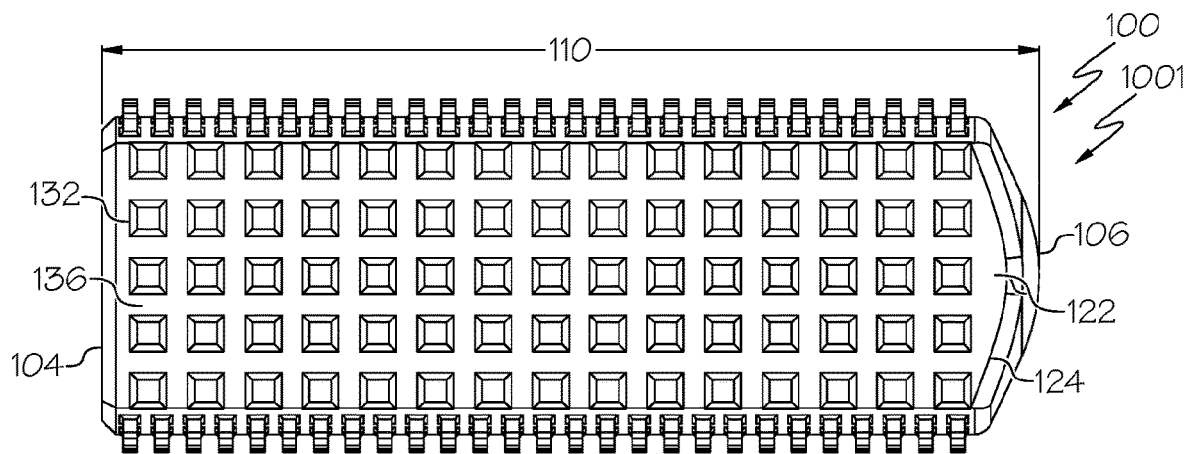
FIG. 3 is a first side view of the implant of FIG. 1.
Figure 4:
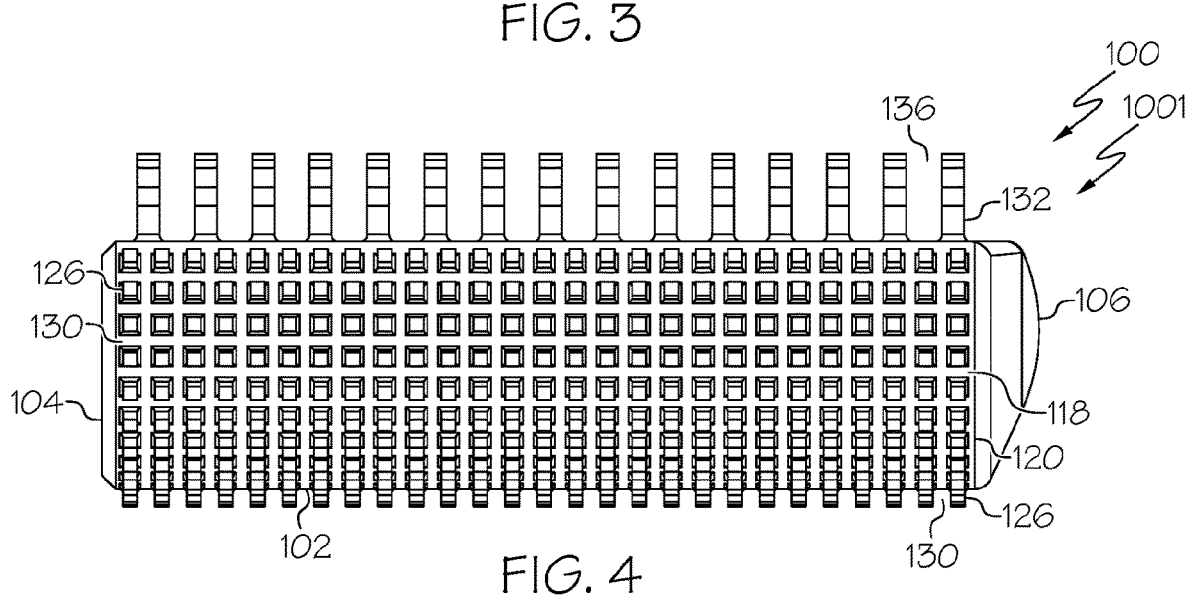
FIG. 4 is a second side view of the implant of FIG. 1.
Figure 5:
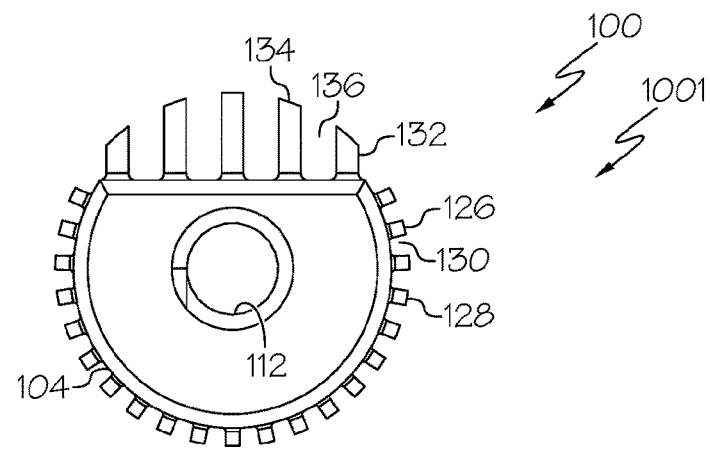
FIG. 5 is a top view of the implant of FIG. 1.
Figure 6:
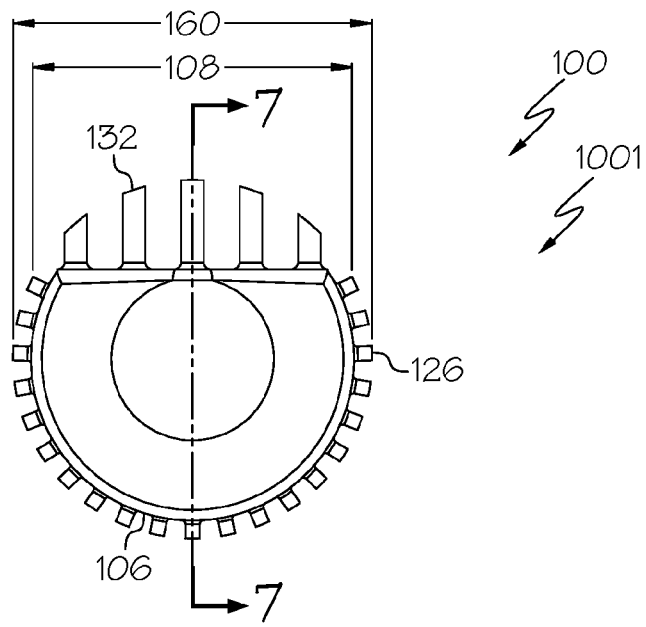
FIG. 6 is a bottom view of the implant of FIG. 1.

As set forth in the figures, example implants for attaching a tendon or a ligament to a hard tissue are provided. The implants provide advantages, including for example that the implant can provide a surface for attachment of a tendon or ligament, protect the tendon or ligament upon placement of the implant in a hard tissue, promote hard-tissue remodeling and growth of the hard tissue at the site of implantation, and hold the tendon or ligament stable following implantation to allow formation of a fibrovascular scar tissue that can effectively transfer stress from tendon or ligament to bone and vice versa. Without wishing to be bound by theory, it is believed that the resulting interfaces of the implant, the tendon or ligament, and the hard tissue can withstand substantial yield/elongation and load before failure.

This is because the implants provide an interface with a hard tissue at the first surface of the shaft that can have a continuous phase corresponding to the hard tissue and a discontinuous phase corresponding to the implant. The hard tissue can also make up at least 40% of the volume of the interface, and the product of the Young's modulus of elasticity of the hard tissue and the volume of the tissue and the product of the Young's modulus of elasticity of the implant and the volume of the first pillars of the implant can be well matched. Thus, the interface can exhibit mechanical properties similar to those of the bulk hard tissue adjacent to the interface. Also, the first pillars may be pressed into the hard tissue, potentially eliminating micro-motion and migration of the implant over time, accommodating torque, and/or eliminating the need for adhesives such as cement or grout to hold the implant in place. In addition, the implants may promote rich vascularization of the hard tissue of the interface, enhancing wound healing, providing nutritional support, accelerating healing, remodeling, and integration of the hard tissue, and limiting the potential for infection of the hard tissue. Rapid or immediate integration of the hard tissue into the space between the first pillars of the implant may also prevent detrimental cellular reactions at the interface, such as formation of fibrous tissue, seroma, or thrombosis.

This also is because the implants provide an interface with the tendon or ligament at the second surface of the shaft that allows for attachment of the tendon or ligament to the implant, for example based on piercing of the tendon or ligament by the second pillars in discrete areas of limited size. The tendon or ligament also can make up at least 60% of the volume of the interface, minimizing damage to cell structure of the tendon or ligament between the second pillars, while the second pillars protect the tendon or ligament from damage upon implantation of the implant in the hard tissue and hold the tendon or ligament stable following implantation. In addition, the combination of rich vascularization of adjacent hard tissue and stability of the tendon or ligament may allow formation of a fibrovascular scar tissue that can effectively transfer stress from tendon or ligament to bone and vice versa.

As used herein, the term "implant for attaching a tendon or a ligament to a hard tissue" means an implant suitable for attaching a tendon or a ligament to a hard tissue based on implantation in a hard tissue. Exemplary hard tissues suitable for implantation of the implants include bones such as humerus, e.g. for rotator cuff repair, patella or tibial tubercle, e.g. for patellar tendon repair, and femur and tibia, e.g. for anterior cruciate ligament reconstruction, among other bones.

As used herein, the term "pillar" means a projection that extends distally from a surface of an implant, that is not in direct physical contact with any other pillars or other parts of the implant other than the surface, and that is for contacting a hard tissue or a tendon or ligament. Because a pillar is not in direct physical contact with any other pillars or other parts of the implant other than the surface, upon implantation no pillar forms a continuous phase within the resulting interface of the hard tissue, tendon, or ligament and the implant.

A pillar can have a transverse area, i.e. an area of a cross-section taken relative to a vertical axis along which the pillar extends distally from the surface of the implant, of, for example, (i) (100 µm×100 µm) to (2,000 µm×2,000 µm), i.e. $1.0 \times 10^4$ µm$^2$ to $4.0 \times 10^6$ µm$^2$, (ii) (200 µm×200 µm) to (1,000 µm×1,000 µm), i.e. $4.0 \times 10^4$ µm$^2$ to $1.0 \times 10^6$ µm$^2$, (iii) (250 µm×250 µm) to (1,000 µm×1,000 µm), i.e. $6.3 \times 10^4$ µm$^2$ to $1.0 \times 10^6$ µm$^2$, (iv) (300 µm×300 µm) to (500 µm×500 µm), i.e. $9 \times 10^4$ µm$^2$ to $2.5 \times 10^5$ µm$^2$, (v) (350 µm×350 µm) to (450 µm×450 µm), i.e. $1.2 \times 10^5$ µm$^2$ to $2.0 \times 10^5$ µm$^2$, or (vi) (395 µm×395 µm) to (405 µm×405 µm), i.e. $1.6 \times 10^5$ µm$^2$. A pillar also can have a transverse area of, for example, (i) (200 µm×200 µm) to (4,000 µm×4,000 µm), i.e. $4.0 \times 10^4$ µm$^2$ to $1.6 \times 10^7$ µm$^2$, (ii) (400 µm×400 µm) to (2,000 µm×2,000 µm), i.e. $1.6 \times 10^5$ µm$^2$ to $4.0 \times 10^6$ µm$^2$, or (iii) (1,000 µm×1,000 µm) to (2,000 µm×2,000 µm), i.e. $1.0 \times 10^6$ µm$^2$ to $4.0 \times 10^6$ µm$^2$. Of note, the expression of transverse areas of pillars as squares of linear dimensions, e.g. (100 µm×100 µm), here and throughout this application, is for purposes of convenience only and is not intended to limit any pillars so described to square shapes, square transverse areas, or square cross-sections.

A pillar can have a pillar height, i.e. the height of the pillar from a surface of the implant to the distal end of the pillar, of, for example, 100 to 2,000 µm, 200 to 900 µm, 300 to 800 µm, or 400 to 600 µm. A pillar also can have a height of, for example, 100 to 10,000 µm, 100 to 8,000 µm, 100 to 7,000 µm, 100 to 6,000 µm, or 100 to 5,000 µm.

A pillar can have a volume, i.e. product of pillar transverse area and pillar height, of, for example (100 µm×100 µm×100 µm) to (2,000 µm×2,000 µm×2,000 µm), i.e. $1.0 \times 10^6$ µm$^3$ to $8 \times 10^9$ µm$^3$, among other volumes. A pillar also can have a volume of, for example (200 µm×200 µm×100 µm) to (4,000 µm×4,000 µm×10,000 µm), i.e. $4.0 \times 10^6$ µm$^3$ to $1.6 \times 10^{11}$ µm$^3$, among other volumes.

A pillar can have, as seen from a top view, a square shape, a rectangular shape, a herringbone shape, a circular shape, or an oval shape, respectively, or alternatively can have other polygonal, curvilinear, or variable shapes.

As used herein, the term "slot" means the spaces between the pillars. Accordingly, the pillars define the slots. The slots can have a slot height as defined by the pillars, of, for example, 100 to 2,000 µm, 200 to 900 µm, 300 to 800 µm, or 400 to 600 µm, or 100 to 10,000 µm, 100 to 8,000 µm, 100 to 7,000 µm, 100 to 6,000 µm, or 100 to 5,000 µm, among others. The slots can have a slot width as measured along the shortest distance between adjacent pillars of, for example, 100 to 2,000 µm, 150 to 1,000 µm, 200 to 700 µm, or 300 to 500 µm, or 400 to 4,000 µm, 500 to 3,000 µm, 600 to 2,000 µm, or 800 to 1,500 µm, among others. The slots have a volume corresponding to the volume of the space between the pillars.

As used herein, the term "pore" refers to a void space of less than 1,000 µm in size, i.e. having a diameter of less than 1,000 µm, on or below a surface, e.g. the surface of an implant. Pores can occur in a material naturally, e.g. based on a natural porosity of the material, or can be introduced, e.g. by chemical or physical treatment. Pores can be continuous with respect to each other, based on being interconnected with each other below a surface, or pores can be discontinuous, based on not being interconnected with each other below a surface. Pores can be sufficiently large to allow for migration and proliferation of osteoblasts and mesenchymal cells. Accordingly, for example, a porous surface is a surface that includes void spaces of less than 1,000 µm in size in the surface, whereas a non-porous surface is a surface that does not include such a void space.

As used herein, the term "interface" includes the product of implantation wherein the first pillars of the implant are contacting a hard tissue and the first slots of the implant are occupied, partially or completely, by the hard tissue. The term "interface" also includes the product of implantation wherein the second pillars of the implant are contacting a tendon or a ligament and the second slots of the implant are occupied, partially or completely, by the tendon or the ligament.

In some examples, e.g. immediately after implanting the implant with at least some penetration of the first pillars into the hard tissue and/or after at least some remodeling and growth of the hard tissue to partially fill in space between the implant and the hard tissue, the first pillars are contacting the hard tissue (e.g. at distal ends of the first pillars), and the first slots are partially occupied by the hard tissue. In other examples, e.g. immediately after implanting the implant with extensive penetration of the first pillars into the hard-tissue and/or after extensive remodeling and growth of the hard tissue to fill in all space between the implant and the hard tissue, the first pillars are contacting the hard tissue (e.g. at distal ends and lateral surfaces of the first pillars), and the first slots are completely occupied by the hard tissue. In other examples the first pillars contact the hard tissue over time, based on remodeling and growth of hard tissue in and around the first pillars, e.g. during healing.

As used herein, the term "continuous," when used for example in reference to the hard-tissue of an interface, means that the hard tissue forms a single continuous phase, extending throughout and across the interface to each boundary of the interface. As used herein, the term "discontinuous," when used for example in reference to the implant of an interface, means that the implant does not form such a single continuous phase.

Implant for Attaching a Tendon or a Ligament to a Hard Tissue

Considering the features of the implant for attaching a tendon or a ligament to a hard tissue in more detail, FIGS. 1-7 illustrate a first embodiment 1001 of an implant 100 for attaching a tendon or a ligament to a hard tissue.

The implant 100 can be made from a material having a Young's modulus of elasticity, i.e. a tensile modulus of elasticity, of at least 3 GPa, as measured at 21° C. The implant 100 can be made, for example, from one or more materials such as implantable-grade polyaryletherketone that is essentially unfilled (such as implantable-grade polyetheretherketone or implantable-grade polyetherketoneketone), titanium, stainless steel, cobalt-chromium alloy, titanium alloy (such as Ti-6Al-4V titanium alloy or Ti-6Al-7Nb titanium alloy), ceramic material (such as silicon nitride (Si3N4)), or implantable-grade composite material (such as implantable-grade polyaryletherketone with filler, implantable-grade polyetheretherketone with filler, implantable-grade polyetheretherketone with carbon fiber, or implantable-grade polyetheretherketone with hydroxyapatite). Specific examples include (i) implantable-grade polyetheretherketone that is essentially unfilled, which has a Young's modulus of approximately 4 GPa, (ii) implantable-grade polyetheretherketone with filler, e.g. carbon-fiber-reinforced implantable-grade polyetheretherketone, which has a Young's modulus of elasticity of at least 18 GPa, (iii) titanium, which has a Young's modulus of elasticity of approximately 110 GPa, (iv) stainless steel, which has a Young's modulus of elasticity of approximately 200 GPa, (v) cobalt-chromium alloy, which has a Young's modulus of elasticity of greater than 200 GPa, or (vi) titanium alloy, which has a Young's modulus of elasticity of approximately 105-120 GPa, all as measured at 21° C. The implant 100 also can be made, for example, from one or more hard tissues such as a hard tissue obtained from a human or animal (such as autologous hard tissue, allogenic hard tissue, or xenogeneic hard tissue), human cartilage, animal cartilage, human bone, animal bone, cadaver bone, or cortical allograft. Such hard tissues obtained from a human or animal can have a Young's modulus of elasticity of, e.g. 4 to 18 GPa. Such hard tissues obtained from a human or animal can also be treated, in advance of implantation, to decrease or eliminate the capacity of the hard tissue to elicit an immune response in an individual upon implantation into the individual. The implant 100 also can be made, for example, from one or more materials such as resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic. The implant 100 also can be made, for example, from one or more materials that are resorbable, such as polylactic acid or polycaprolactone, among others, in which case callus around bone and tendon at the site of implantation would gradually remove the polymer of the implant 100, with replacement by a patient's own tissue, which would be more analogous to a natural state. The implant 100 also can be made from further combinations of the above-noted materials and/or hard tissues. Accordingly, the implant 100 has a Young's modulus of elasticity of at least 3 GPa, for example 18 to 230 GPa, 18 to 25 GPa, 100 to 110 GPa, 190 to 210 GPa, 200 to 230 GPa, 105 to 120 GPa, or 4 to 18 GPa.

As shown in FIGS. 1-7, the implant 100 comprises a shaft 102 having a top end 104 and a bottom end 106. The shaft 102 extends between the top end 104 and the bottom 106.

The shaft 102 forms the core of the implant 100 and can have a generally cylindrical shape, although other shapes, e.g. conical shapes, or frustoconical shapes, may be used in further examples. In some examples the shaft 102 has a shaft diameter 108 at a widest portion of the shaft and a shaft length 110 from the top end 104 to the bottom end 106, and the implant 100 has a ratio of the shaft length 110 to the shaft diameter 108 of 2.0 to 10. In some examples the shaft 102 has a shaft diameter 108 of 4 to 20 mm at a widest portion of the shaft 102. In some examples the shaft 102 has a shaft length 110 of 8 to 40 mm from the top end 104 to the bottom end 106.

The shaft 102 can be made from one or more of the materials or hard tissues noted above with respect to the implant 100, e.g. one or more materials such as implantable-grade polyaryletherketone that is essentially unfilled (such as implantable-grade polyetheretherketone or implantable-grade polyetherketoneketone), titanium, stainless steel, cobalt-chromium alloy, titanium alloy (such as Ti-6Al-4V titanium alloy or Ti-6Al-7Nb titanium alloy), ceramic material (such as silicon nitride (Si3N4)), or implantable-grade composite material (such as implantable-grade polyaryletherketone with filler, implantable-grade polyetheretherketone with filler, implantable-grade polyetheretherketone with carbon fiber, or implantable-grade polyetheretherketone with hydroxyapatite), or e.g. one or more hard tissues such as a hard tissue obtained from a human or animal (such as autologous hard tissue, allogenic hard tissue, or xenogeneic hard tissue), human cartilage, animal cartilage, human bone, animal bone, cadaver bone, or cortical allograft, or e.g. one or more materials such as resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic, or e.g. one or more materials that are resorbable, such as polylactic acid or polycaprolactone.

The shaft 102 can be porous or non-porous. For example, the shaft 102 can include one or more surfaces that are porous, and/or can be made from one or more materials that are porous. Such porous surfaces can include pores having diameters of, e.g. 1 to 900 μm, 100 to 800 μm, or 200 to 600 μm. Also for example, the shaft 102 can include only surfaces that are non-porous, and/or can be made only from one or more materials that are non-porous.

As shown in FIGS. 1-7, in some examples the shaft 102 is straight. This can simplify achieving a complementary fit between the implant 100 and a hard tissue during implantation of the implant 100, e.g. into a bone tunnel of a bone. Also in some examples the shaft 102 is tapered toward the bottom end 106. This can minimize resistance between the implant 100 and a hard tissue during implantation, e.g. again into a bone tunnel of a bone. In some of these examples the implant 100 may be expanded following implantation, e.g. by insertion of a wedge into the implant 100, as discussed below. Also in some examples the shaft 102 is tapered toward the top end 104. Following implantation, an implant 100 tapered this way can resist pull-out.

As shown in FIG. 1 and FIGS. 5-7, in some examples the shaft 102 has a top end aperture 112 located at the top end 104 of the shaft 102. In some of these examples the shaft 102 has an internal passage 114 extending axially with respect to the shaft 102, from the top end aperture 112. In some examples the internal passage 114 extends through the shaft 102, from the top end aperture 112, and ends within the shaft 102. Accordingly, in some examples the implant 100 includes a blind hole. Also, in some examples the internal passage 114 extends through the shaft 102, from the top end aperture 112, to a bottom end aperture 116 located at the bottom end 106 of the shaft 102. Accordingly, in some examples the implant 100 is cannulated. The cannula can have a diameter of, for example, 1 to 3 mm diameter. These features can facilitate implantation of the implant 100 into a site for implantation in a hard tissue, e.g. into a bone tunnel of a bone, for example by providing a complementary fit between the implant 100 and the site for implantation, allowing easy insertion of the implant 100, and allowing use of a tool and/or guidewire for guiding the implant 100 during insertion.

As shown in FIGS. 1-7, the implant 100 also comprises a first surface 118 of the shaft 102 extending from the top end 104 to the bottom end 106 and having a cross section transverse to the shaft that is convex. The first surface 118 is an exterior surface of the shaft 102.

The first surface 118 can be defined by an edge 120. For example, the edge 120 can be a single continuous edge that defines the first surface 118. Also for example, the edge 120 can be two edges that are discontinuous with respect to each other that together define the first surface 118. The edge 120 can be sharp, although other rounded, angular, smooth, and/or irregular edges may be used in further examples.

The first surface 118 can be porous, e.g. including pores having diameters of, e.g. 1 to 900 µm, 100 to 800 µm, or 200 to 600 µm, or the first surface 118 can be non-porous.

As shown in FIGS. 1-7, the implant 100 also comprises a second surface 122 of the shaft 102 extending from the top end 104 to the bottom end 106 and having a cross section transverse to the shaft 102 that is flat or concave. In some examples the second surface 122 of the shaft 102 has a cross section transverse to the shaft 102 that is flat. In some examples the second surface 122 of the shaft 102 has a cross section transverse to the shaft 102 that is concave. Like the first surface 118, the second surface 122 can be defined by an edge 124, e.g. a single continuous edge, or two edges that are discontinuous with respect to each other. Also, the edge 124 can be sharp, although other rounded, angular, smooth, and/or irregular edges may be used in further examples.

As shown in FIGS. 1-7, the implant 100 also comprises first pillars 126 for contacting a hard tissue. The hard tissue can be selected from, for example, bones such as humerus, patella, tibia, or femur, among other hard tissues. In some examples the first pillars 126 may contact a hard tissue immediately upon implantation, e.g. based on extending distally from the first surface 118 of the shaft 102. In some examples the first pillars 126 may contact a hard tissue over time after implantation, e.g. based on remodeling and growth of a hard tissue to come in contact with first pillars 126 over time after implantation.

The first pillars 126 are distributed on the first surface 118 across an area of at least 50 mm$^2$. For example, the first pillars 126 can be distributed in a regular pattern on the first surface 118, across the area of the first surface 118. In this regard, the first pillars 126 can be distributed in even rows along the first surface 118, and can be distributed along a given row uniformly with respect to the distances between the centers of the first pillars 126 in the row. Also for example, the first pillars 126 can also be distributed in other regular patterns, e.g. the first pillars 126 can be distributed in rows that are even, but without the first pillars 126 being distributed uniformly within rows, the first pillars 126 in one row may be offset from the first pillars 126 in adjacent rows, the first pillars 126 may be arranged in a spiral pattern, etc. Also for example, the first pillars 126 can be distributed on the first surface 118 in irregular patterns or randomly. For example, the first pillars 126 can be distributed on the first surface 118 such that the first pillars 126 are packed more densely on one area of the first surface 118 and less densely on another area of the first surface 118. Moreover, for a shaft 102 including more than first surface 118 across which first pillars 126 are distributed, the first pillars 126 can be distributed differently on the various first surfaces 118, e.g. in different regular patterns, in different irregular patterns, and/or packed at different densities.

The first pillars 126 can be distributed on the first surface 118 of the shaft 102 such that none of the first pillars 126 are located at an edge 120, i.e. the first surface 118 can have a peripheral border that is not occupied by any first pillars 126, resulting in the area of the first surface 118 across which the first pillars 126 are distributed being less than the total area of the first surface 118. In other examples the first pillars 126 can be distributed on the first surface 118 such that at least some of the first pillars 126 are located at an edge 120, e.g. the area of the first surface 118 across which the first pillars 126 are distributed can be equal to the total area of the first surface 118.

The first pillars 126 extend distally from the first surface 118. In some examples all first pillars 126 extend in a uniform direction. In some examples all first pillars 126 extend distally at the same angle with respect to the first surface 118. Also for example, some first pillars 126 may extend distally at a different angle and/or in a different direction relative to other first pillars 126. In some examples the first pillars 126 extend perpendicularly from the first surface 118. This can simplify manufacturing of the implant 100. In some examples the first pillars 126 are angled toward the top end 104 of the shaft 102. This can increase stability of the implant 100 following implantation in a hard tissue, e.g. an implant 100 including first pillars 126 angled this way can resist pull-out. In some examples the first pillars 126 extend from the first surface 118 at other angles and/or varying angles.

Each first pillar 126 is integral to the shaft 102, i.e. the first pillars 126 and the shaft 102 are made from the same starting material, rather than, for example, the first pillars 126 being an add-on to the shaft 102. Like the shaft 102, the first pillars 126 can be porous, e.g. including pores having diameters of, e.g. 1 to 900 µm, 100 to 800 µm, or 200 to 600 µm, or the first pillars 126 can be non-porous.

Each first pillar 126 has a distal end 128, corresponding to the distal-most portion of the first pillar 126 relative to the first surface 118 of the shaft 102. Each first pillar 126 can have distal edges, corresponding to edges defining the distal end 128 of each first pillar 126. Each first pillar 126 can also have lateral edges, corresponding to edges of the lateral sides of each first pillar 126. The distal edges and/or the lateral edges can be sharp, although other rounded, angular, smooth, and/or irregular edges may be used in further examples. The distal ends 128 can be flat, slanted, curved, or pointed, among other contours.

With respect to dimensions of the first pillars 126, each first pillar 126 has a transverse area, i.e. an area of a cross-section taken relative to the vertical axis along which the first pillar 126 extends distally from the first surface 118, of (100×100) to (2,000×2,000) µm$^2$. Each first pillar 126 can have a transverse area of, for example, (200 µm×200 µm) to (1,000 µm×1,000 µm), (250 µm×250 µm) to (1,000 µm×1,000 µm), (300 µm×300 µm) to (500 µm×500 µm), (350 µm×350 µm) to (450 µm×450 µm), or (395 µm×395 µm) to (405 µm×405 µm). Each first pillar 126 has a pillar height, i.e. the height of the first pillar 126 from the first surface 118 of the shaft 102 to the distal end 128 of the first pillar 126, of 100 to 2,000 µm. Each first pillar 126 can have a pillar height of, for example, 200 to 900 µm, 300 to 800 µm, or 400 to 600 µm. Each first pillar 126 has a volume, i.e. product of pillar transverse area and pillar height, of, for example (100 µm×100 µm×100 µm) to (2,000 µm×2,000 µm×2,000 µm), i.e. $1.0 \times 10^6$ µm$^3$ to $8 \times 10^9$ µm$^3$, among other volumes. The first pillars 126 extending from the first surface 118 can, for example, all have identical dimensions, e.g. identical pillar transverse areas, pillars heights, and thus identical individual volumes. Alternatively, one or more first pillars 126 can have dimensions that differ from those of other first pillars 126, such that the pillar transverse areas and/or pillar heights, and thus volumes, of the one or more first pillars 126 differ from those of the other first pillars 126.

The first pillars 126 can have, as seen from a top view, a square shape, a rectangular shape, a herringbone shape, a circular shape, or an oval shape, or alternatively can have other polygonal, curvilinear, or variable shapes. In some examples all first pillars 126 can have the same shape, e.g. a square shape, a rectangular shape, a herringbone shape, a circular shape, or an oval shape, as seen from a top view. In some examples not all first pillars 126 have the same shape as seen from a top view.

As shown in FIGS. 1-7, the implant 100 also comprises first slots 130 to be occupied by the hard tissue. For example, upon implantation of the implant 100 into a hard tissue, the hard tissue can immediately occupy all or part of the space corresponding to the first slots 130. This can be accomplished, for example, by pressing the implant 100 into the hard tissue. Moreover, to the extent that the hard tissue does not, upon implantation, immediately occupy all of the space corresponding to first slots 130, the hard tissue can eventually occupy all or part of the space corresponding to the first slots 130 based on remodeling and/or growth of the hard tissue over time, e.g. during healing.

The first slots 130 are defined by the first pillars 126, i.e. the first slots 130 are the spaces between the first pillars 126. Accordingly, the first slots 130 have a slot height as defined by the first pillars 126, of, for example, 100 to 2,000 µm, 200 to 900 µm, 300 to 800 µm, or 400 to 600 µm. Each first slot 130 has a width of 100 to 2,000 µm as measured along the shortest distance between adjacent first pillars 126. The first slot width can be, for example, 150 to 1,000 µm, 200 to 700 µm, or 300 to 500 µm. The first slots 130 have a volume corresponding to the volume of the space between the first pillars 126.

As shown in FIGS. 1-7, the implant 100 also comprises second pillars 132 for contacting a tendon or a ligament. The tendon or the ligament can be selected from among any tendon or ligament suitable for use as a tendon graft or a ligament graft. In some examples the second pillars 132 may contact a tendon or a ligament based on piercing the tendon or the ligament with the second pillars 132 prior to implantation of the implant 100, such that the tendon or the ligament becomes attached to the second pillars 132 and fixed in place with respect to the implant 100. In some examples the second pillars 132 may contact a tendon or a ligament based on pressing the tendon or the ligament against the second pillars 132, and the tendon or the ligament may be attached to the second pillars 132 indirectly, e.g. by use of a suture to fix the tendon or ligament in place with respect to the implant 100.

The second pillars 132 are distributed on the second surface 122 across an area of at least 50 mm$^2$. The second pillars 132 can be distributed on the second surface 122 as described above regarding distribution of the first pillars 126 on the first surface 118, e.g. in a regular pattern, in even rows, in other regular patterns, or in irregular patterns or randomly. For example, the second pillars 132 can be distributed on the second surface 122 such that the second pillars 132 are packed more densely on one area of the second surface 122, e.g. near the bottom end 106 of the shaft 102, and less densely on another area of the second surface 122, e.g. near the top end 104 of the shaft 102. This may be advantageous for securing the tendon or ligament to the implant 100 sufficiently while minimizing piercing of the tendon or ligament by the second pillars 132 and thus minimizing potential trauma to the tendon or ligament associated with the piercing. Thus, in some examples the second pillars 132 are distributed entirely within an area of the second surface 122 that is near the bottom end 106 of the shaft 102, e.g. the 50%, 40%, 30%, or 20% of the area of the second surface 122 that is closest to the bottom end 106 of the shaft 102. Also like for the first pillars 126, some of the second pillars 132 can be located at an edge 124, or not.

The second pillars 132 extend distally from the second surface 122. In some examples all second pillars 132 extend in a uniform direction. In some examples all second pillars 132 extend distally at an identical angle with respect to a plane bisecting the shaft 102. Also for example, some second pillars 132 may extend distally at a different angle and/or in a different direction relative to other second pillars 132. In some examples the second pillars 132 extend perpendicularly from a plane bisecting the shaft 102. This can simplify manufacturing of the implant 100. In some examples the second pillars 132 are angled toward the bottom end 106 of the shaft 102. This can increase stability of a tendon or a ligament attached to the implant 100 following implantation in a hard tissue, e.g. by decreasing the risk of separation of the tendon or the ligament from the implant 100. In some examples the second pillars 132 extend from the second surface 122 at other angles and/or varying angles.

Like each first pillar 126, each second pillar is integral to the shaft 102, i.e. the second pillars 132 and the shaft 102 are made from the same starting material, rather than, for example, the second pillars 132 being an add-on to the shaft 102. Like the shaft 102, the second pillars 132 can be porous, e.g. including pores having diameters of, e.g. 1 to 900 µm, 100 to 800 µm, or 200 to 600 µm, or the second pillars 132 can be non-porous.

Also like each first pillar 126, each second pillar 132 has a distal end 134, corresponding to the distal-most portion of the second pillar 132 relative to the second surface 122 of the shaft 102. Each second pillar 132 can have distal edges, corresponding to edges defining the distal end 134 of each second pillar 132. Each second pillar 132 can also have lateral edges, corresponding to edges of the lateral sides of each second pillar 132. The distal edges and/or the lateral edges can be sharp, although other rounded, angular, smooth, and/or irregular edges may be used in further examples. The distal ends 134 can be flat, slanted, curved, or pointed, among other contours.

With respect to dimensions of the second pillars 132, each second pillar 132 has a transverse area, i.e. an area of a cross-section taken relative to the vertical axis along which the second pillar 132 extends distally from the second surface 122, of (200×200) to (4,000×4,000). Each second pillar 132 can have a transverse area of, for example, (400 µm×400 µm) to (2,000 µm×2,000 µm), or (1,000 µm×1,000 µm) to (2,000 µm×2,000 µm). Each second pillar 132 has a pillar height, i.e. the height of the second pillar 132 from the second surface 122 of the shaft 102 to the distal end 134 of the second pillar 132, of 100 to 10,000 µm. Each second pillar 132 can have a pillar height of, for example, 100 to 8,000 µm, 100 to 7,000 µm, 100 to 6,000 µm, or 100 to 5,000 µm. Each second pillar 132 has a volume, i.e. product of pillar transverse area and pillar height, of, for example (200 µm×200 µm×100 µm) to (4,000 µm×4,000 µm×10,000 µm), i.e. $4.0 \times 10^6$ µm$^3$ to $1.6 \times 10^{11}$ µm$^3$, among other volumes. The second pillars 132 extending from the second surface 122 can, for example, all have identical dimensions, e.g. identical pillar transverse areas, pillars heights, and thus identical individual volumes. Alternatively, one or more second pillars 132 can have dimensions that differ from those of other second pillars 132, such that the pillar transverse areas and/or pillar heights, and thus volumes, of the one or more second pillars 132 differ from those of the other second pillars 132.

Like the first pillars 126, the second pillars 132 can have, as seen from a top view, a square shape, a rectangular shape, a herringbone shape, a circular shape, or an oval shape, or alternatively can have other polygonal, curvilinear, or variable shapes.

As shown in FIGS. 1-7, the implant 100 also comprises second slots 136 to be occupied by the tendon or the ligament. For example, upon the second pillars 132 contacting the tendon or the ligament, the tendon or the ligament can occupy most or all of the space corresponding to the second slots 136. This can be accomplished, for example, by matching the width of the tendon or the implant to a width of the second surface 122 of the shaft 102, such that the tendon or the ligaments fits on or across the second pillars 132 and within the second slots 136.

The second slots 136 are defined by the second pillars 132, similarly as the first slots 130 are defined by the first pillars 126. Accordingly, the second slots 136 have a slot height as defined by the second pillars 132, of, for example, 100 to 10,000 µm, 100 to 8,000 µm, 100 to 7,000 µm, 100 to 6,000 µm, or 100 to 5,000 µm. Each second slot 136 has a width of 400 to 4,000 µm as measured along the shortest distance between adjacent second pillars 132. The second slot width can be, for example, 500 to 3,000 µm, 600 to 2,000 µm, or 800 to 1,500 µm. The second slots 136 have a volume corresponding to the volume of the space between the second pillars 132.

The implant 100 has a ratio of (i) the sum of the volumes of the first slots 130 to (ii) the sum of the volumes of the first pillars 126 and the volumes of the first slots 130 ("first surface ratio") of 0.40:1 to 0.90:1. The first surface ratio can be, for example, 0.51:1 to 0.90:1, 0.51:1 to 0.60:1, or 0.70:1 to 0.76:1.

The implant 100 also has a ratio of (i) the sum of the volumes of the second slots 136 to (ii) the sum of the volumes of the second pillars 132 and the volumes of the second slots 136 ("second surface ratio") of 0.60:1 to 0.98:1. The second surface ratio can be, for example, 0.71:1 to 0.98:1, 0.75:1 to 0.97:1, 0.80:1 to 0.96:1, 0.80:1 to 0.90:1, 0.85:1 to 0.95:1, about 0.80:1, about 0.85:1, about 0.90:1, or about 0.95:1.

The second surface ratio is greater than the first surface ratio.

Without wishing to be bound by theory, it is believed that the first surface ratio determines the approximate percentages of hard tissue and implant 100 that will occupy a first surface interface following implantation of the implant 100, e.g. that upon inserting the implant 100 into the hard tissue, or upon remodeling and growth of the hard-tissue following implantation, that the hard tissue will occupy all or essentially all of the space corresponding to the first slots 130 of the implant 100. The first surface interface includes (i) the first pillars 126, (ii) the first slots 130, which, upon or following implantation, become occupied by hard tissue, (iii) any additional space between the first surface 118 and a curved surface defined by the distal ends 128 of the first pillars 126, e.g. the space between a peripheral border of the first surface 118 that is not occupied by first pillars 126 and the curved surface, which also becomes occupied by hard tissue, and (iv) any pores on the first surface 118 or the first pillars 126, which, depending on their size, may also become occupied by hard tissue. Accordingly, for example, a first surface ratio of 0.40:1 would, following implantation of an implant 100 and subsequent remodeling and growth of hard tissue, wherein the implant 100 includes an edge 120 around the first surface 118 and for which first pillars 126 are located at the edge 120, result in an interface that includes by volume 40% hard tissue and 60% implant 100, and more particularly 60% first pillars 126 of the implant 100. Similarly, a first surface ratio of 0.40:1 would, following implantation of an implant 100 and subsequent remodeling and growth of hard tissue, wherein the implant 100 includes an edge 120 around the first surface 118 and for which no first pillars 126 are located at the edge 120, result in an interface that includes by volume more than 40% hard tissue and less than 60% implant 100, with the percentage of hard tissue increasing, and the percentage of implant 100 decreasing, with increasing distance between the peripheral-most first pillars 126 and first slots 130 and the edge 120 around the first surface 118. By way of further examples, first surface ratios of 0.51:1, 0.60:1, 0.70:1, 0.76:1, and 0.90:1, would result in first surface interfaces that include, by volume, 51% hard tissue and 49% implant 100, 60% hard tissue and 40% implant 100, 70% hard tissue and 30% implant 100, 76% hard tissue and 24% implant 100, and 90% hard tissue and 10% implant, respectively, for an implant 100 wherein the implant 100 includes an edge 120 around the first surface 118 and for which first pillars 126 are located at the edge 120. Moreover, the percentage of hard tissue would increase, and the percentage of implant 100 would decrease, with increasing distance between the peripheral-most first pillars 126 and first slots 130 and the edge 120 of the first surface 118. It is believed that by achieving a first surface interface that is at least 40% hard tissue, but that has a sufficient amount of the implant 100 to provide support and to keep the implant 100 from migrating, the first surface interface will exhibit properties similar to those of the bulk hard tissue adjacent to the interface, e.g. high resilience to load.

Without wishing to be bound by theory, it also is believed that the second surface ratio determines the approximate percentages of tendon or ligament and implant 100 that will occupy a second surface interface following implantation of the implant 100, e.g. that upon attaching the tendon or the ligament to the implant 100 such that the tendon or the ligament is in contact with the second pillars 132, and upon inserting the implant 100 into the hard tissue, that the tendon or the ligament will occupy all or essentially all of the space corresponding to the second slots 136 of the implant 100. The second surface interface includes (i) the second pillars 132, (ii) the second slots 136, which, upon attachment of the tendon or ligament, become occupied by the tendon or ligament, (iii) any additional space between the second surface 122 and a curved surface defined by the distal ends 134 of the second pillars 132, e.g. the space between a peripheral border of the second surface 122 that is not occupied by second pillars 132 and the curved surface, which also becomes occupied by the tendon or ligament, and (iv) any pores on the second surface 122 or the second pillars 132, which, depending on their size, may also become occupied by the tendon or ligament. It is believed that use of an implant 100 for which the second surface ratio is greater than the first surface ratio will provide a sufficient surface for attachment of a tendon or ligament, corresponding to the second surface 122 including the second pillars 132, e.g. based on piercing of the tendon or ligament by the second pillars 132 in a discrete area of limited size, while protecting the tendon or ligament upon placement of the implant 100 in a hard tissue, by minimizing further trauma to the tendon or ligament during implantation, e.g. the tendon or ligament can be attached to the implant 100 such that most or all of the tendon or ligament fits between the second surface 122 and the distal ends 134 of the second pillars 132, such that the tendon or ligament is subject to little or no contact with hard tissue during insertion of the implant 100 into the hard tissue and no screw or other fixation device is subsequently driven through the tendon or ligament following the insertion. It is believed that this will promote hard-tissue remodeling and growth of the hard tissue at the site of implantation, and hold the tendon or ligament stable following implantation to allow formation of a fibrovascular scar tissue between the hard tissue and the tendon or ligament that can effectively transfer stress from tendon or ligament to bone and vice versa.

Figure 7:
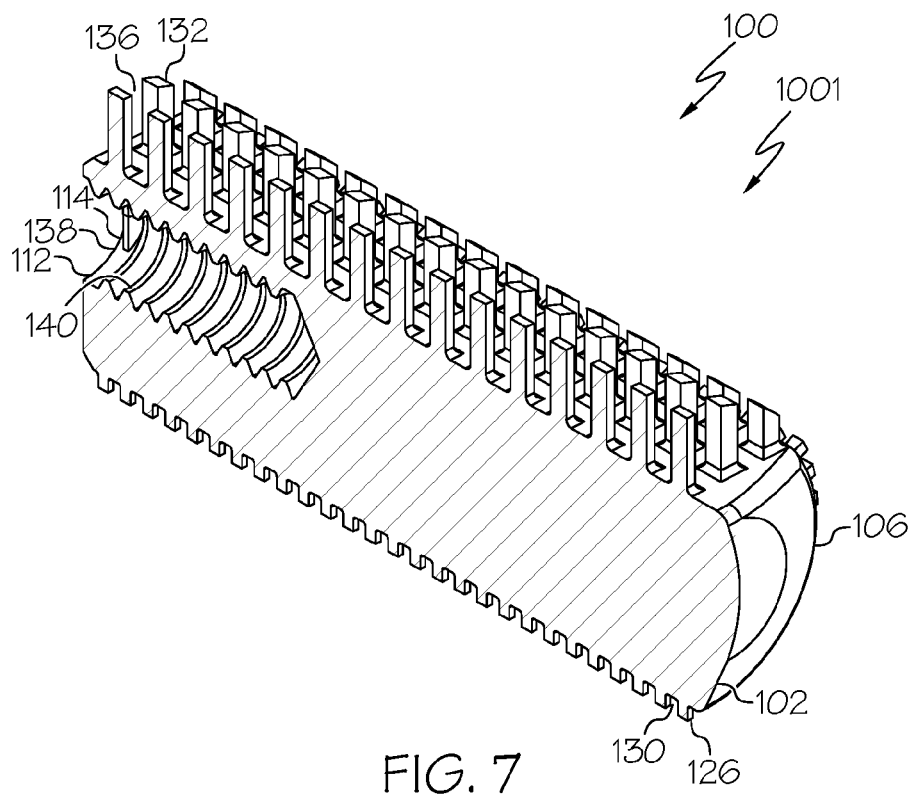
FIG. 7 is a sectional view of the implant of FIG. 6.
Figure 8:
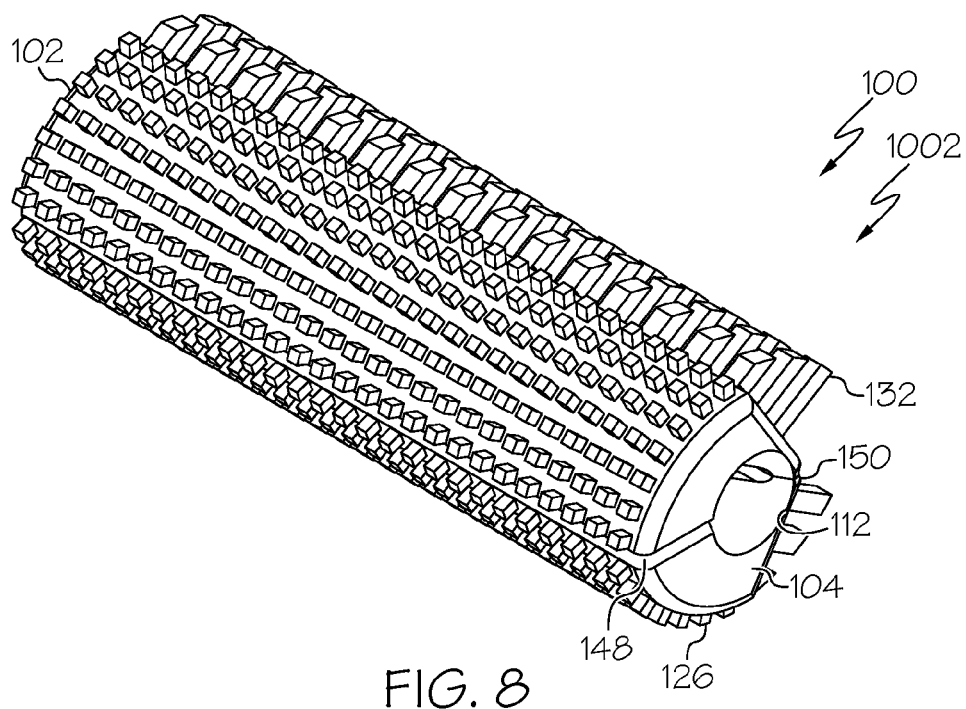
FIG. 8 is a first perspective view of a second embodiment of an implant for attaching a tendon or a ligament to a hard tissue as disclosed herein.
Figure 9:
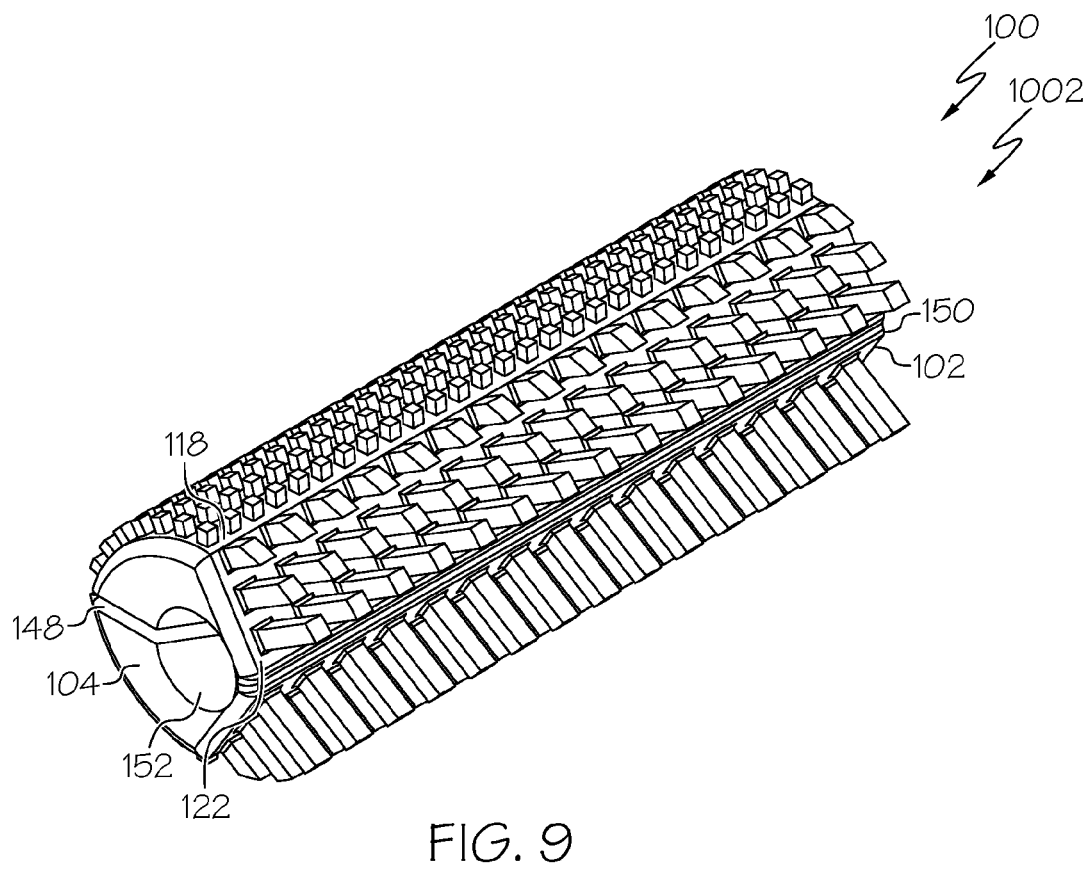
FIG. 9 is a second perspective view of the implant of FIG. 8.
Figure 10:
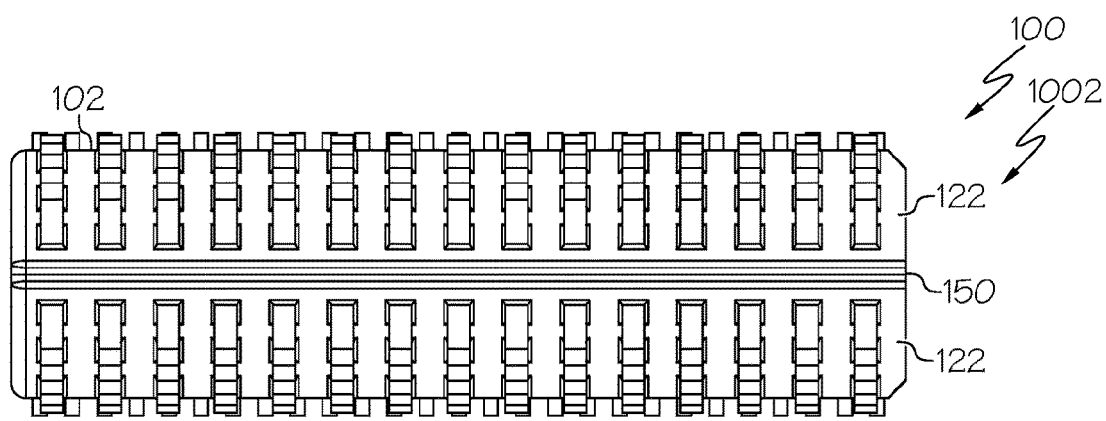
FIG. 10 is a first side view of the implant of FIG. 8.
Figure 11:
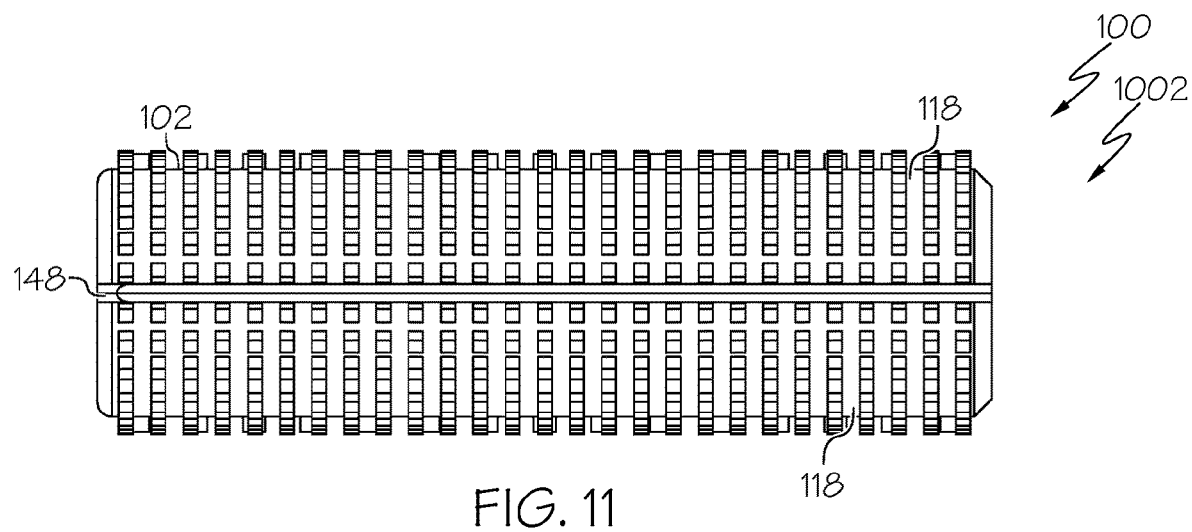
FIG. 11 is a second side view of the implant of FIG. 8.
Figure 12:
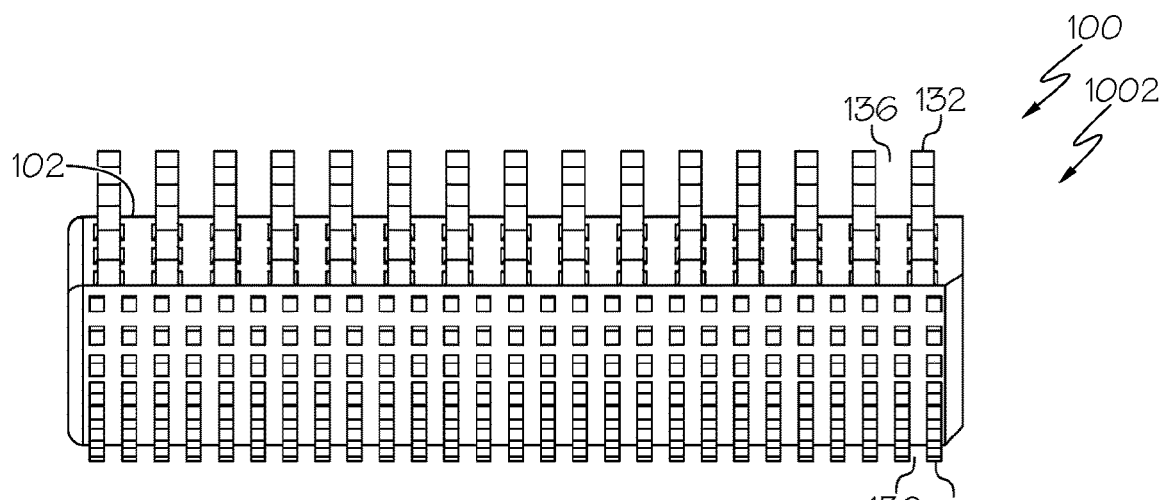
FIG. 12 is a third side view of the implant of FIG. 8.
Figure 13:
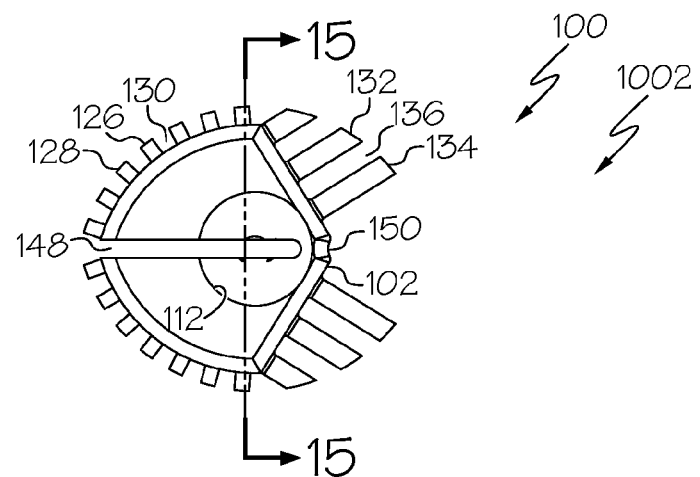
FIG. 13 is a top view of the implant of FIG. 8.
Figure 14:
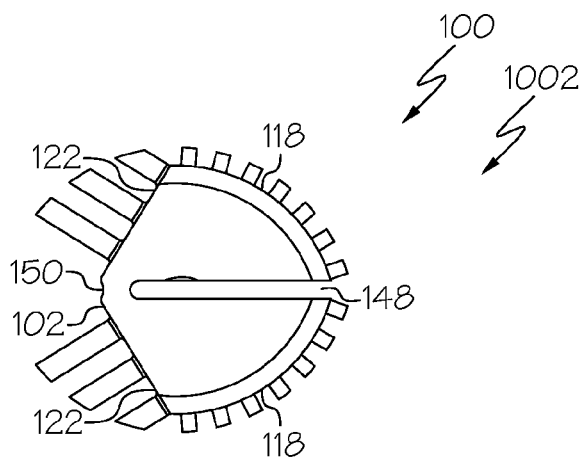
FIG. 14 is a bottom view of the implant of FIG. 8.
Figure 15:
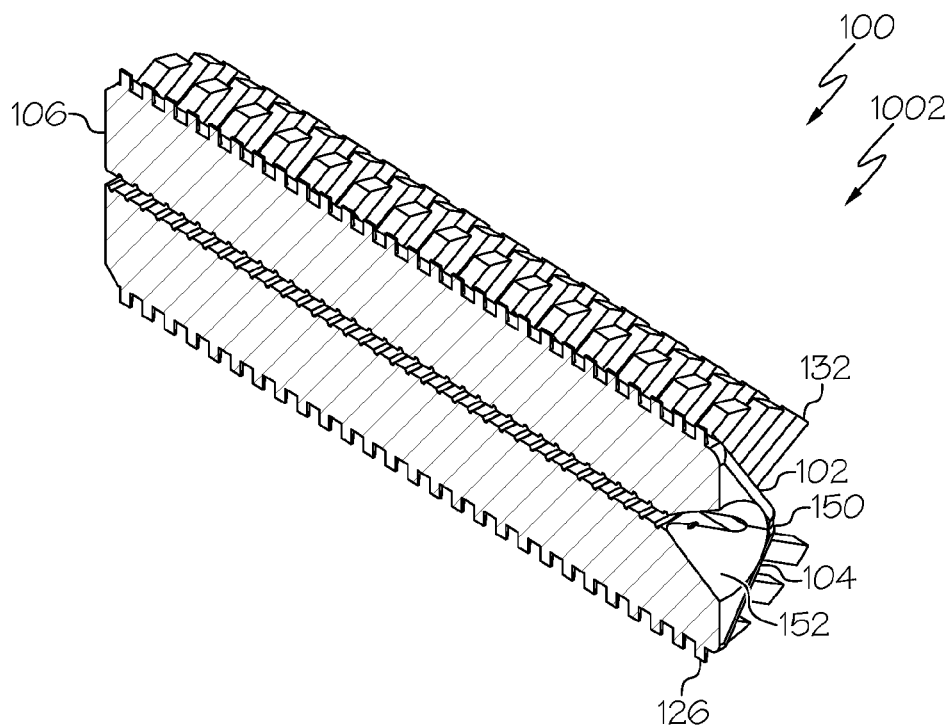
FIG. 15 is a sectional view of the implant of FIG. 13.
Figure 16:
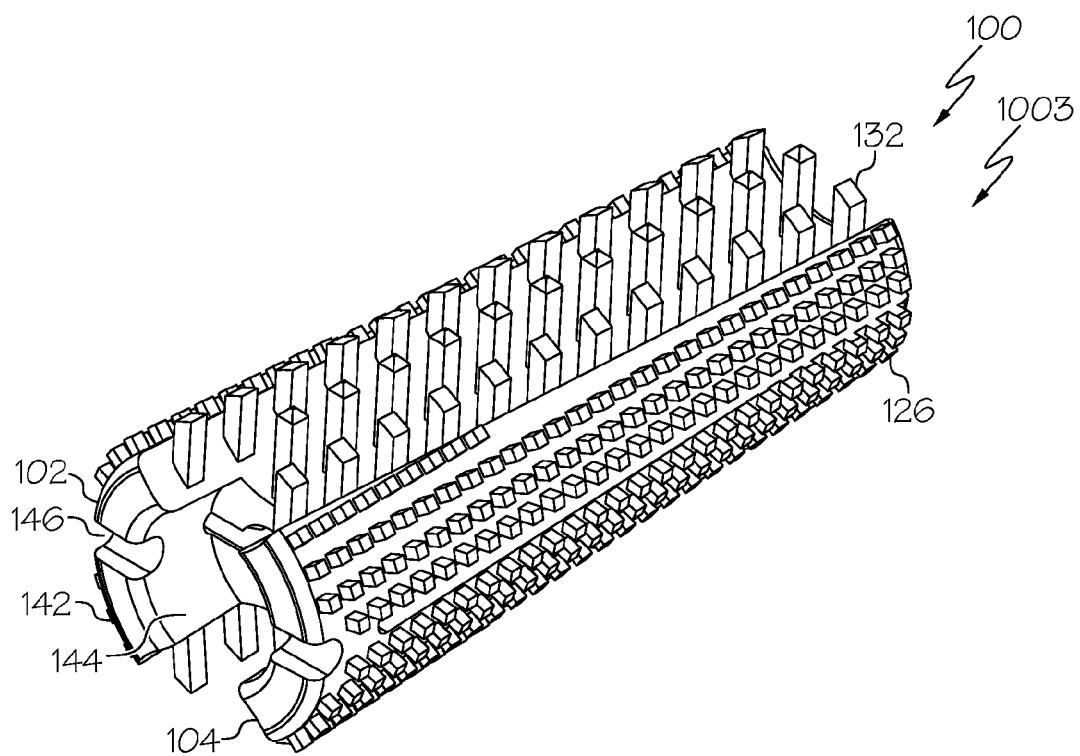
FIG. 16 is a first perspective view of a third embodiment of an implant for attaching a tendon or a ligament to a hard tissue as disclosed herein.
Figure 17:
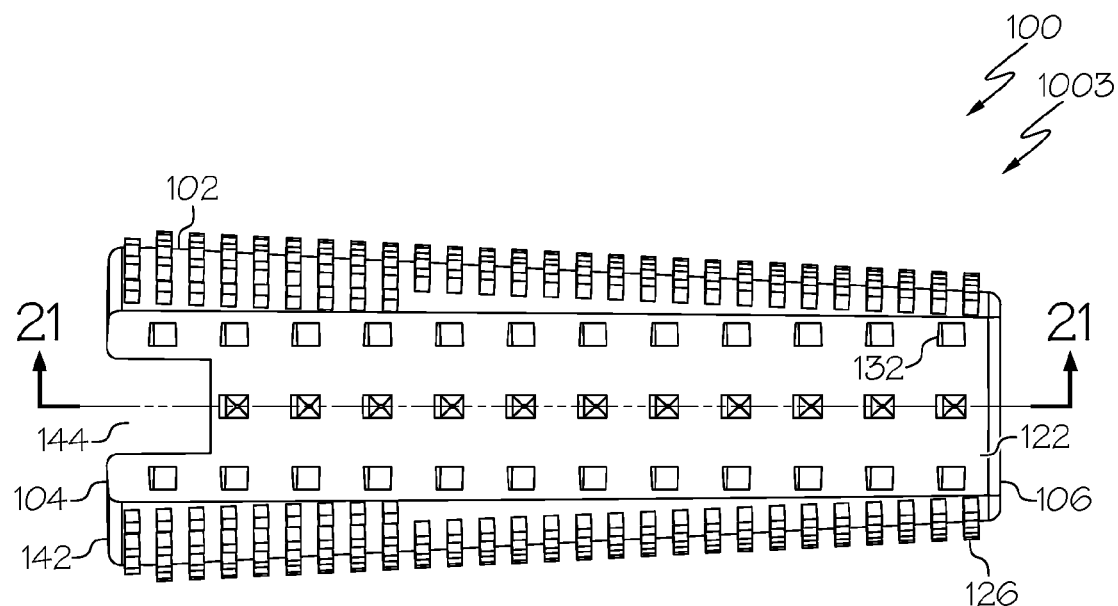
FIG. 17 is a first side view of the implant of FIG. 16.
Figure 18:
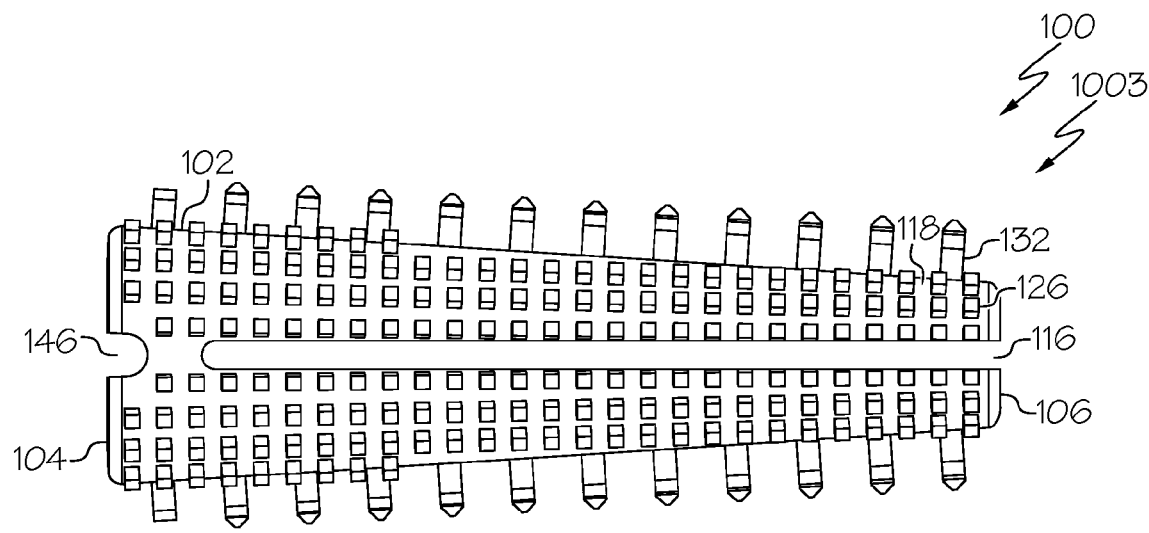
FIG. 18 is a second side view of the implant of FIG. 16.
Figure 19:
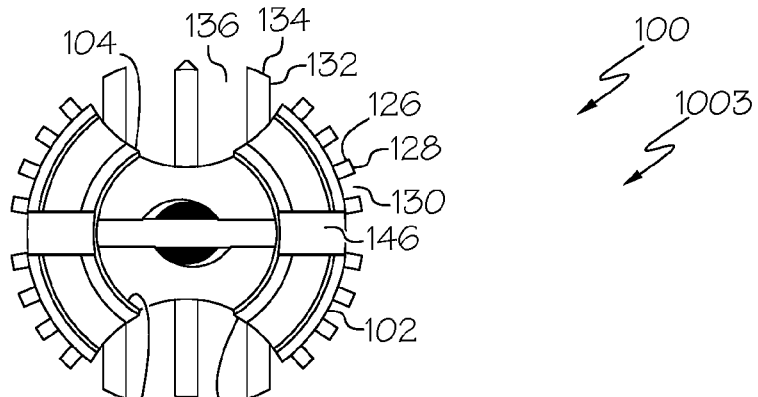
FIG. 19 is a top view of the implant of FIG. 16.
Figure 20:
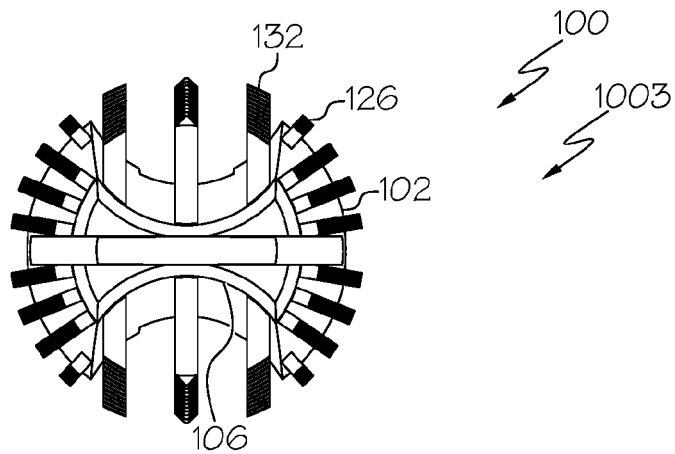
FIG. 20 is a bottom view of the implant of FIG. 16.
Figure 21:
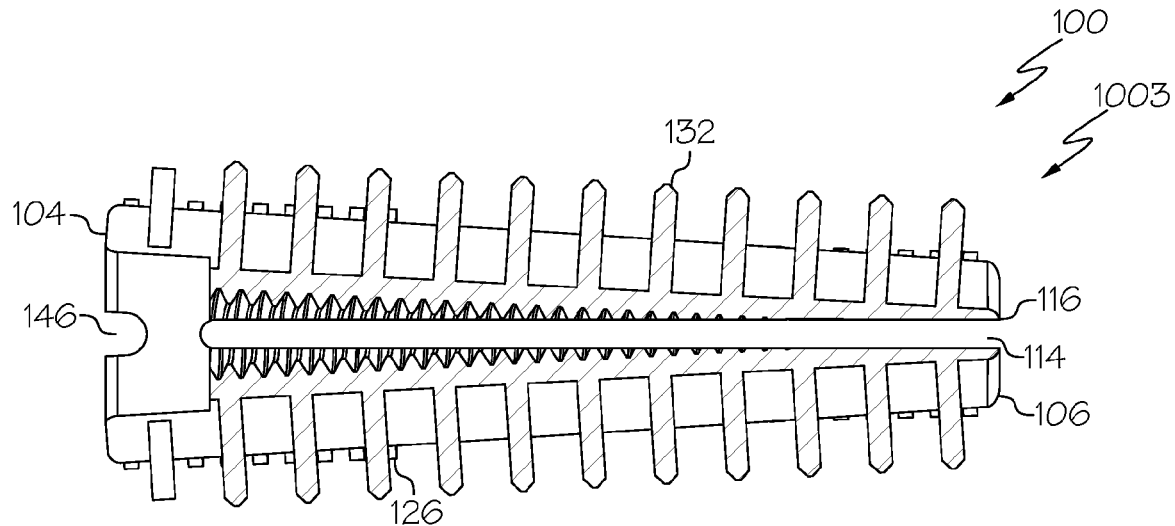
FIG. 21 is a sectional view of the implant of FIG. 17.
Figure 22:
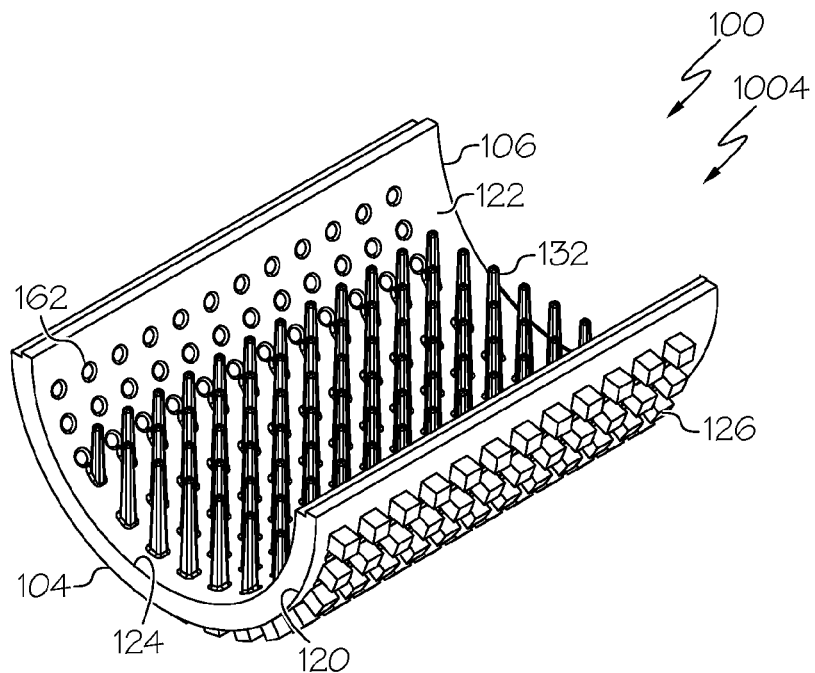
FIG. 22 is a first perspective view of a fourth embodiment of an implant for attaching a tendon or a ligament to a hard tissue as disclosed herein.
Figure 23:
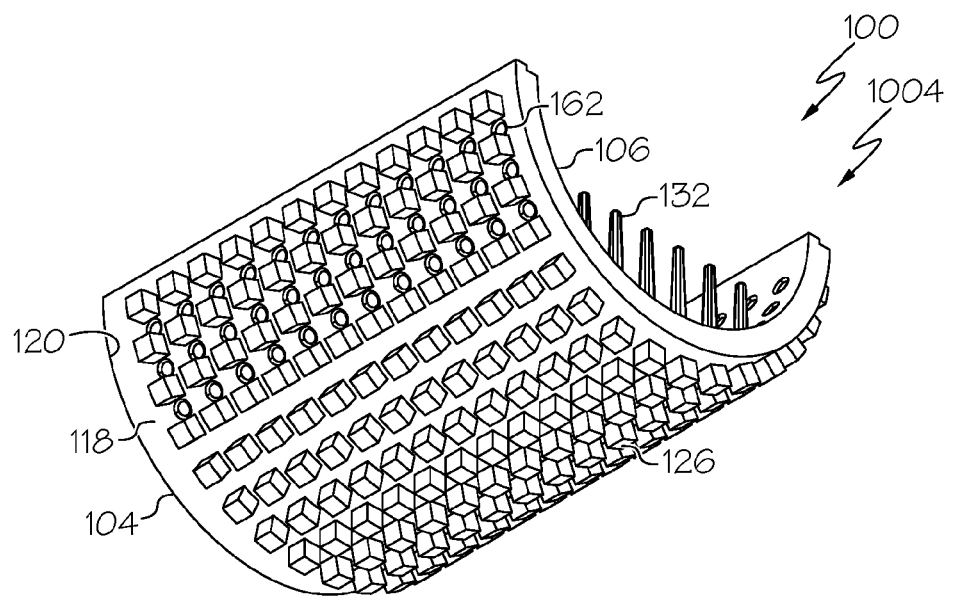
FIG. 23 is a second perspective view of the implant of FIG. 22.
Figure 24:
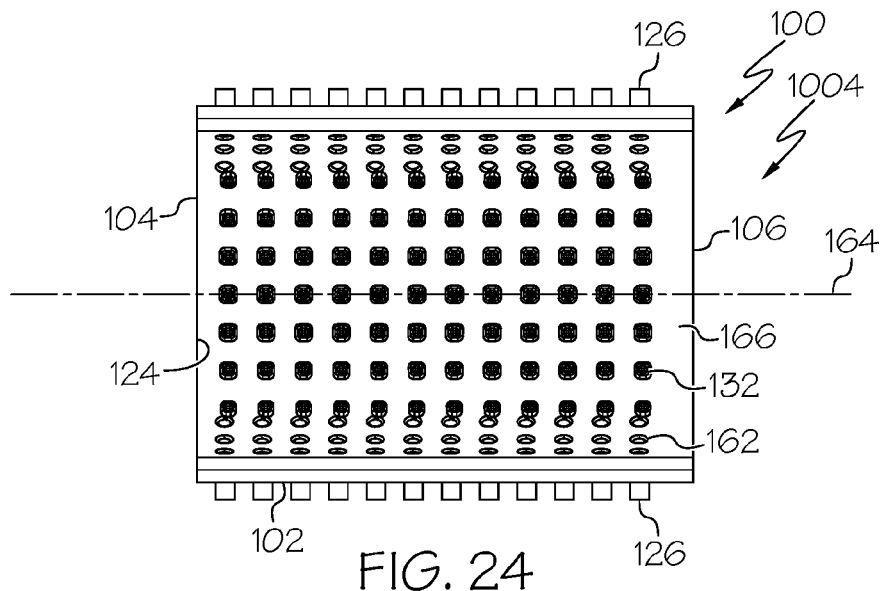
FIG. 24 is a first side view of the implant of FIG. 22.
Figure 25:
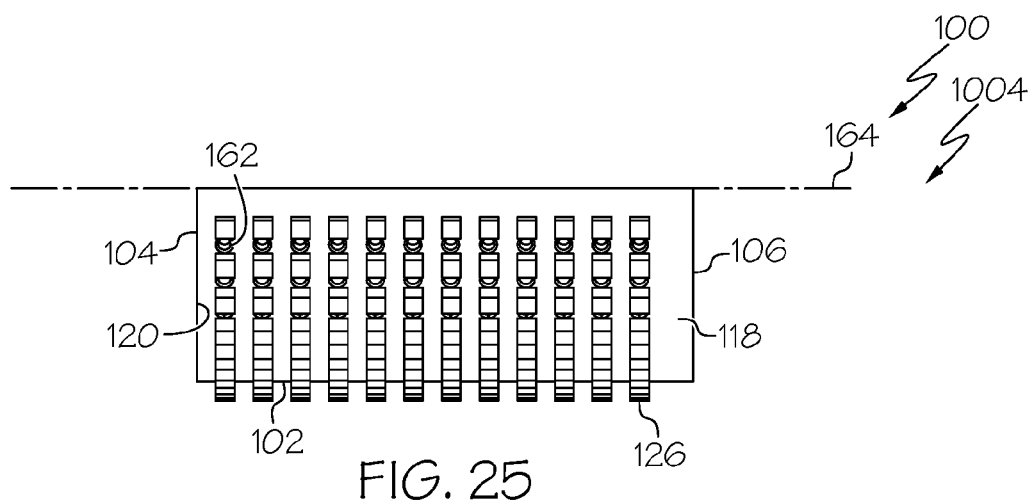
FIG. 25 is a second side view of the implant of FIG. 22.
Figure 26:
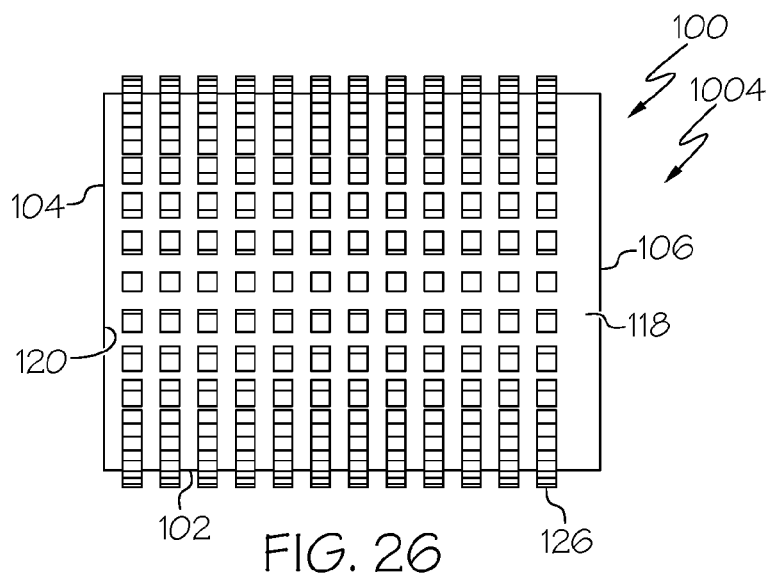
FIG. 26 is a third side view of the implant of FIG. 22.
Figure 27:
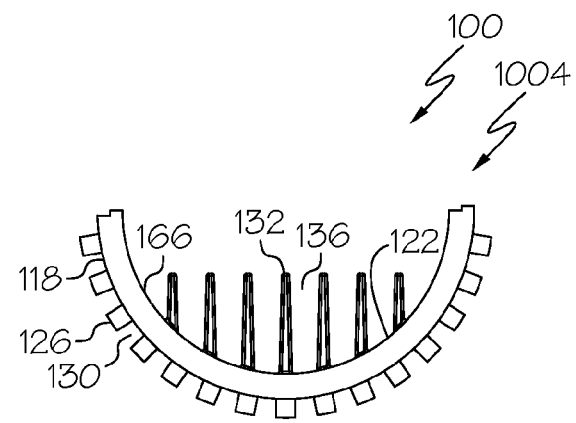
FIG. 27 is a top view of the implant of FIG. 22.
Figure 28:
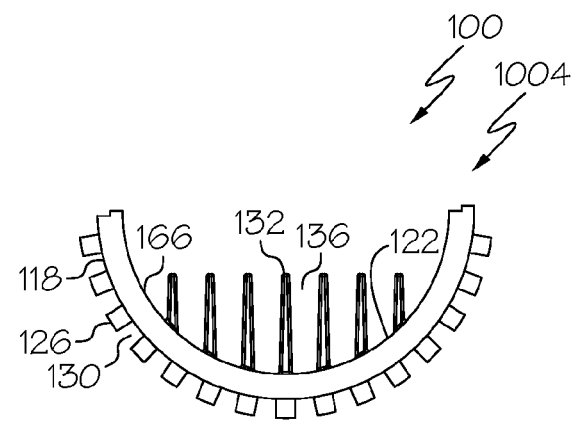
FIG. 28 is a bottom view of the implant of FIG. 22.

As shown in FIG. 1 and FIG. 7, in some examples the implant 100 further comprises a tool-engaging portion 138. In some examples the tool-engaging portion 138 comprises a thread 140 located in an internal passage 114 of the shaft 102 for engaging a tool, e.g. a tool to drive the implant 100 into a hard tissue by rotation. For example, as noted above, in some examples the shaft 102 has a top end aperture 112 located at the top end 104 of the shaft 102 and an internal passage 114 extending axially with respect to the shaft 102, from the top end aperture 112. Also, in some examples the internal passage 114 extends through the shaft 102, from the top end aperture 112, and ends within the shaft 102. In some of these examples the tool-engaging portion 138 comprises a thread 140 located in the internal passage 114. Alternatively or additionally, in some examples the tool-engaging portion 138 comprises a head 142 including a recess 144 located at the top end 104 of the shaft 102 for engaging a tool, e.g. a tool to press the implant 100 into a hard tissue. Alternatively or additionally, in some examples the tool-engaging portion 138 comprises a head 142 including notches 146 located at the top end of the shaft for engaging a tool. Other tool-engaging portions 138 suitable for driving, pressing, or otherwise inserting the implant 100 into a hard tissue also can be used.

In some examples, the implant 100 has one or more holes 162 in the shaft 102. The holes 162 pass through the shaft 102, from the first surface 118 to the second surface 122. The holes 162 can have diameters of, for example, 200 μm to 4 mm, 300 μm to 1 mm, or 400 μm to 600 μm, among other diameters. In some of these examples, the second pillars 132 are distributed centrally along the shaft 102, from near the top end 104 to near the bottom end 106, and a plurality of holes 162 are distributed peripherally along the shaft 102, from near the top end 104 to near the bottom end 106. The plurality of holes 162 can allow bone ingrowth therethrough following implantation of the implant 100. Also in some of these examples, the one or more holes 162 are located at or near the bottom end 106 of the shaft 102. The one or more holes 162 can be used for passing a suture. The suture can then be used for pulling the implant 100 into a hard tissue, e.g. into a bone tunnel of a bone.

Considering additional features, FIGS. 8-15 illustrate a second embodiment 1002 of an implant 100 for attaching a tendon or a ligament to a hard tissue. In accordance with this embodiment, the implant 100 further comprises a central slot 148 extending axially within the shaft 102 and a shaft hinge 150 extending axially along the shaft 102. The implant 100 comprises two first surfaces 118 of the shaft 102, separated by the central slot 148. The implant 100 also comprises two second surfaces 122 of the shaft 102, separated by the shaft hinge 150. The top end 104 of the shaft 102 of the implant 100 has a recessed portion 152. The central slot 148 extends from the recessed portion 152 axially to the bottom end 106 of the shaft 102. The shaft hinge 150 can be closed or open. When the shaft hinge 150 is closed, the implant 100 has a compact profile. When the shaft hinge 150 is opened, the implant 100 has an expanded profile. This embodiment provides an advantage by allowing the implant 100 to be pressed into a hole in a hard tissue while the shaft hinge 150 is closed and thus while the implant 100 has a compact profile and therefore with little or no contact between the first pillars 126, the second pillars 132, and the tendon or ligament and the hard tissue during pressing. Following insertion, the shaft hinge 150 can be opened, so that the implant 100 has an expanded profile. This can be done, for example, by inserting a wedge into the recessed portion 152 of the top end 104 of the shaft 102, then into the central slot 148, resulting opening of the shaft hinge 150, transition of the implant 100 from a compact profile to an expanded profile, and increased contact between the first pillars 126, the second pillars 132, and the tendon or ligament and the hard tissue.

FIGS. 16-21 illustrate a third embodiment 1003 of an implant 100 for attaching a tendon or a ligament to a hard tissue. In accordance with this embodiment, the implant 100 comprises two first surfaces 118 of the shaft 102, separated by two second surfaces 122 of the shaft 102. The two second surfaces 122 of the shaft 102 have a cross section transverse to the shaft 102 that is concave. The second pillars 132 of the implant 100 comprise some second pillars 132 that have distal ends 134 that are slanted, and other second pillars 132 that have distal ends 134 that are pointed. This embodiment may be used, for example, for attachment of two tendons or ligaments. One tendon or ligament can be attached to the implant 100 at one second surface 122, and the other tendon or ligament can be attached to the implant 100 at the other second surface 122. This embodiment also may be used, for example, for attachment of a tendon or ligament that has been split at an end of the tendon or ligament. One portion of the split tendon or ligament can be attached to the implant 100 at one second surface 122, and the other portion of the split tendon or ligament can be attached to the implant 100 at the other second surface 122.

This embodiment 1003 also may be varied, for example, such that the implant 100 only has one second surface 122 of the shaft 102. In accordance with this variation, the one second surface 122 of the shaft 102 also can have a cross section transverse to the shaft 102 that is concave. This variation can be useful, for example, for attachment of a single tendon or ligament.

FIGS. 22-28 illustrate a fourth embodiment 1004 of an implant 100 for attaching a tendon or a ligament to a hard tissue. In accordance with this embodiment, the implant 100 comprises a shaft 102 that has a central axis 164 and a trough 166 below the central axis 164 extending from the top end 104 of the shaft 102 to the bottom end 106 of the shaft 102.

The shaft 102 can have an arcuate shape, such as an arc of a semicircle of 180°, from a top view. The first surface 118 of the shaft 102 is an exterior surface of the shaft 102 as described above, e.g. the outer surface of the arcuately shaped shaft. The second surface 122 is a surface of the trough 166, e.g. the inner surface of the arcuately shaped shaft. The first pillars 126 are distributed on the first surface 118 as described above. The second pillars 132 are distributed on the second surface 122 as described above. This embodiment 1004 provides an advantage by shielding at least some of lateral surfaces of a tendon or ligament from contact with surfaces of a bone tunnel during insertion of the implant 100 into the bone tunnel.

Also in accordance with this embodiment, the implant 100 has a plurality of holes 162 in the shaft 102. The second pillars 132 are distributed centrally along the shaft 102, from near the top end 104 to near the bottom end 106, and the plurality of holes 162 are distributed peripherally along the shaft 102, from near the top end 104 to near the bottom end 106. The plurality of holes 162 can allow bone ingrowth therethrough following implantation of the implant 100. Moreover, one or more of the holes 162 that are located at or near the bottom end 106 of the shaft 102 can be used for passing a suture. The suture can then be used for pulling the implant 100 into a hard tissue, e.g. into a bone tunnel of a bone.

Figure 29:
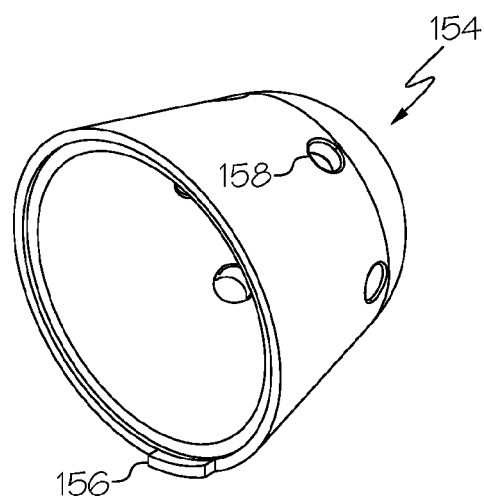
FIG. 29 is a perspective view of a cap for the implant of FIG. 22.
Figure 30:
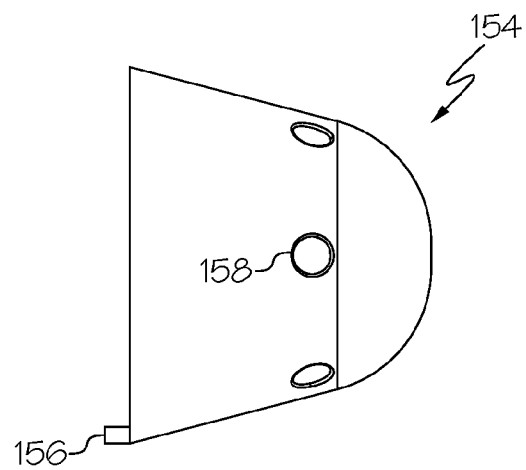
FIG. 30 is a side view of a cap for the implant of FIG. 22.
Figure 31:
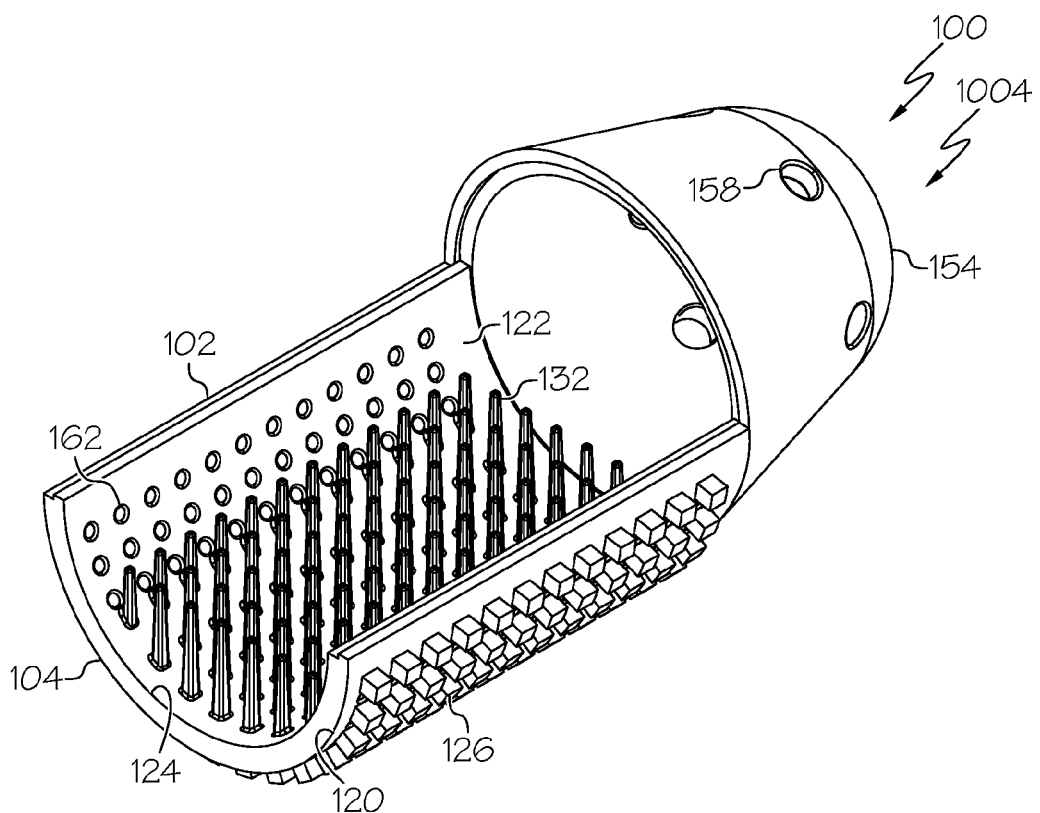
FIG. 31 is a first perspective view of the implant of FIG. 22 with the cap of FIG. 29 attached to the implant, in which the cap is in a closed configuration.
Figure 32:
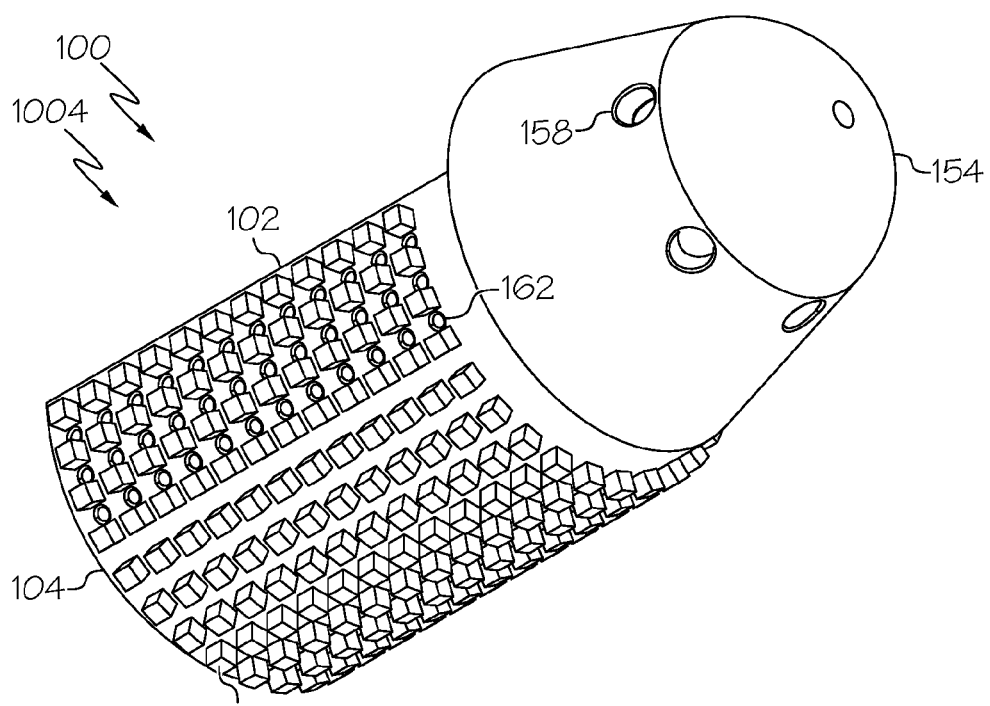
FIG. 32 is a second perspective view of the implant and cap of FIG. 31, in which the cap is in a closed configuration.
Figure 33:
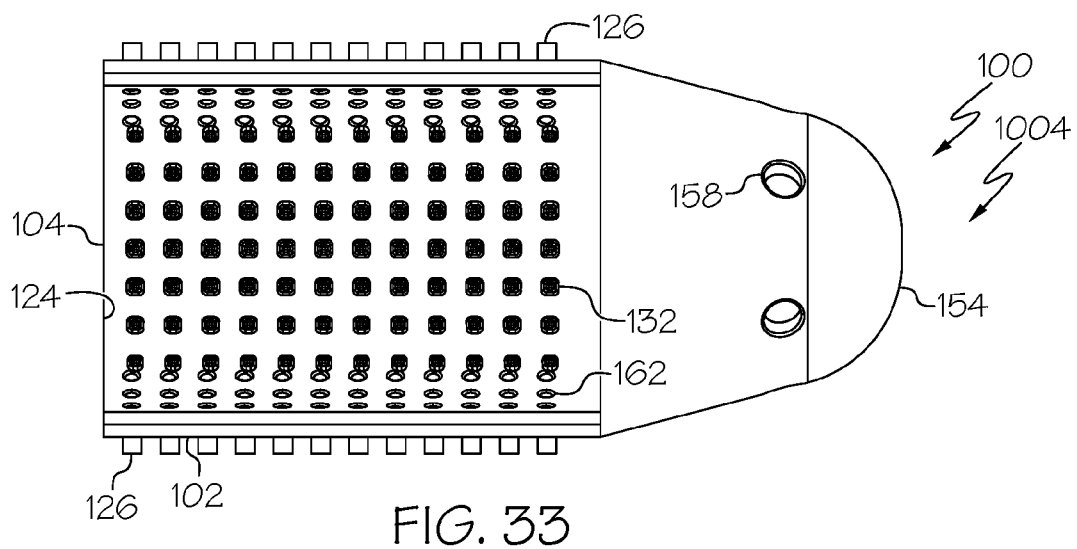
FIG. 33 is a first side view of the implant and cap of FIG. 31, in which the cap is in a closed configuration.
Figure 34:
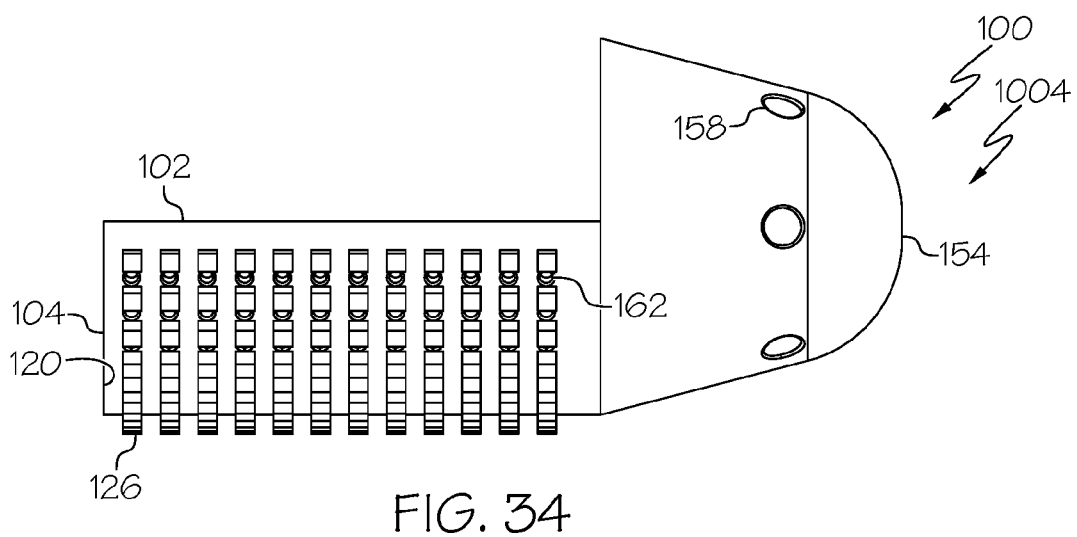
FIG. 34 is a second side view of the implant and cap of FIG. 31, in which the cap is in a closed configuration.
Figure 35:
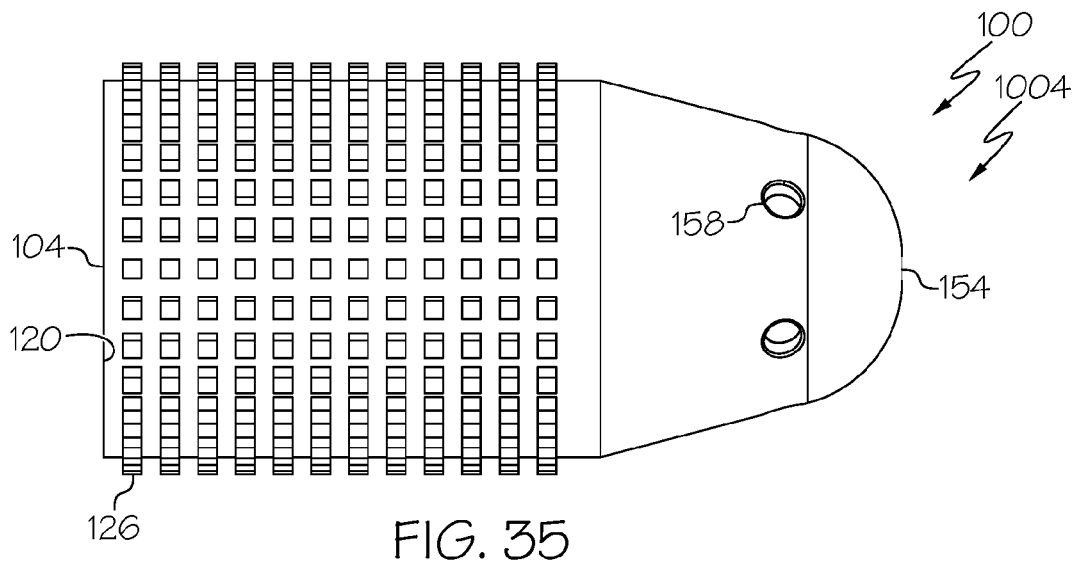
FIG. 35 is a third side view of the implant and cap of FIG. 31, in which the cap is in a closed configuration.
Figure 36:
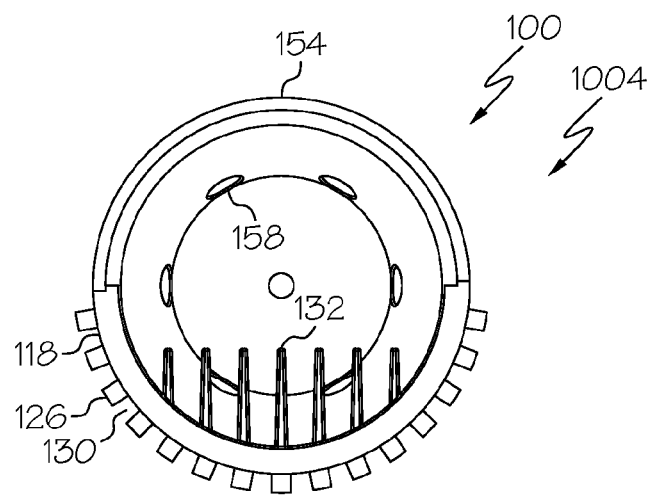
FIG. 36 is a top view of the implant and cap of FIG. 31, in which the cap is in a closed configuration.
Figure 37:
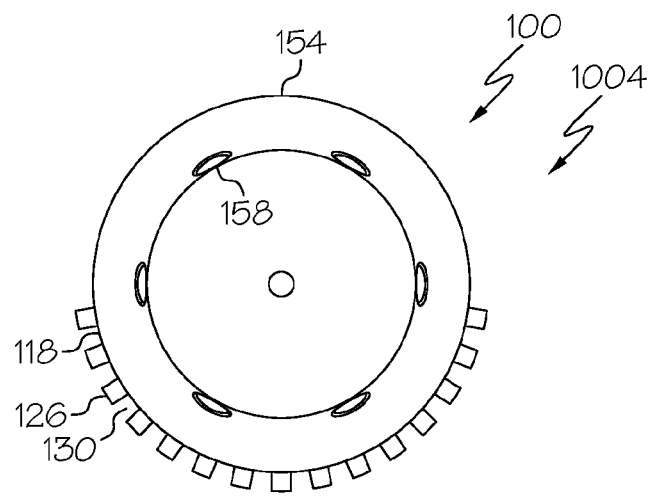
FIG. 37 is a bottom view of the implant and cap of FIG. 31, in which the cap is in a closed configuration.

FIG. 29 and FIG. 30 illustrate a cap 154 for an implant 100 for attaching a tendon or a ligament to a hard tissue as disclosed herein. In some examples the implant 100 further comprises a cap 154 attached to the shaft 102 of the implant 100 at the bottom end 106 of the shaft 102. The cap 154 can provide an advantage in terms of protecting the tendon or ligament during insertion of the implant 100 into a hard tissue.

As shown in FIG. 29 and FIG. 30, the cap 154 can include a hinge 156 for attachment of the cap 154 to the implant 100 at the bottom end 106 of the shaft 102. Thus, in some examples, the cap 154 is a covering that can be pivoted away from the bottom end 106 of the shaft 102, to allow attachment of a tendon or ligament along the second surface 122 of the shaft 102 without interference between the cap 154 and an end of the tendon or ligament, and then pivoted toward the bottom end 106 of the shaft 102, to protect the tendon or ligament during implantation. The hinge 156 can be, for example, a living hinge. In other examples the cap 154 is attached to shaft in a fixed manner. For example, the cap 154 can be a plate, e.g. a circular plate having a diameter approximately equal to that of the bottom end 106 of the shaft 102, that is attached at the bottom end 106 of the shaft 102 such that cap 154 cannot pivot or otherwise move with respect to the shaft 102.

As shown in FIG. 29 and FIG. 30, the cap 154 also can include one or more holes 158. The holes 158 of the cap 154 can be used for passing a suture. The suture can then be used for pulling the implant 100 into a hard tissue, e.g. into a bone tunnel of a bone.

Figure 38:
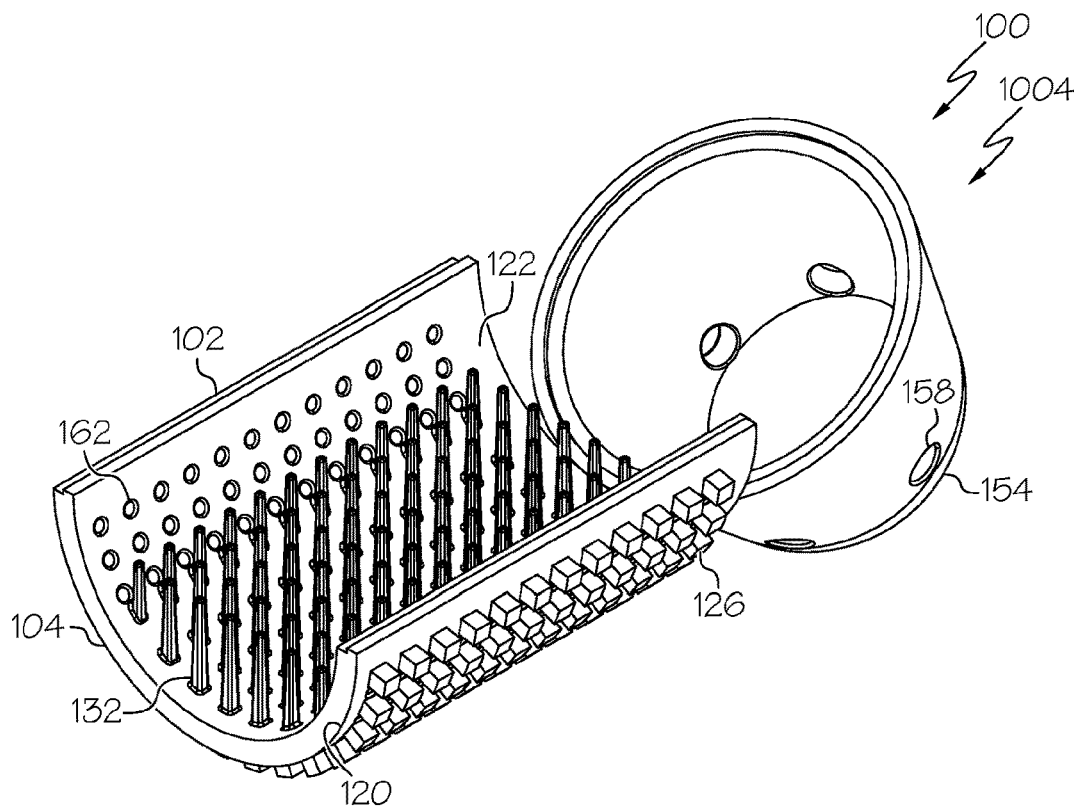
FIG. 38 is a first perspective view of the implant and cap of FIG. 31, in which the cap is in an open configuration.
Figure 39:
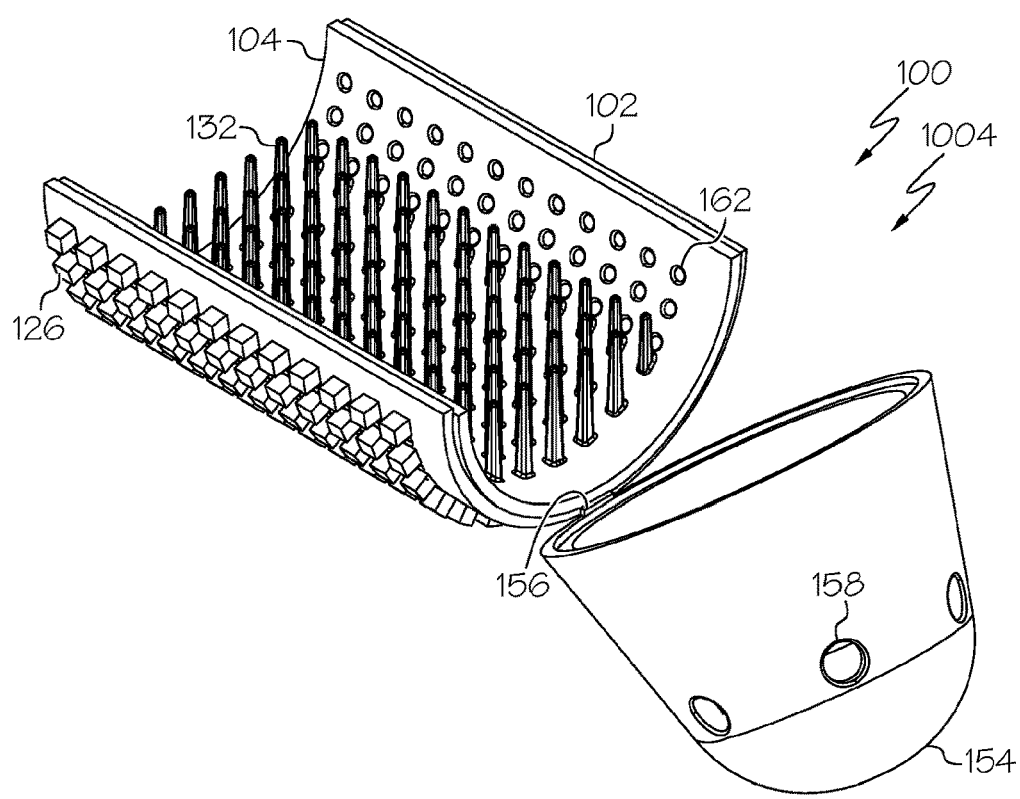
FIG. 39 is a second perspective view of the implant and cap of FIG. 31, in which the cap is in an open configuration.
Figure 40:
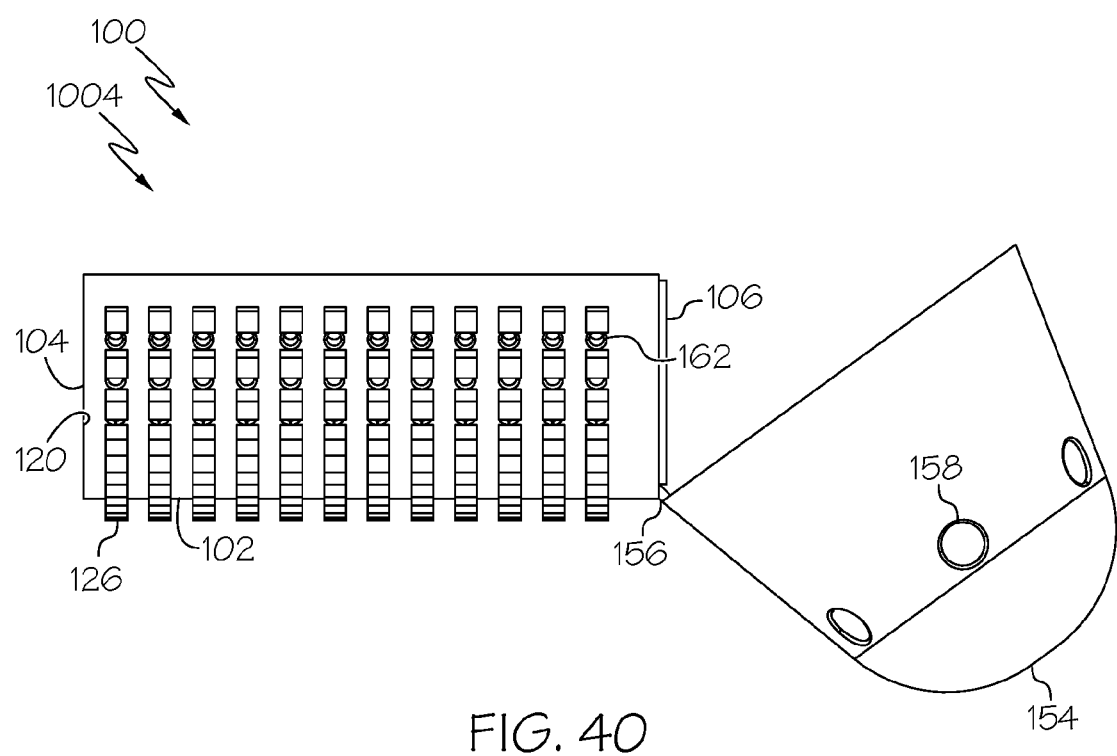
FIG. 40 is a side view of the implant and cap of FIG. 31, in which the cap is in an open configuration.
Figure 41:
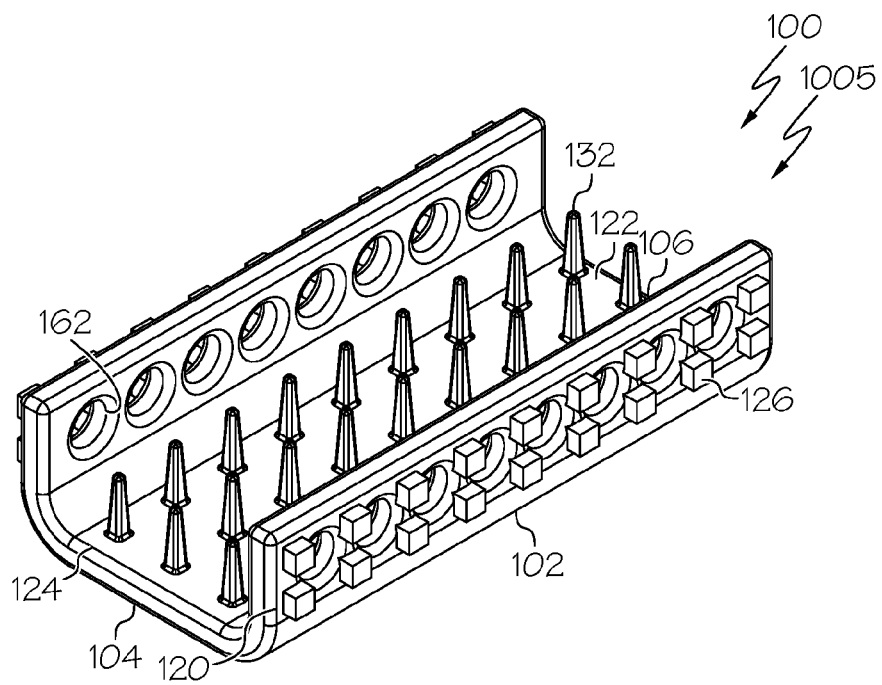
FIG. 41 is a first perspective view of a fifth embodiment of an implant for attaching a tendon or a ligament to a hard tissue as disclosed herein.
Figure 42:
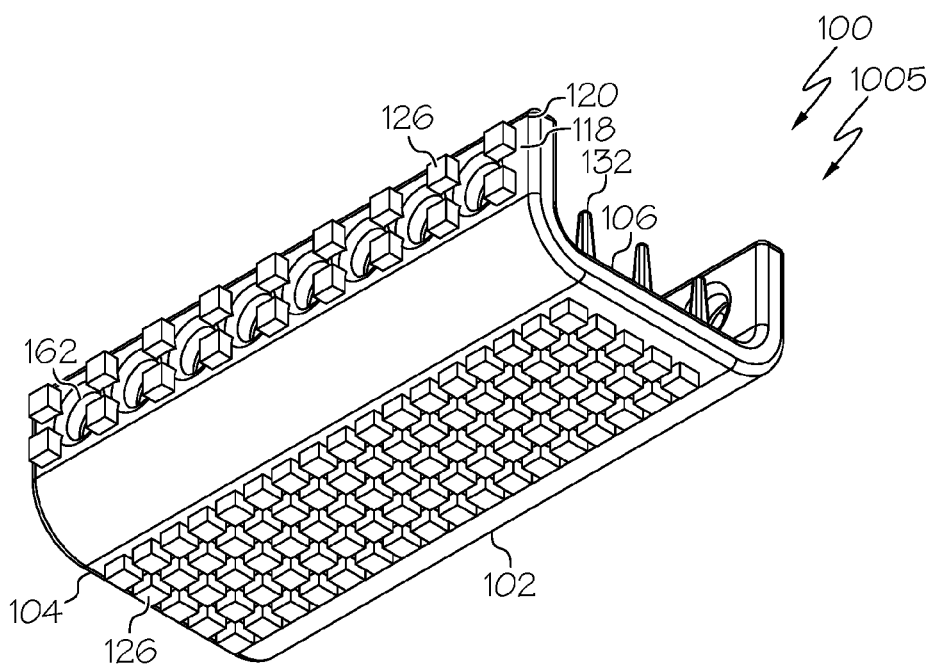
FIG. 42 is a second perspective view of the implant of FIG. 41.
Figure 43:
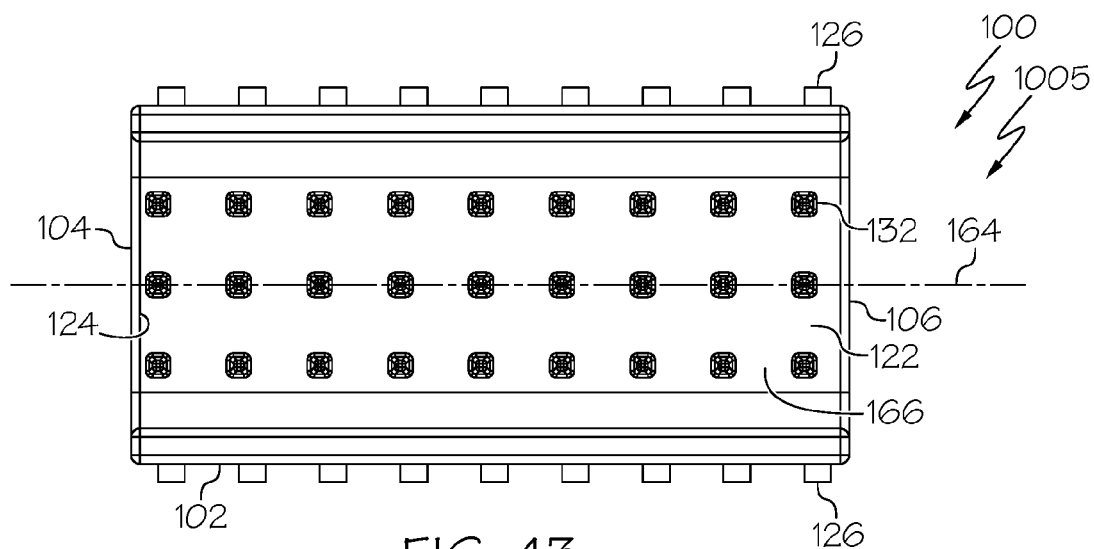
FIG. 43 is a first side view of the implant of FIG. 41.
Figure 44:
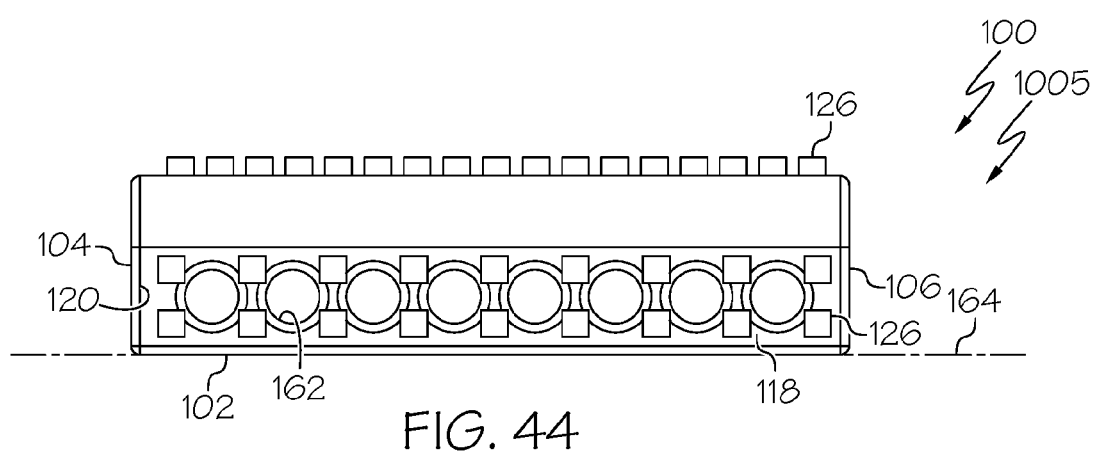
FIG. 44 is a second side view of the implant of FIG. 41.
Figure 45:
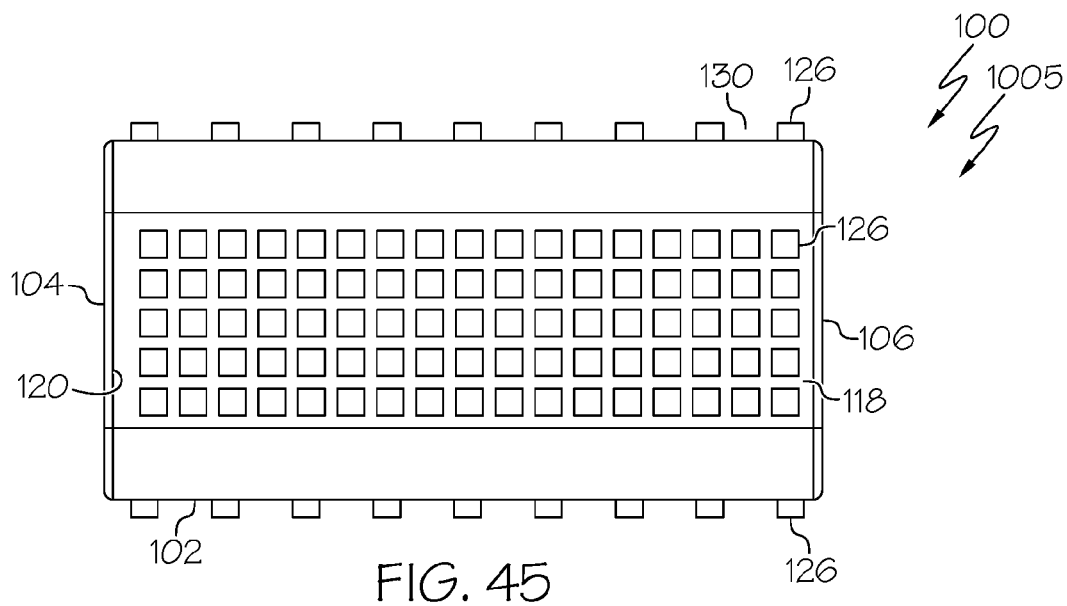
FIG. 45 is a third side view of the implant of FIG. 41.
Figure 46:
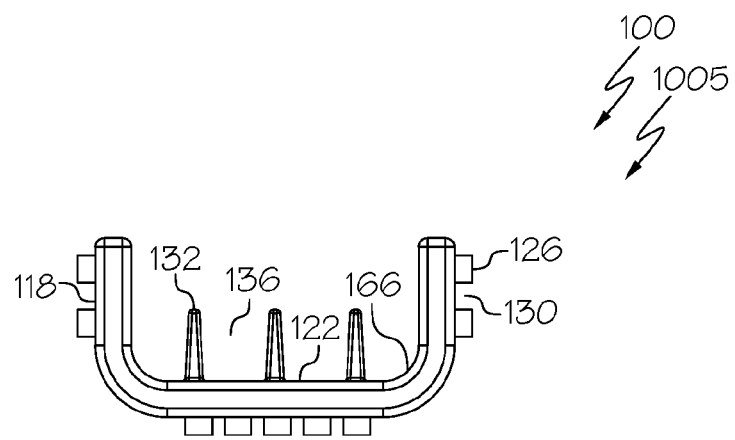
FIG. 46 is a top view of the implant of FIG. 41.
Figure 47:
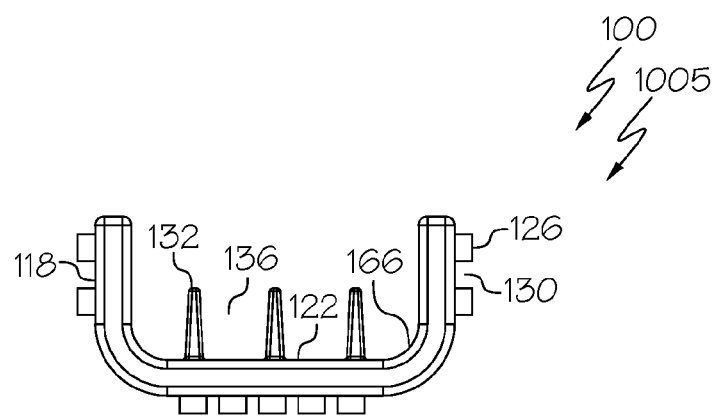
FIG. 47 is a bottom view of the implant of FIG. 41.

FIGS. 31-40 illustrate the fourth embodiment 1004 of the implant 100 with the cap 154 attached to the implant 100. FIGS. 31-37 show the cap 154 in a closed configuration with respect to the implant 100. FIGS. 38-40 show the cap 154 in an open configuration with respect to the implant 100. As shown, the cap 154 includes the hinge 156, e.g. a living hinge. Thus, in accordance with this embodiment, the cap 154 is a covering that can be pivoted away from the bottom end 106 of the shaft 102, to allow attachment of a tendon or ligament at the second pillars 132 along the second surface 122 of the shaft 102 without interference between the cap 154 and an end of the tendon or ligament, and then pivoted toward the bottom end 106 of the shaft 102, to protect the tendon or ligament during implantation. Also as shown, the cap 154 includes holes 158. Thus, in accordance with this embodiment, the holes 158 of the cap 154 can be used for passing a suture, which then can be used for pulling the implant 100 into a bone tunnel of a bone.

FIGS. 41-47 illustrate a fifth embodiment 1005 of an implant 100 for attaching a tendon or a ligament to a hard tissue. In accordance with this embodiment, the implant 100 again comprises a shaft 102 that has a central axis 164 and a trough 166 below the central axis 164 extending from the top end 104 of the shaft 102 to the bottom end 106 of the shaft 102. The shaft 102 can have a U-shape from a top view. The first surface 118 of the shaft 102 is an exterior surface of the shaft 102 as described above, e.g. the outer surface of the U-shaped shaft. The second surface 122 is a surface of the trough 166, e.g. the inner surface of the U-shaped shaft. The first pillars 126 are distributed on the first surface 118 as described above. The second pillars 132 are distributed on the second surface 122 as described above. This embodiment 1005 provides an advantage by shielding most or all of lateral surfaces of a tendon or ligament from contact with surfaces of a bone tunnel during insertion of the implant 100 into the bone tunnel.

Also in accordance with this embodiment, the implant 100 has a plurality of holes 162 in the shaft 102. The second pillars 132 are distributed centrally along the shaft 102, from near the top end 104 to near the bottom end 106, and the plurality of holes 162 are distributed peripherally along the shaft 102, from near the top end 104 to near the bottom end 106. The plurality of holes 162 can allow bone ingrowth therethrough following implantation of the implant 100. Moreover, one or more of the holes 162 that are located at or near the bottom end 106 of the shaft 102 can be used for passing a suture. The suture can then be used for pulling the implant 100 into a hard tissue, e.g. into a bone tunnel of a bone.

Figure 48:
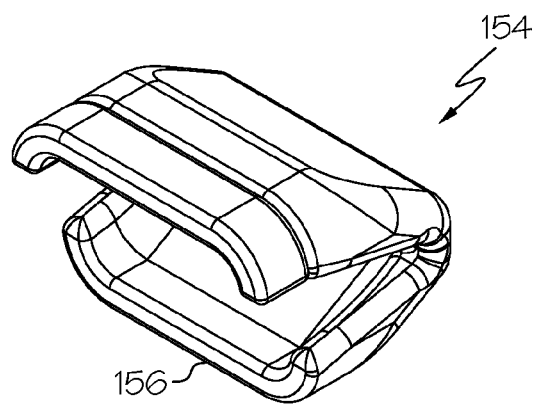
FIG. 48 is a perspective view of a cap for the implant of FIG. 41.
Figure 49:
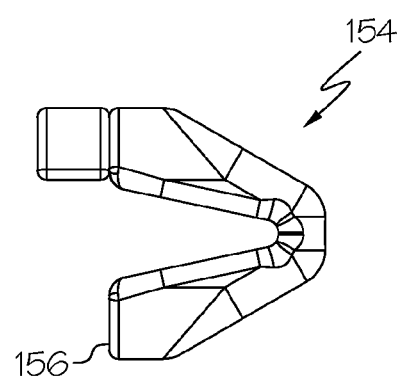
FIG. 49 is a side view of a cap for the implant of FIG. 41.
Figure 50:
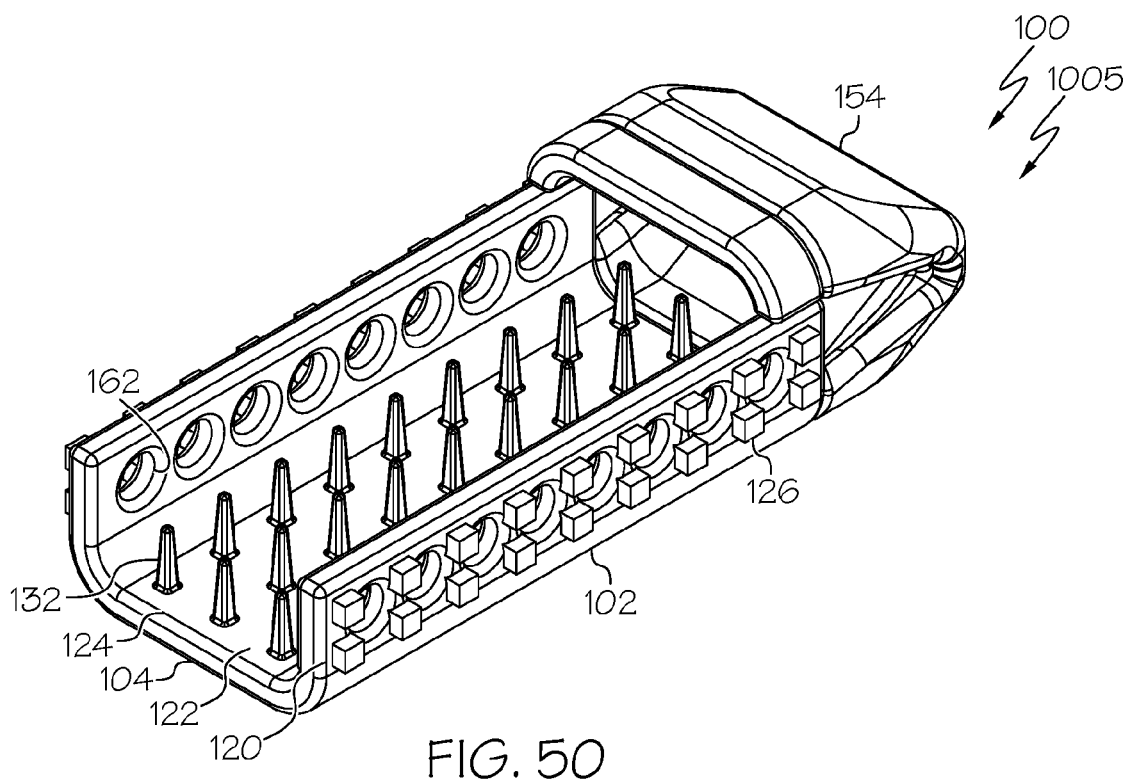
FIG. 50 is a first perspective view of the implant of FIG. 41 with the cap of FIG. 48 attached to the implant, in which the cap is in a closed configuration.
Figure 51:
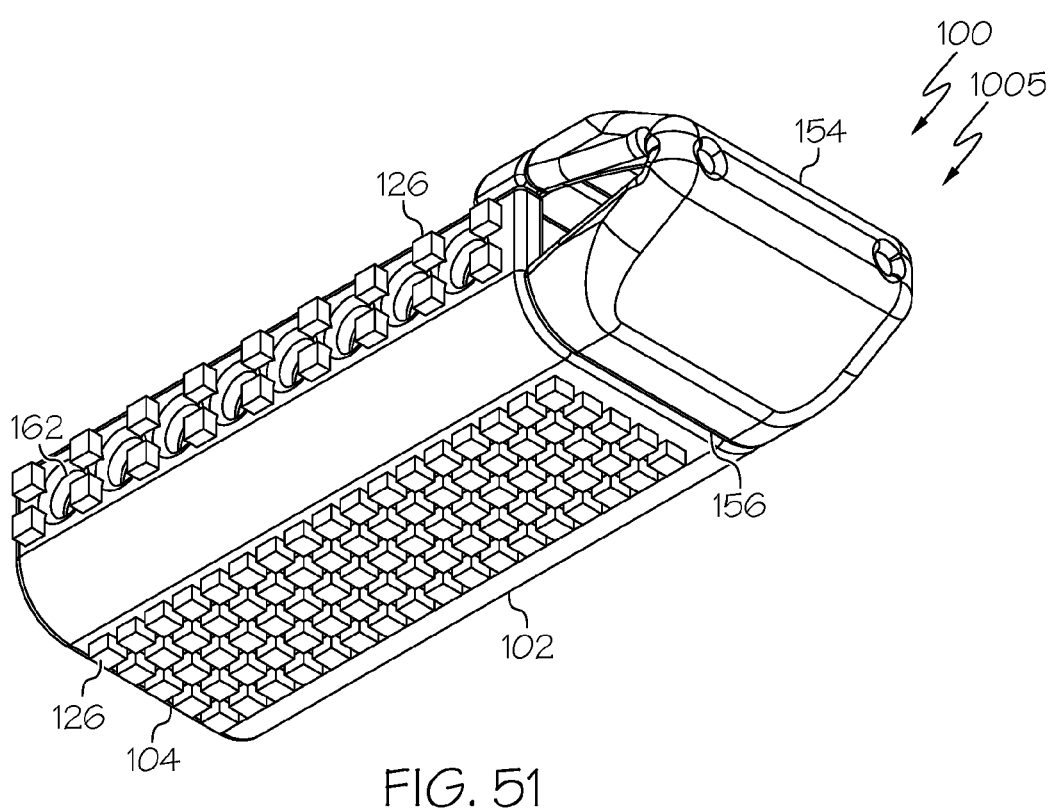
FIG. 51 is a second perspective view of the implant and cap of FIG. 50, in which the cap is in a closed configuration.
Figure 52:
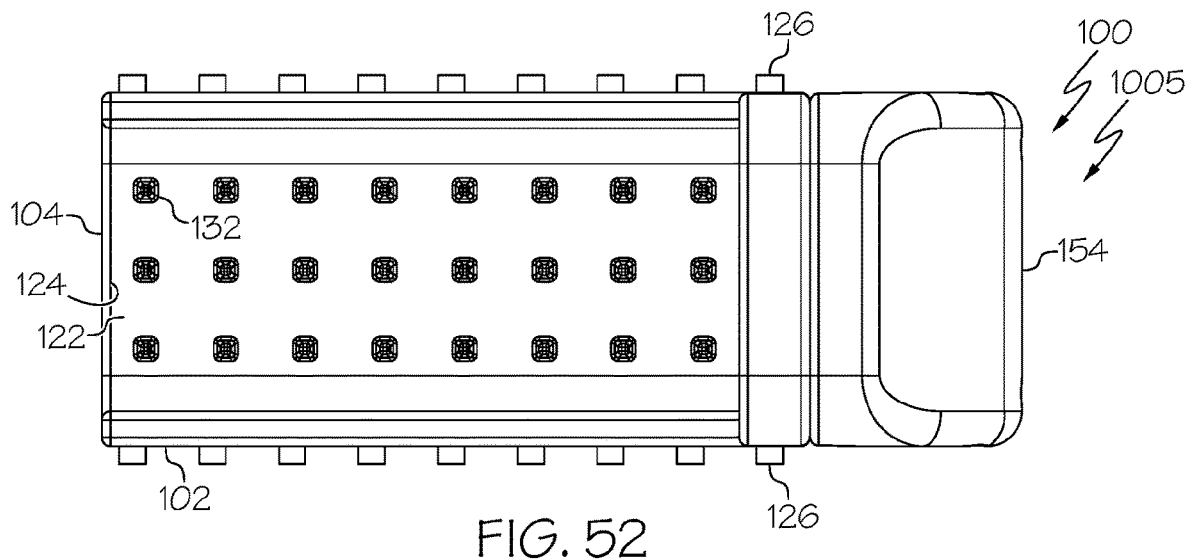
FIG. 52 is a first side view of the implant and cap of FIG. 50, in which the cap is in a closed configuration.
Figure 53:
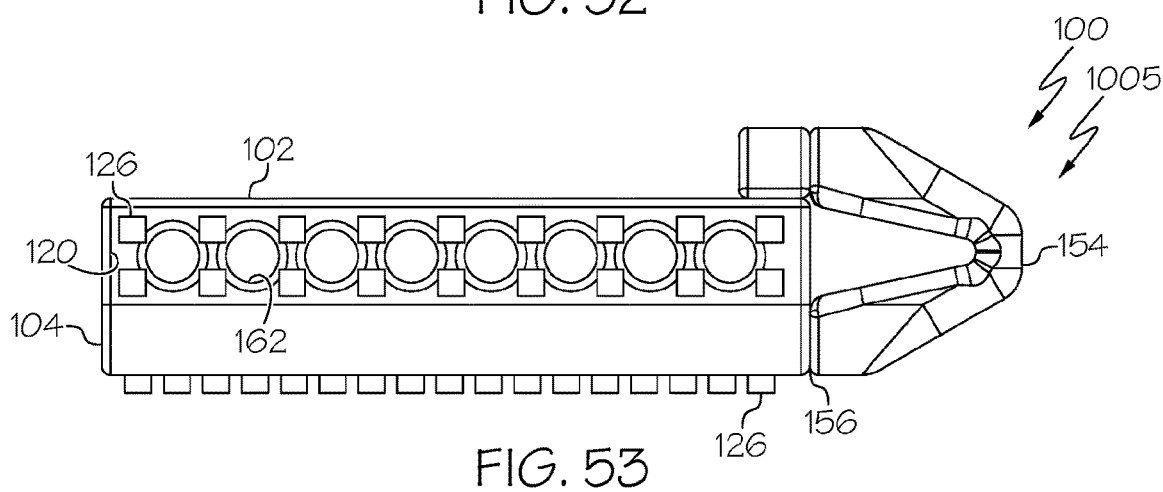
FIG. 53 is a second side view of the implant and cap of FIG. 50, in which the cap is in a closed configuration.
Figure 54:
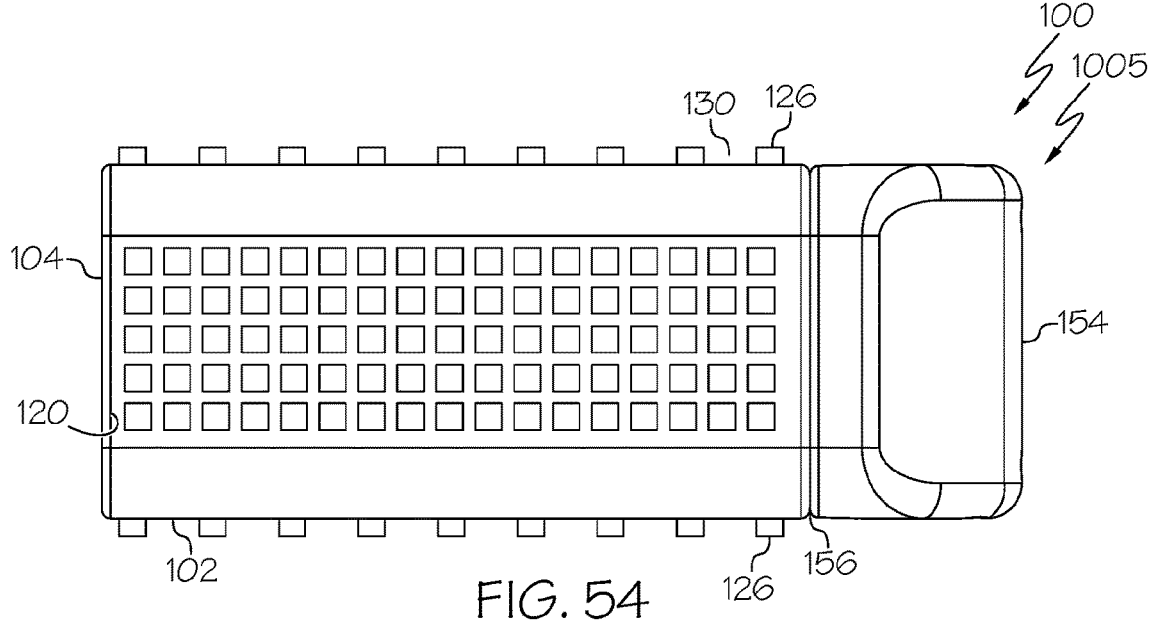
FIG. 54 is a third side view of the implant and cap of FIG. 50, in which the cap is in a closed configuration.
Figure 55:
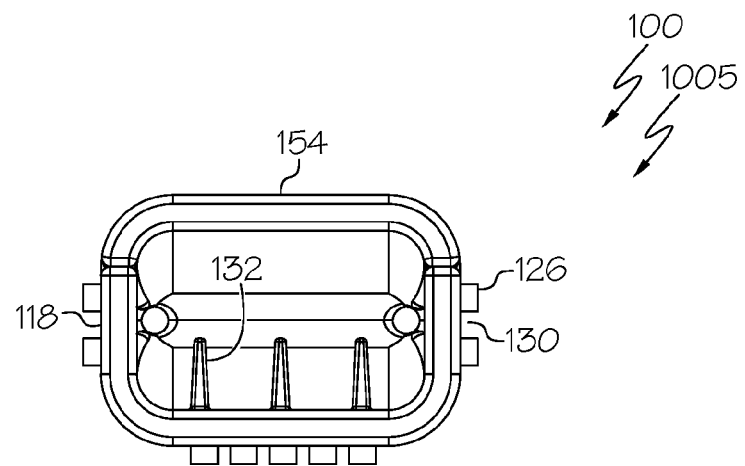
FIG. 55 is a top view of the implant and cap of FIG. 50, in which the cap is in a closed configuration.
Figure 56:
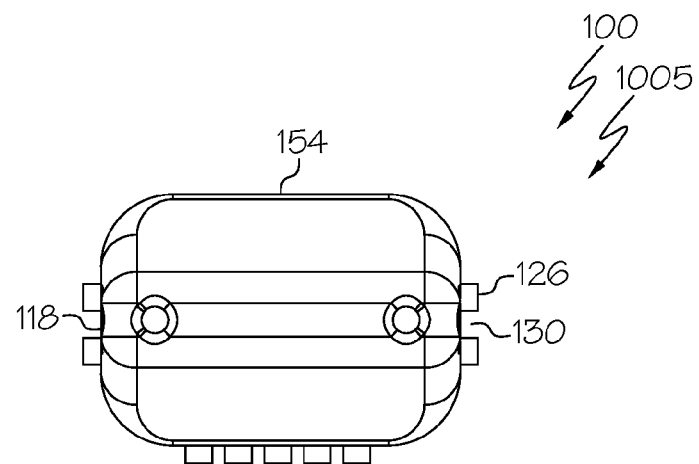
FIG. 56 is a bottom view of the implant and cap of FIG. 50, in which the cap is in a closed configuration.

FIG. 48 and FIG. 49 illustrate another cap 154 for an implant 100 for attaching a tendon or a ligament to a hard tissue as disclosed herein. The cap 154 includes a hinge 156, e.g. a living hinge, for attachment of the cap 154 to the implant 100 at the bottom end 106 of the shaft 102.

Figure 57:
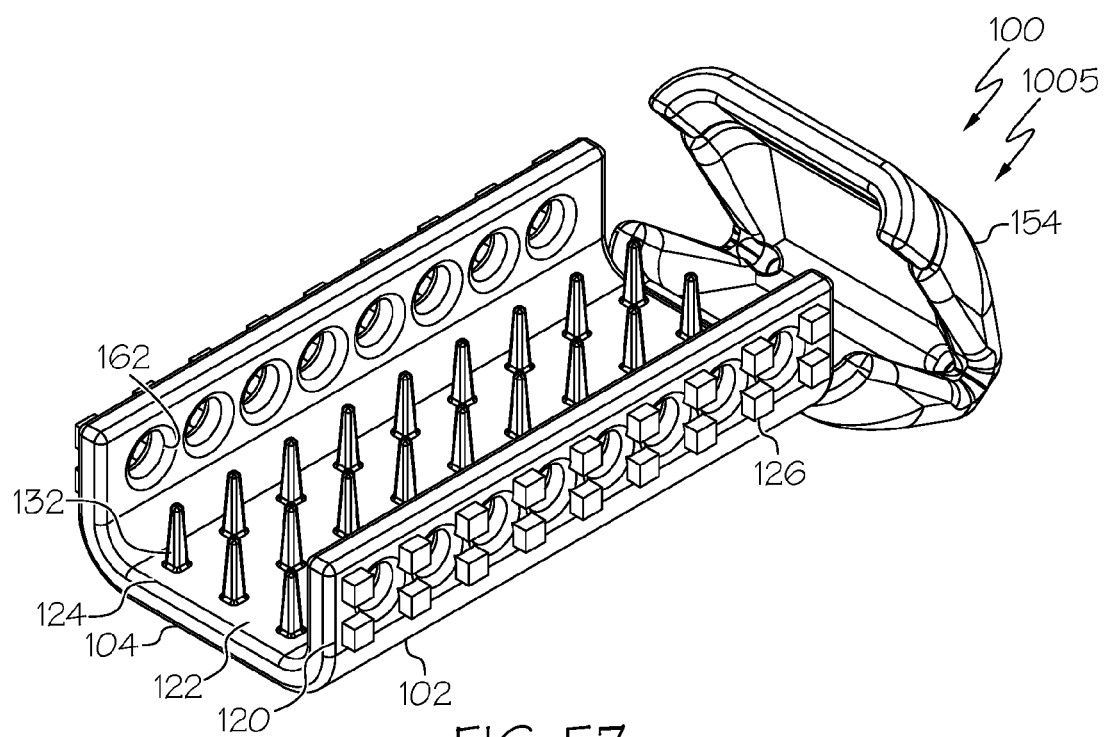
FIG. 57 is a first perspective view of the implant and cap of FIG. 50, in which the cap is in an open configuration.
Figure 58:
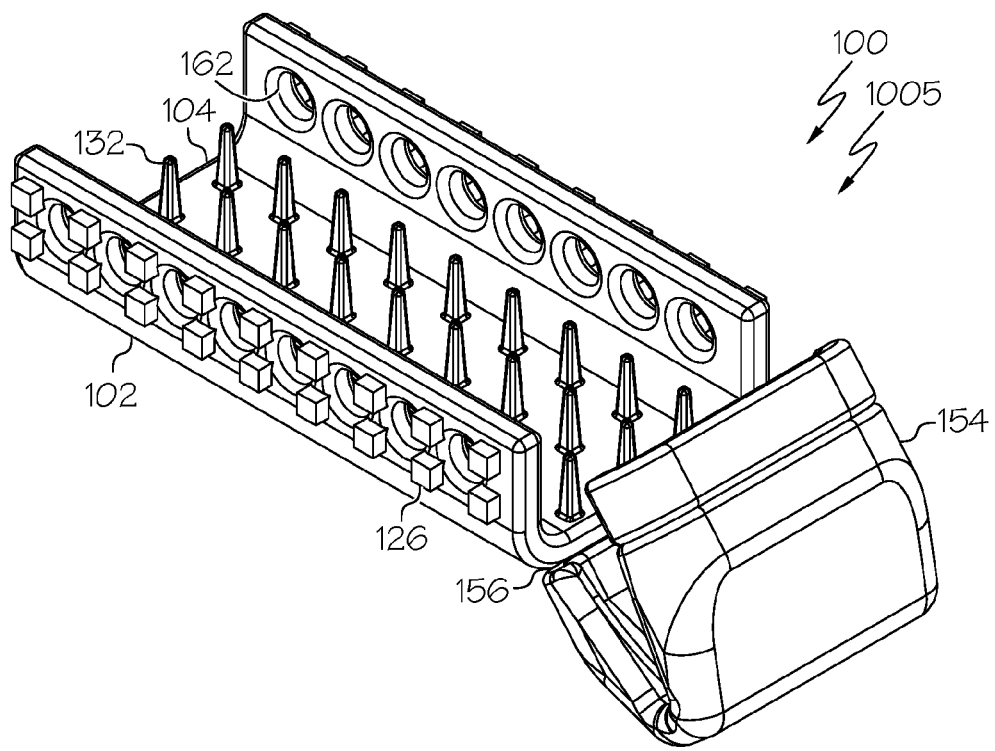
FIG. 58 is a second perspective view of the implant and cap of FIG. 50, in which the cap is in an open configuration.
Figure 59:
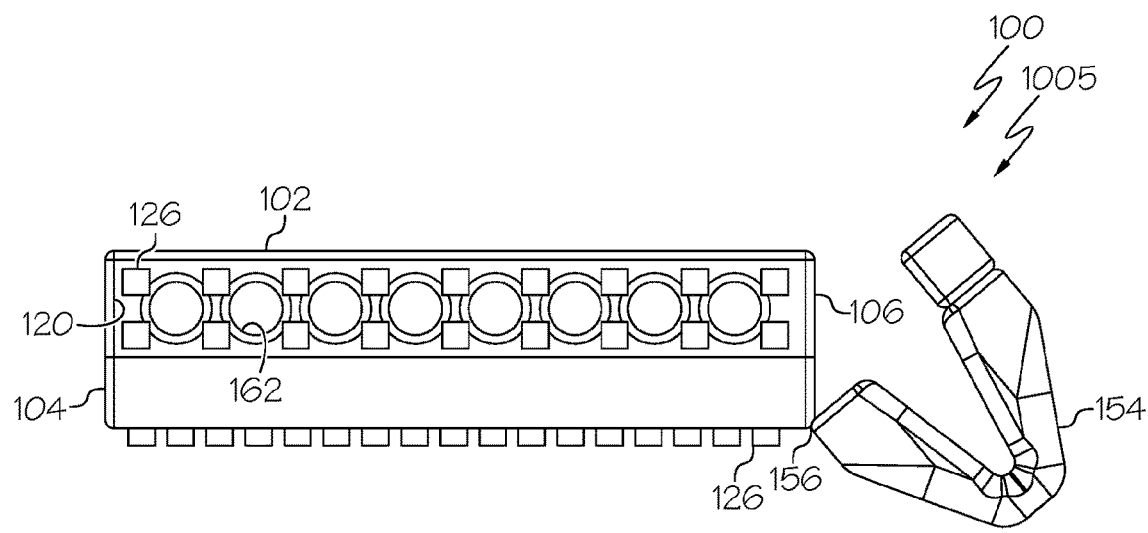
FIG. 59 is a side view of the implant and cap of FIG. 50, in which the cap is in an open configuration.

FIGS. 50-59 illustrate the fifth embodiment 1005 of the implant 100 with the cap 154 attached to the implant 100. FIGS. 50-56 show the cap 154 in a closed configuration with respect to the implant 100. FIGS. 57-59 show the cap 154 in an open configuration with respect to the implant 100. As shown, the cap 154 includes the hinge 156, e.g. a living hinge. Again, the cap 154 is a covering that can be pivoted away from the bottom end 106 of the shaft 102, to allow attachment of a tendon or ligament at the second pillars 132 along the second surface 122 of the shaft 102 without interference between the cap 154 and an end of the tendon or ligament, and then pivoted toward the bottom end 106 of the shaft 102, to protect the tendon or ligament during implantation.

Figure 60:
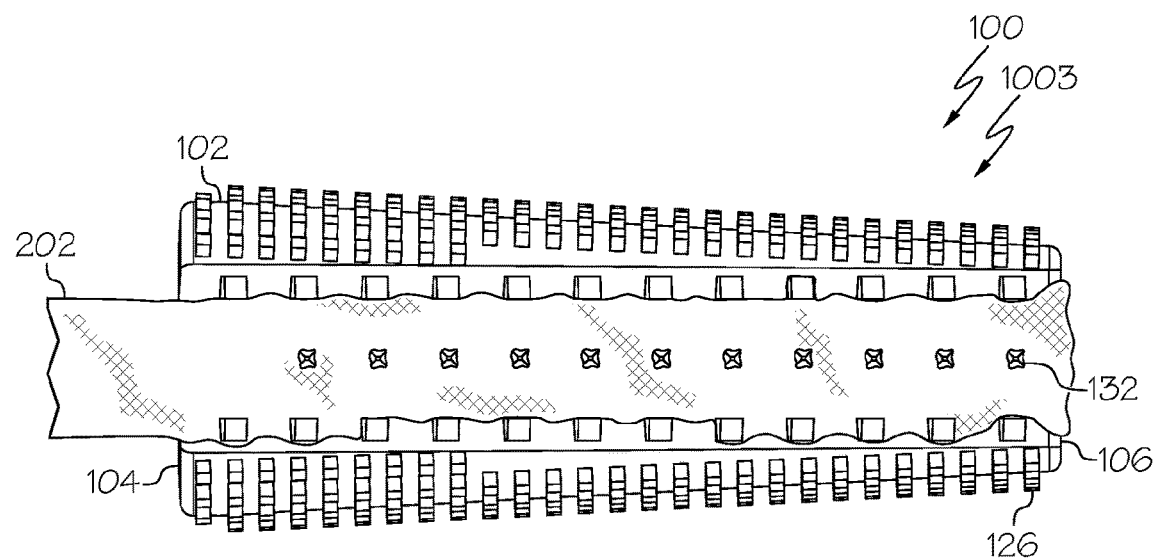
FIG. 60 is a side view of the implant of FIG. 16, to which a tendon has been pressed onto second pillars of the implant.

FIG. 60 shows a side view of the third embodiment 1003 of the implant 100 to which a tendon 202 has been pressed onto second pillars 132 of a second surface 122 of the implant 100. Another tendon can be attached at the other second surface 122 of this third embodiment 1003 of implant 100. A ligament could similarly be attached to this third embodiment 1003 of implant 100. A tendon or ligament also could similarly be attached to the other embodiments and examples of the implant 100 as described above.

The implant 100 can be made by fabrication methods such as laser cutting, injection molding, or 3D printing, among others.

Implant Assemblies for Attaching a Tendon or a Ligament to a Hard Tissue

Figure 61:
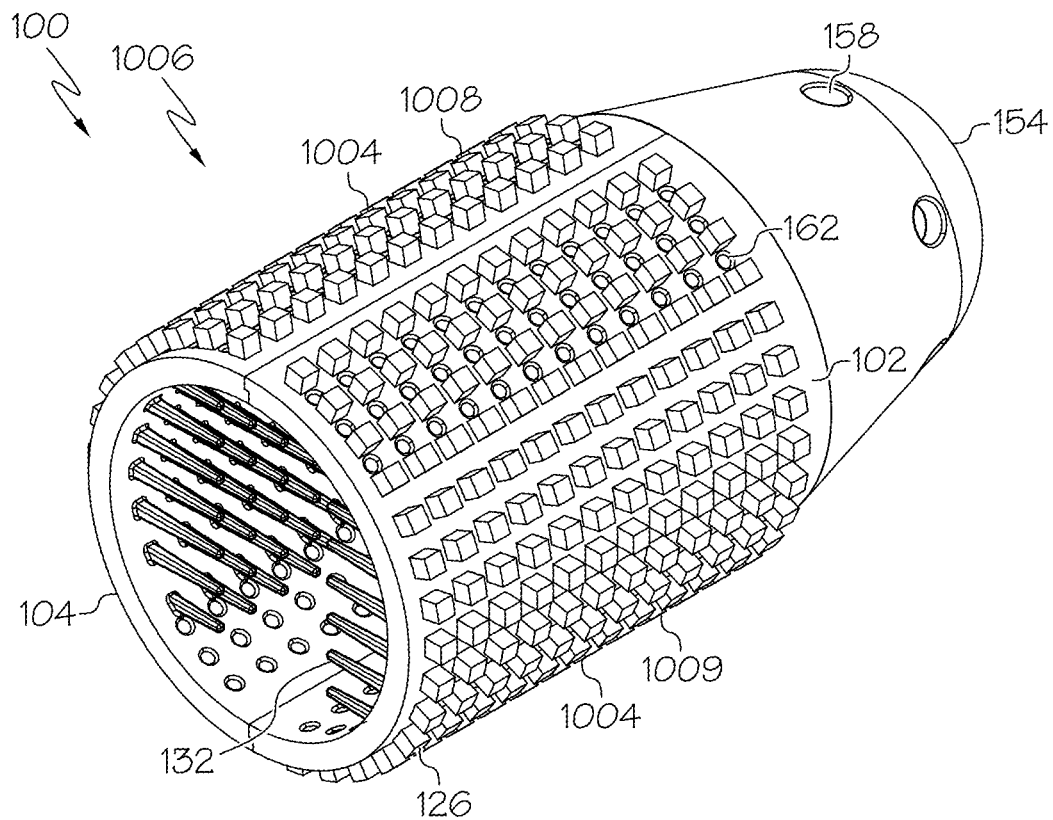
FIG. 61 is a first perspective view of an implant assembly including the implant and cap of FIG. 31, in which the cap is in a closed configuration, and to which another implant of FIG. 22 has been added.
Figure 62:
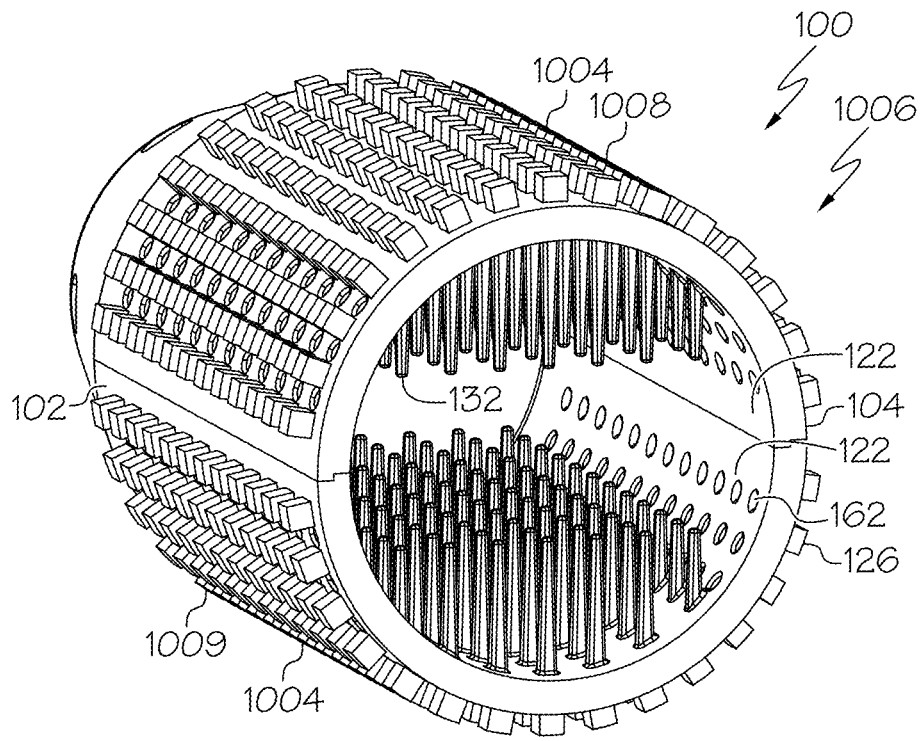
FIG. 62 is a second perspective view of the implant assembly of FIG. 61.

Turning to the features of the implant assembly for attaching a tendon or a ligament to a hard tissue, FIG. 61 and FIG. 62 illustrate an implant assembly 1006 comprising first and second implants 1008, 1009 as described for implant 100 above, and a cap 154, also as described above. The cap 154 is attached to the shaft 102 of the first implant 1008 at the bottom end 106 of the shaft 102. The second implant 1009 is attached to the first implant 1008 along the shaft 102 of the first implant 1008 and faces second surface 122 of the shaft 102 of the first implant 1008. As shown in FIG. 61 and FIG. 62, the cap 154 is in a closed configuration.

The implant assembly 1006 provides an advantage by further shielding lateral surfaces of a tendon or ligament from contact with surfaces of a bone tunnel during insertion of the implant assembly 1006 into the bone tunnel.

The implant assembly 1006 can be assembled during use as follows. A first implant 1008, corresponding for example to embodiment 1004, with a cap 154 attached, is provided. As discussed above, the cap 154 includes a hinge 156, e.g. a living hinge. The cap 154 is pivoted away from the bottom end 106 of the shaft 102. Then a tendon or ligament is attached at the second pillars 132 along the second surface 122 of the shaft 102 of the first implant 1008 without interference between the cap 154 and an end of the tendon or ligament. Next the cap 154 is pivoted toward the bottom end 106 of the shaft 102, to protect the tendon or ligament during implantation. Then the second implant 1009, also corresponding for example to embodiment 1004, is attached to the first implant 1008 along the shaft 102 of the first implant 1008, facing the second surface 122 of the first implant 1008. The attachment can be, for example, based on a complementary fit between the first implant 1008 and the second implant 1009. This further shields lateral surfaces of the tendon or ligament from contact with surfaces of a bone tunnel during insertion of the implant assembly 1006 into the bone tunnel.

Figure 63:
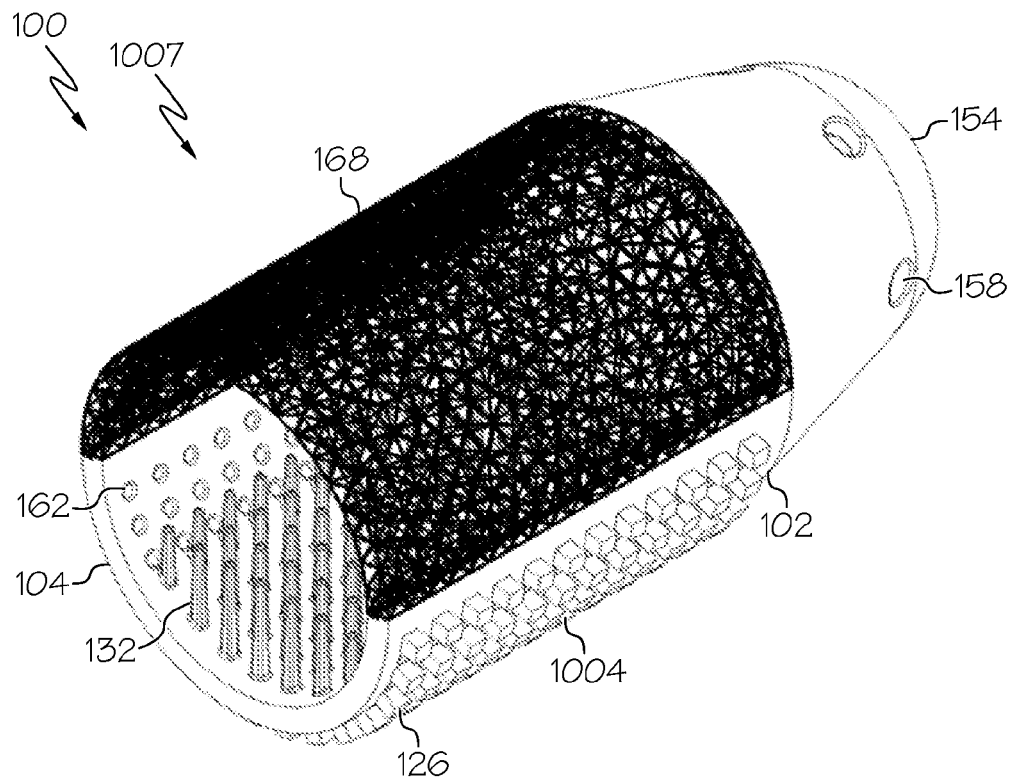
FIG. 63 is a first perspective view of a second embodiment of another implant assembly including the implant and cap of FIG. 31, in which the cap is in a closed configuration, and to which a mesh part has been added.
Figure 64:
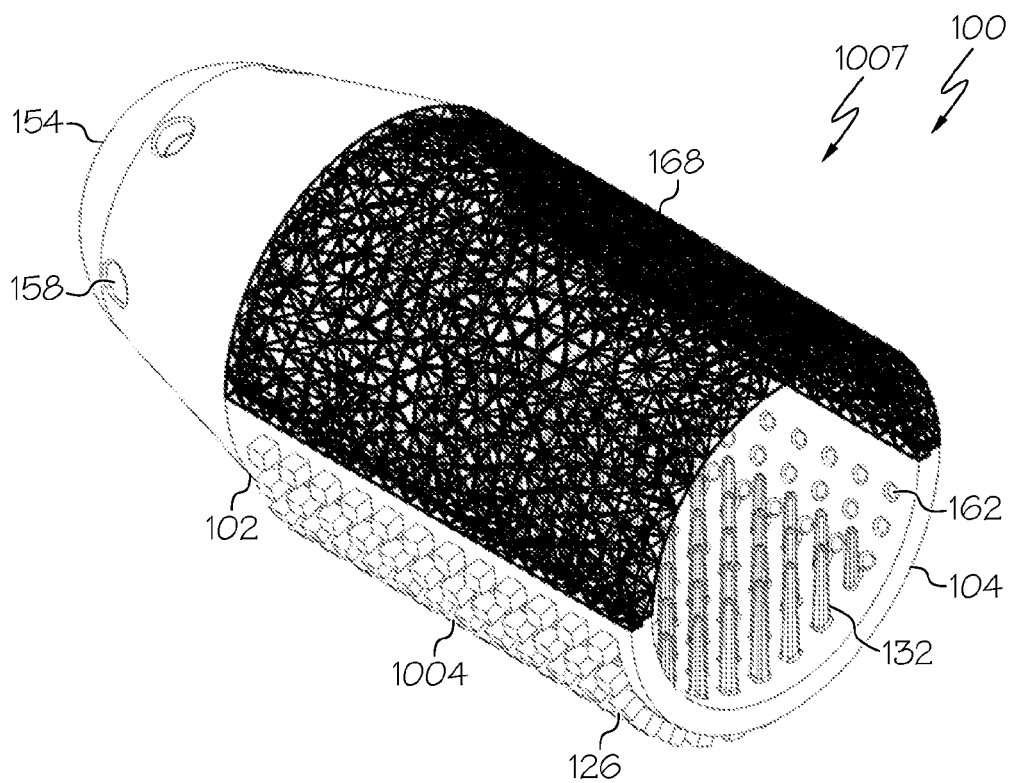
FIG. 64 is a second perspective view of the implant assembly of FIG. 63.
Figure 65:
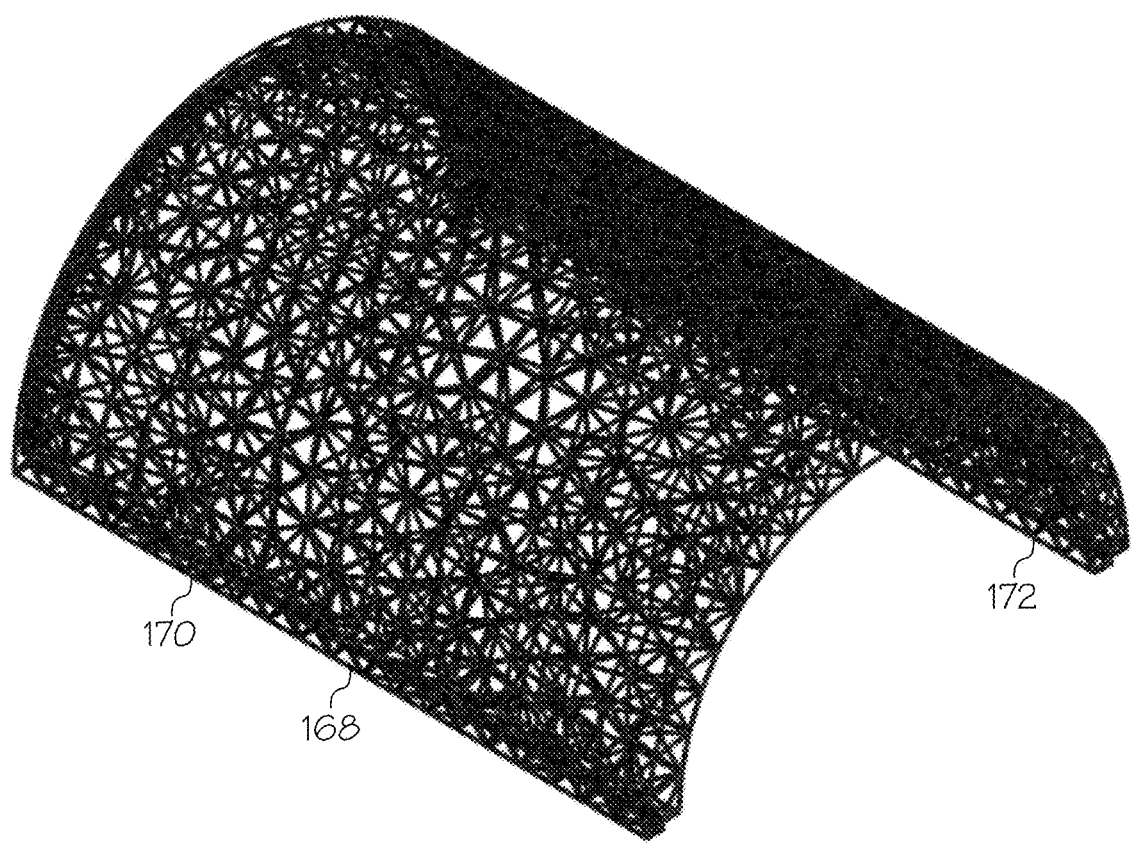
FIG. 65 is a perspective view of the mesh part of the implant assembly of FIG. 63.

FIG. 63 and FIG. 64 illustrate an implant assembly 1007 comprising an implant 100 as described above, a cap 154, also as described above, and a mesh part 168. The cap 154 is attached to the shaft 102 of the implant 100 at the bottom end 106 of the shaft 102. The mesh part 168 is attached to the implant 100 along the shaft 102 of the implant 100 and faces the second surface 122 of the shaft 102 of the implant 100. As shown in FIG. 63 and FIG. 64, the cap 154 is in a closed configuration.

The mesh part 168 can be made from a material having a Young's modulus of elasticity, i.e. a tensile modulus of elasticity, of at least 3 GPa, as measured at 21° C. that can be produced in a mesh geometry. The mesh part 168 can be made, for example, from implantable-grade polyaryletherketone that is essentially unfilled (such as implantable-grade polyetheretherketone or implantable-grade polyetherketoneketone), titanium, stainless steel, cobalt-chromium alloy, titanium alloy (such as Ti-6Al-4V titanium alloy or Ti-6Al-7Nb titanium alloy), ceramic material (such as silicon nitride (Si3N4)), or implantable-grade composite material (such as implantable-grade polyaryletherketone with filler, implantable-grade polyetheretherketone with filler, implantable-grade polyetheretherketone with carbon fiber, or implantable-grade polyetheretherketone with hydroxyapatite). The mesh part 168 also can be made, for example, from one or more materials such as resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic. The mesh part 168 also can be made, for example, from one or more materials that are resorbable, such as polylactic acid or polycaprolactone, among others, in which case callus around bone and tendon at the site of implantation would gradually remove the polymer of the implant 100, with replacement by a patient's own tissue, which would be more analogous to a natural state. The mesh part 168 also can be made from further combinations of the above-noted materials and/or hard tissues.

The mesh part 168 can have an arcuate shape similar to that of the embodiment 1004 of the implant 100, such as an arc of a semicircle of 180°, from a top view. The mesh part 168 can have a mesh pore size and a void volume adequate for mechanical performance requirements as governed by biomechanics and biology of the corresponding hard tissue and tendon or ligament for attachment. The mesh pore size can range, for example, from 100 to 1,000 microns, 200 to 800 microns, or 400 to 600 microns, among other mesh pore sizes. The void volume can range, for example, from 20% to 90%, 30% to 85%, or 40% to 80%, among other void volumes. The mesh size and void volume can vary across the mesh part 168, for example from a first side 170 of the mesh part 168 facing the hard tissue to a second side 172 of the mesh part 168 facing the tendon or ligament.

The implant assembly 1007 provides advantages by further shielding lateral surfaces of a tendon or ligament from contact with surfaces of a bone tunnel during insertion of the implant assembly 1007 into the bone tunnel, while also allowing better integration of bone and tendon or ligament following implantation.

The implant assembly 1007 can be assembled during use as follows. The implant 100, corresponding for example to embodiment 1004, with a cap 154 attached, is provided. As discussed above, the cap 154 includes a hinge 156, e.g. a living hinge. The cap 154 is pivoted away from the bottom end 106 of the shaft 102. Then a tendon or ligament is attached at the second pillars 132 along the second surface 122 of the shaft 102 of the first implant 100 without interference between the cap 154 and an end of the tendon or ligament. Next the cap 154 is pivoted toward the bottom end 106 of the shaft 102, to protect the tendon or ligament during implantation. Then the mesh part 168 is attached to the implant 100 along the shaft 102 of the implant 100, facing the second surface 122 of the first implant 100. The attachment can be, for example, based on a complementary fit between the first implant 100 and the mesh part 168. This further shields lateral surfaces of the tendon or ligament from contact with surfaces of a bone tunnel during insertion of the implant assembly 1007 into the bone tunnel, while allowing better integration of bone and tendon or ligament following implantation.

Methods of Using Implants for Attaching a Tendon or a Ligament to a Hard Tissue

Methods will now be described for use of the implant 100 for attaching a tendon or a ligament to a hard tissue in an individual in need thereof. The implant 100 is as described above.

The method includes a step of (1) preparing a bone tunnel in a bone of the individual. The preparing of the bone tunnel can comprise, for example, drilling a hole in the bone. The preparing of the bone tunnel also can comprise, for example, tapping a hole to provide a thread. In some examples the implant 100 has an implant diameter 160 between distal ends 128 of first pillars 126 at a widest portion of the shaft 102, and the preparing of the bone tunnel comprises preparing a hole in the bone that has a hole diameter that is smaller than the implant diameter 160 and/or tapping a hole to have a thread that has an inner diameter that is smaller than the implant diameter 160.

The method also includes a step of (2) attaching a tendon or a ligament to the implant 100 such that the tendon or ligament is in contact with the second pillars 132 of the implant. Residual muscle can be removed from the tendon or ligament prior to attaching the tendon or ligament to the implant 100 as needed. In some examples the attaching comprises piercing the tendon or the ligament with the second pillars 132, thereby putting the tendon or ligament in contact with the second pillars 132 of the implant 100. In some examples the attaching comprises use of a suture or an adhesive to attach the tendon or the ligament to the implant 100. In some examples the method does not comprise use of a suture or an adhesive to attach the tendon or the ligament to the implant 100. For example, the piercing can be sufficient for attaching the tendon or ligament to the implant 100, thus simplifying the attachment.

The method also includes a step of (3) inserting the implant 100 into the bone tunnel. In some examples the inserting of the implant 100 into the bone tunnel comprises driving the implant 100 into the bone tunnel by rotating the implant 100. In some examples the inserting of the implant 100 into the bone tunnel comprises pressing the implant 100 into the bone tunnel. In some examples the inserting of the implant 100 into the bone tunnel comprises pulling the implant 100 into the bone tunnel.

As noted above, the first pillars 126 may be pressed into the hard tissue, potentially eliminating micro-motion and migration of the implant 100 over time, accommodating torque, and/or eliminating the need for adhesives such as cement or grout to hold the implant 100 in place. Accordingly, in some examples, the inserting of the implant 100 can be done without use of screws or plating mechanisms. This can minimize the number and profiles of implants used in the method in an individual while still eliminating micro-motion and migration of the hard-tissue implant 100 over time. Also, in some examples, the inserting of the implant 100 can be done without use of adhesives, e.g. cement or grout. This can simplify the method while still eliminating micro-motion and migration of the hard-tissue implant 100 over time.

In some examples the inserting of the implant 100 comprises having the first pillars 126 penetrate the hard tissue, partially or completely. This can be accomplished, for example, by preparing the bone tunnel to have a diameter greater than or equal to a shaft diameter 108 at a widest portion of the shaft 102, but less than that of an implant diameter 160 between distal ends 128 of first pillars 126 at a widest portion of the shaft 102. For example, the implant 100 can be driven, pressed, or pulled into the bone tunnel such that the first pillars 126 penetrate bone of the bone tunnel to a depth of, for example, 100 to 2,000 µm, 200 to 900 µm, 300 to 800 µm, or 400 to 600 µm. Also for example, the implant 100 can be driven, pressed, or pulled into the bone tunnel such that first pillars 126 penetrate bone of the bone tunnel to a depth, relative to the height of the first pillars 126, of for example 25%, 50%, 75%, and 100% of the height of the first pillars 126. In some of these examples the inserting of the implant 100 comprises pressing or pulling the implant 100 into the bone tunnel, then rotating the implant 100 slightly. This can cause the first pillars 126 to bite into bone between the first pillars 126, resulting in the implant 100 becoming locked in place in the bone.

The method results in attaching the tendon or the ligament to the bone of the individual.

In some examples additional hard tissue can be added to the first surface 118 and/or the first pillars 126 of the implant 100 prior to implanting. For example, shavings of hard-tissue of a patient, generated during preparation work including sawing or drilling of hard tissue of the patient, can be added. This may promote growth of hard tissue into the first slots 130 of the implant 100 following implantation.

Also in some examples additional compositions can be added to the first surface 118 and/or the first pillars 126 of the implant 100 prior to implanting. Such compositions include, for example, blood, one or more antibiotics, one or more osteogenic compounds, bone marrow aspirate, and/or surface chemistry for inducing early bone ingrowth. For example, the first surface 118 and/or the first pillars 126 can be coated with one or more such compositions, with the first pillars 126 retaining the compositions during implantation. This also may promote growth of tissue into the first slots of the implant 100 following implantation.

Standard approaches for implanting the implant 100, e.g. pressing the implant 100 into the bone tunnel in the bone, are known in the art and can be used in the methods disclosed here.

The hard tissue can be selected from, for example, bones such as humerus, patella, tibia, or femur, among other hard tissues, as discussed above. As discussed, in some examples the first pillars 126 may contact a hard tissue immediately upon implantation. In some examples the first pillars 126 may contact a hard tissue over time after implantation.

The method can be applied to the embodiments and examples of the implant 100 as disclosed above. The first surface ratio and the second surface ratio can be determined as discussed above.

Thus, for example, in some examples the implant 100 further comprises a central slot 148 extending axially within the shaft 102 and a shaft hinge 150 extending axially along the shaft 102. In some of these examples the method further comprises, after steps (1) to (3), a step of (4) pushing a wedge into the central slot 148, thereby opening the shaft hinge 150 and expanding the implant 100.

It will be apparent to those skilled in the art that various modifications and variations can be made without departing from the spirit and scope of the claimed invention.

What is claimed is:
1. An implant for attaching a tendon or a ligament to a hard tissue comprising:
  (a) a shaft having a top end and a bottom end, the shaft extending between the top end and the bottom end;
  (b) a first surface of the shaft extending from the top end to the bottom end and having a cross section transverse to the shaft that is convex;
  (c) a second surface of the shaft extending from the top end to the bottom end and having a cross section transverse to the shaft that is flat or concave;
  (d) first pillars configured for contacting a hard tissue, the first pillars being distributed on the first surface across an area of at least 50 mm$^2$, and extending distally therefrom, and each first pillar being integral to the shaft, having a distal end, having a transverse area of $(100 \times 100)$ to $(2,000 \times 2,000) \mu m^2$, and having a height of 100 to 2,000 µm;
  (e) first slots configured to be occupied by the hard tissue, the first slots being defined by the first pillars and each first slot having a width of 100 to 2,000 µm as measured along the shortest distance between adjacent first pillars;

(f) second pillars configured for contacting a tendon or a ligament, the second pillars being distributed on the second surface across an area of at least 50 mm², and extending distally therefrom, and each second pillar being integral to the shaft, having a distal end, having a transverse area of (200×200) to (4,000×4,000)µm², and having a height of 100 to 10,000 µm; and (g) second slots configured to be occupied by the tendon or the ligament, the second slots being defined by the second pillars and each second slot having a width of 400 to 4,000 µm as measured along the shortest distance between adjacent second pillars; wherein:

the implant has (1) a Young's modulus of elasticity of 3 GPa to 230 GPa, (2) a first surface ratio of (i) a sum of the volumes of the first slots to (ii) a sum of the volumes of the first pillars and the volumes of the first slots of 0.40:1 to 0.90:1, and (3) a second surface ratio of (i) a sum of the volumes of the second slots to (ii) a sum of the volumes of the second pillars and the volumes of the second slots of 0.60:1 to 0.98:1, and the second surface ratio is greater than the first surface ratio.

2. The implant of claim 1, wherein the implant is made of one or more materials selected from implantable-grade polyaryletherketone that is essentially unfilled, implantable-grade polyetheretherketone, implantable-grade polyetherketoneketone, titanium, stainless steel, cobalt-chromium alloy, titanium alloy, Ti-6Al-4V titanium alloy, Ti-6Al-7Nb titanium alloy, ceramic material, silicon nitride (Si3N4), implantable-grade composite material, implantable-grade polyaryletherketone with filler, implantable-grade polyetheretherketone with filler, implantable-grade polyetheretherketone with carbon fiber, or implantable-grade polyetheretherketone with hydroxyapatite.

3. The implant of claim 1, wherein the implant is made of one or more hard tissues selected from human hard tissue, animal hard tissue, autologous hard tissue, allogenic hard tissue, xenogeneic hard tissue, human cartilage, animal cartilage, human bone, animal bone, cadaver bone, or cortical allograft.

4. The implant of claim 1, wherein the implant is made of one or more materials selected from resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic.

5. The implant of claim 1, wherein the shaft is straight.

6. The implant of claim 1, wherein the shaft is tapered toward the bottom end.

7. The implant of claim 1, wherein the shaft has a top end aperture located at the top end of the shaft.

8. The implant of claim 1, wherein the second surface of the shaft has a cross section transverse to the shaft that is flat.

9. The implant of claim 1, wherein the second surface of the shaft has a cross section transverse to the shaft that is concave.

10. The implant of claim 1, wherein the first pillars extend in a uniform direction.

11. The implant of claim 1, wherein the first pillars are perpendicular to the first surface of the shaft.

12. The implant of claim 1, wherein the first pillars are angled toward the top end.

13. The implant of claim 1, wherein the second pillars extend in a uniform direction.

14. The implant of claim 1, wherein the second pillars extend distally at an identical angle with respect to a plane bisecting the shaft.

15. The implant of claim 1, wherein the second pillars are angled toward the bottom end.

16. The implant of claim 1, wherein the transverse area of each first pillar is (250×250)µm² to (1,000×1,000)µm².

17. The implant of claim 1, wherein the height of each first pillar is 200 to 900 µm.

18. The implant of claim 1, wherein one or more of the first pillars have dimensions that differ from those of other first pillars, such that the transverse areas and/or heights, and thus volumes, of the one or more first pillars differ from those of the other first pillars.

19. The implant of claim 1, wherein the width of each first slot is 200 to 1,000 µm.

20. The implant of claim 1, wherein the transverse area of each second pillar is (400×400) µm² to (2,000×2,000) µm².

21. The implant of claim 1, wherein the height of each second pillar is 100 to 8,000 µm.

22. The implant of claim 1, wherein one or more of the second pillars have dimensions that differ from those of other second pillars, such that the transverse areas and/or heights, and thus volumes, of the one or more second pillars differ from those of the other second pillars.

23. The implant of claim 1, wherein the width of each second slot is 500 to 3,000 µm.

24. The implant of claim 1, wherein the shaft has a shaft diameter at a widest portion of the shaft and a shaft length from the top end to the bottom end, and the implant has a ratio of the shaft length to the shaft diameter of 2.0 to 10.

25. The implant of claim 1, wherein the shaft has a shaft diameter of 4 to 20 mm at a widest portion of the shaft.

26. The implant of claim 1, wherein the shaft has a shaft length of 8 to 40 mm from the top end to the bottom end.

27. The implant of claim 1, wherein one or more of the shaft, the first pillars, or the second pillars are non-porous.

28. The implant of claim 1, wherein one or more of the shaft, the first pillars, or the second pillars are porous.

29. The implant of claim 1, wherein the implant further comprises a tool-engaging portion.

30. The implant of claim 1, wherein the implant has one or more holes in the shaft.

31. The implant of claim 30, wherein the second pillars are distributed centrally along the shaft, from near the top end to near the bottom end, and a plurality of the holes are distributed peripherally along the shaft, from near the top end to near the bottom end.

32. The implant of claim 30, wherein the one or more holes are located at or near the bottom end of the shaft.

33. The implant of claim 1, wherein the implant further comprises a central slot extending axially within the shaft and a hinge extending axially along the shaft.

34. The implant of claim 1, wherein the implant further comprises a cap attached to the shaft at the bottom end of the shaft.

35. The implant of claim 34, wherein the cap is attached to shaft by a hinge.

36. A method of use of the implant of claim 1 for attaching a tendon or a ligament to a hard tissue in an individual in need thereof, the method comprising steps of:
 (1) preparing a bone tunnel in a bone of the individual;
 (2) attaching a tendon or a ligament to the implant such that the tendon or ligament is in contact with the second pillars of the implant; and
 (3) inserting the implant into the bone tunnel;

thereby attaching the tendon or the ligament to the bone of the individual.

37. The method of claim 36, wherein the preparing of the bone tunnel comprises drilling a hole in the bone.

38. The method of claim 36, wherein the implant has an implant diameter between distal ends of pillars at a widest portion of the shaft, and the preparing of the bone tunnel comprises preparing a hole in the bone that has a hole diameter that is smaller than the implant diameter.

39. The method of claim 36, wherein the attaching of the tendon or the ligament to the implant comprises piercing the tendon or the ligament with the second pillars, thereby putting the tendon or ligament in contact with the second pillars of the implant.

40. The method of claim 36, wherein the inserting of the implant into the bone tunnel comprises driving the implant into the bone tunnel by rotating the implant.

41. The method of claim 36, wherein the inserting of the implant into the bone tunnel comprises pressing the implant into the bone tunnel.

42. The method of claim 36, wherein the implant further comprises a central slot extending axially within the shaft and a hinge extending axially along the shaft, the method further comprising, after steps (1) to (3), a step of (4) pushing a wedge into the central slot, thereby opening the hinge and expanding the implant.

43. The method of claim 36, wherein the method does not comprise use of a suture or an adhesive to secure the tendon or the ligament to the implant.

44. An implant assembly for attaching a tendon or a ligament to a hard tissue comprising first and second implants of claim 1, and a cap, wherein:
   the cap is attached to the shaft of the first implant at the bottom end of the shaft;
   the second implant is attached to the first implant along the shaft of the first implant;
   and a second surface of the shaft of the second implant faces the second surface of the shaft of the first implant.

45. An implant assembly for attaching a tendon or a ligament to a hard tissue comprising the implant of claim 1, a cap, and a mesh part, wherein;
   the cap is attached to the shaft of the implant at the bottom end of the shaft;
   the mesh part comprises a first side configured to face a hard tissue and a second side configured to face a tendon or ligament and has an arcuate shape;
   the mesh part is attached to the implant along the shaft of the implant; and
   the second side of the mesh part faces the second surface of the shaft of the implant.

* * * * *